US009893299B2

(12) United States Patent
Stoessel et al.

(10) Patent No.: US 9,893,299 B2
(45) Date of Patent: Feb. 13, 2018

(54) HETEROCYCLIC COMPOUNDS

(71) Applicant: Merck Patent GmbH, Darmstadt (DE)

(72) Inventors: Philipp Stoessel, Frankfurt am Main (DE); Nils Koenen, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 15/021,027

(22) PCT Filed: Aug. 13, 2014

(86) PCT No.: PCT/EP2014/002223
§ 371 (c)(1),
(2) Date: Mar. 10, 2016

(87) PCT Pub. No.: WO2015/036078
PCT Pub. Date: Mar. 19, 2015

(65) Prior Publication Data
US 2016/0226003 A1    Aug. 4, 2016

(30) Foreign Application Priority Data

Sep. 11, 2013  (EP) .................................. 13004411
Dec. 20, 2013  (EP) .................................. 13005961

(51) Int. Cl.
| | |
|---|---|
| *H01L 51/00* | (2006.01) |
| *C09K 11/06* | (2006.01) |
| *H05B 33/10* | (2006.01) |
| *C07D 221/16* | (2006.01) |
| *C07D 221/18* | (2006.01) |
| *C07D 221/22* | (2006.01) |
| *C07D 237/26* | (2006.01) |
| *C07D 471/04* | (2006.01) |
| *C07D 471/14* | (2006.01) |
| *C07D 471/22* | (2006.01) |
| *C07D 491/048* | (2006.01) |
| *C09B 57/00* | (2006.01) |
| *C09B 3/14* | (2006.01) |
| *C09B 5/00* | (2006.01) |
| *C09B 5/02* | (2006.01) |
| *C07D 221/20* | (2006.01) |
| *C07D 471/18* | (2006.01) |
| *C07D 491/08* | (2006.01) |
| *C07D 491/147* | (2006.01) |
| *C09K 11/02* | (2006.01) |
| *H01L 51/50* | (2006.01) |

(52) U.S. Cl.
CPC ........ *H01L 51/0072* (2013.01); *C07D 221/16* (2013.01); *C07D 221/18* (2013.01); *C07D 221/20* (2013.01); *C07D 221/22* (2013.01); *C07D 237/26* (2013.01); *C07D 471/04* (2013.01); *C07D 471/14* (2013.01); *C07D 471/18* (2013.01); *C07D 471/22* (2013.01); *C07D 491/048* (2013.01); *C07D 491/08* (2013.01); *C07D 491/147* (2013.01); *C09B 3/14* (2013.01); *C09B 5/00* (2013.01); *C09B 5/008* (2013.01); *C09B 5/028* (2013.01); *C09B 57/00* (2013.01); *C09B 57/001* (2013.01); *C09K 11/02* (2013.01); *C09K 11/06* (2013.01); *H01L 51/0067* (2013.01); *H01L 51/0071* (2013.01); *H05B 33/10* (2013.01); *C09K 2211/1007* (2013.01); *C09K 2211/1011* (2013.01); *C09K 2211/1029* (2013.01); *C09K 2211/1044* (2013.01); *C09K 2211/1059* (2013.01); *C09K 2211/1088* (2013.01); *H01L 51/0085* (2013.01); *H01L 51/0087* (2013.01); *H01L 51/5012* (2013.01); *H01L 51/5016* (2013.01); *H01L 51/5072* (2013.01); *Y02E 10/549* (2013.01)

(58) Field of Classification Search
CPC ............. H01L 51/0072; H01L 51/0071; H01L 51/0067; H01L 51/5016; H01L 51/0085; H01L 51/0087; C09K 11/06; C07D 221/18
USPC .......................................... 252/500; 257/798
See application file for complete search history.

(56) References Cited

U.S. PATENT DOCUMENTS

| | | | |
|---|---|---|---|
| 2007/0213355 A1 | 9/2007 | Capraro et al. | |
| 2010/0317657 A1 | 12/2010 | Furet et al. | |
| 2012/0108627 A1* | 5/2012 | Kumar ................. | C07D 471/04 514/293 |
| 2016/0233443 A1* | 8/2016 | Stoessel ................. | C09K 11/06 |
| 2016/0251359 A1* | 9/2016 | Heffernan ............ | C07D 471/04 |
| 2016/0365520 A1* | 12/2016 | Stoessel ............. | H01L 51/0085 |
| 2017/0170413 A1* | 6/2017 | Stoessel ............. | H01L 51/0085 |
| 2017/0250353 A1* | 8/2017 | Koenen ............... | H01L 51/0085 |

FOREIGN PATENT DOCUMENTS

WO    WO-2011001212 A1    1/2011

OTHER PUBLICATIONS

STN reg. No. 1678504-83-0, Apr. 7, 2015.*
International Search Report for PCT/EP2014/002223 dated Jan. 21, 2015.
Maslankiewicz, A., et al., "Azinyl Sulfides, Part 86. Derivatives of Some Cyclic 3,4-Quinolinediyl Bis-sulfides with N, N-Dimethylcarbamoyl and N-Methyl-N-formylaminomethyl Subsittuents in the 2-Quinolinyl Position", Journal of Heterocyclic Chemistry, vol. 42, No. 6, (2006), pp. 1161-1166.
Maslankiewicz, A., et al., "Sulfurization of Azines; Part IX. (1-Chloroalkylthio)-azines", Synthesis 1986, No. 10, (1986), pp. 835-839.

(Continued)

*Primary Examiner* — Douglas McGinty
(74) *Attorney, Agent, or Firm* — Drinker Biddle & Reath LLP

(57) ABSTRACT

The invention concerns heterocyclic compounds and electronic devices, in particular organic electroluminescent devices, containing these compounds.

21 Claims, No Drawings

(56) References Cited

OTHER PUBLICATIONS

Reid, W., et al., "Reaktionen mit Diazocarbonyl-Verbindungen, Die thermische Zersetzung von o-Chinondiaziden", Justus Liebigs Annalen der Chemie, vol. 639, (1961), pp. 32-56.

Reid, W., et al., "Thermische Zersetzung von o-Chinondiaziden", Naturwissenschaften, vol. 46, No. 15, (1959), p. 474.

Some, S., et al., "New protocols for the synthesis of 3,4-annulated and 4-substituted quinolines from β-bromo-α, β-unsaturated aldehydes and 1-bromo-2-nitrobenzene or 2-bromoacetanilide", Tetrahedron Letters, vol. 48, No. 20, (2007), pp. 3609-3612.

* cited by examiner

HETEROCYCLIC COMPOUNDS

CROSS-REFERENCE TO RELATED APPLICATIONS

This application is a national stage application (under 35 U.S.C. § 371) of PCT/EP2014/002223, filed Aug. 13, 2014, which claims benefit of European Application Nos. 13004411.8, filed Sep. 11, 2013, and 13005961.1, filed Dec. 20, 2013, all of which are incorporated herein by reference in their entireties.

The present invention relates to heterocyclic compounds suitable for use in electronic devices. The present invention further relates to processes for preparation thereof and to electronic devices.

Electronic devices containing organic, organometallic and/or polymeric semiconductors are becoming increasingly important, and are being used in many commercial products for reasons of cost and because of their performance. Examples here include organic-based charge transport materials (for example triarylamine-based hole transporters) in photocopiers, organic or polymeric light-emitting diodes (OLEDs or PLEDs) and in readout and display devices or organic photoreceptors in photocopiers. Organic solar cells (O-SCs), organic field-effect transistors (O-FETs), organic thin-film transistors (O-TFTs), organic integrated circuits (O-ICs), organic optical amplifiers and organic laser diodes (O-lasers) are at an advanced stage of development and may have great future significance.

Many of these electronic devices, irrespective of the respective end use, have the following general layer structure which can be adjusted for the particular application:
(1) substrate,
(2) electrode, frequently metallic or inorganic, but also composed of organic or polymeric conductive materials,
(3) charge injection layer(s) or interlayer(s), for example to compensate for unevenness in the electrode ("planarization layer"), frequently composed of a conductive doped polymer,
(4) organic semiconductors,
(5) possibly further charge transport, charge injection or charge blocker layers,
(6) counterelectrode, materials as specified in (2),
(7) encapsulation.

The above arrangement is the general structure of an organic electronic device, it being possible to combine various layers, such that the result in the simplest case is an arrangement composed of two electrodes with an organic layer in between. In this case, the organic layer fulfills all functions including the emission of light in the case of OLEDs. A system of this kind is described, for example, in WO 90/13148 A1, based on poly(p-phenylenes).

Known electronic devices have a useful profile of properties. However, there is a constant need to improve the properties of these devices.

These properties especially include the energy efficiency with which an electronic device solves the problem defined. In the case of organic light-emitting diodes, which may be based either on low molecular weight compounds or on polymeric materials, the light yield in particular should be sufficiently high that a minimum amount of electrical power has to be applied to achieve a particular luminous flux. In addition, a minimum voltage should also be necessary to achieve a defined luminance. A further particular problem is the lifetime of the electronic devices.

It is therefore an object of the present invention to provide novel compounds which lead to electronic devices having improved properties. It is a particular object to provide hole blacker materials, electron injection materials, electron transport materials, electron-transporting matrix materials for mixed matrix systems and/or singlet matrix materials which exhibit improved properties in relation to efficiency, operating voltage and/or lifetime. Moreover, the compounds should be processible in a very simple manner, and especially exhibit good solubility and film formation.

A further object can be considered that of providing electronic devices having excellent performance very inexpensively and in constant quality.

Furthermore, it should be possible to use or adapt the electronic devices for many purposes. More particularly, the performance of the electronic devices should be maintained over a broad temperature range.

It has been found that, surprisingly, these objects and others which are not specified explicitly but can be inferred or discerned directly from the connections discussed herein by way of introduction are achieved by compounds having all the features of claim 1. Appropriate modifications to the compounds of the invention are protected in the dependent claims that refer back to claim 1.

The invention thus provides a compound comprising at least one structure of the formula (1)

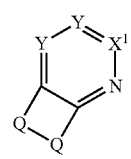

Formula (1)

where the symbols used are as follows:
Q is the same or different at each instance and is X=X, O, NR, S, SO, $SO_2$, PR, POR or BR, where at least one Q is X=X;
 it is preferable when Q is the same or different at each instance and is X=X, $SO_2$, BR, O or NR, where at least one Q is X=X;
 it is very preferable when Q is the same or different at each instance and is X=X, O or NR, where at least one Q is X=X;
 it is very particularly preferable when Q is the same or different at each instance and is X=X or O, where at least one Q is X=X;
 it is especially preferable when both Q are X=X;
$X^1$ is CR, N, preferably CR;
X is the same or different at each instance and is N or CR, preferably CR;
Y is the same or different at each instance and is CR;
R is the same or different at each instance and is H, D, F, Cl, Br, I, $N(R^1)_2$, CN, $NO_2$, OH, COOH, C(=O)$N(R^1)_2$, $Si(R^1)_3$, $B(OR^1)_2$, C(=O)$R^1$, P(=O)$(R^1)_2$, S(=O)$R^1$, S(=O)$_2R^1$, $OSO_2R^1$, a straight-chain alkyl, alkoxy or thioalkoxy group having 1 to 20 carbon atoms or an alkenyl or alkynyl group having 2 to 20 carbon atoms or a branched or cyclic alkyl, alkoxy or thioalkoxy group having 3 to 20 carbon atoms, each of which may be substituted by one or more $R^1$ radicals, where one or more nonadjacent $CH_2$ groups may be replaced by $R^1$C=$CR^1$, C≡C, $Si(R^1)_2$, C=O, $NR^1$, O, S or $CONR^1$ and where one or more hydrogen atoms may be replaced by D, F, Cl, Br, I or CN, or an aromatic or heteroaromatic ring system which has 5 to 60 aromatic ring atoms and may be substituted in each case by one or more $R^1$ radicals, or an aryloxy or heteroaryloxy group which has 5 to 40 aromatic ring atoms and may be substituted by one or more $R^1$ radicals, or an aralkyl or heteroaralkyl group which has 5 to 40 aromatic ring atoms and may be substituted by one or more $R^1$ radicals, or a diarylamino group, diheteroarylamino group or arylheteroarylamino group which has 10 to 40 aromatic ring atoms and may be substituted by one or more $R^1$ radicals; at the same time, two adjacent R radicals together may also form a mono- or polycyclic, aliphatic, aromatic or heteroaromatic ring system;

$R^1$ is the same or different at each instance and is H, D, F, Cl, Br, I, $N(R^2)_2$, CN, $NO_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 20 carbon atoms or an alkenyl or alkynyl group having 2 to 20 carbon atoms or a branched or cyclic alkyl, alkoxy or thioalkoxy group having 3 to 20 carbon atoms, each of which may be substituted by one or more $R^2$ radicals, where one or more nonadjacent $CH_2$ groups may be replaced by $R^2C=CR^2$, $C\equiv C$, $Si(R^2)_2$, $C=O$, $NR^2$, O, S or $CONR^2$ and where one or more hydrogen atoms may be replaced by D, F, Cl, Br, I, CN or $NO_2$, or an aromatic or heteroaromatic ring system which has 5 to 60 aromatic ring atoms and may be substituted in each case by one or more $R^2$ radicals, or an aryloxy or heteroaryloxy group which has 5 to 40 aromatic ring atoms and may be substituted by one or more $R^2$ radicals, or an aralkyl or heteroaralkyl group which has 5 to 40 aromatic ring atoms and may be substituted by one or more $R^2$ radicals, or a diarylamino group, diheteroarylamino group or arylheteroarylamino group which has 10 to 40 aromatic ring atoms and may be substituted by one or more $R^2$ radicals; at the same time, two or more adjacent $R^1$ radicals together, or $R^1$ together with R, may form a mono- or polycyclic, aliphatic, aromatic or heteroaromatic ring system;

$R^2$ is the same or different at each instance and is H, D, F or an aliphatic, aromatic and/or heteroaromatic hydrocarbyl radical having 1 to 20 carbon atoms, in which one or more hydrogen atoms may also be replaced by F; at the same time, two or more $R^2$ substituents together may also form a mono- or polycyclic aliphatic ring system;

which is characterized in that
the respective R radicals of the two Y groups together with the carbon atoms of the heteroaromatic ring form a ring of the following formulae;

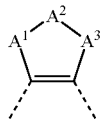

Formula (5)

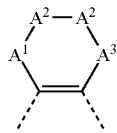

Formula (6)

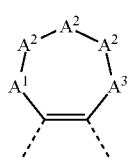

Formula (7)

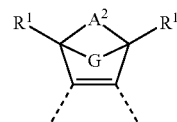

(Formula 8)

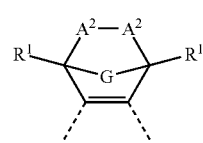

Formula (9)

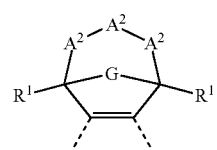

Formula (10)

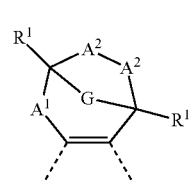

Formula (11)

where
$A^1, A^3$ is the same or different at each instance and is $C(R^3)_2$, O, S, $NR^3$ or $C(=O)$;
$A^2$ is $C(R^1)_2$, O, S, $NR^3$ or $C(=O)$;
G is a bivalent group selected from O, S, $N(R^2)$, $B(R^2)$, $Si(R^2)_2$, $C=O$, $C=NR^2$, $C=C(R^2)_2$, $S=O$, $SO_2$, $P(R^2)$ and $P(=O)R^2$, an alkylene group which has 1, 2 or 3 carbon atoms and may be substituted by one or more $R^2$ radicals, $-CR^2=CR^2-$ or an ortho-bonded arylene or heteroarylene group which has 5 to 14 aromatic ring atoms and may be substituted by one or more $R^2$ radicals;
and where the carbon-carbon double bond shown in the formulae (5) to (11) corresponds to an aromatic double bond from the heteroaromatic ring to which the groups of the formulae (5) to (11) bind;
$R^3$ is the same or different at each instance and is F, a straight-chain alkyl or alkoxy group having 1 to 10 carbon atoms, a branched or cyclic alkyl or alkoxy group having 3 to 10 carbon atoms, each of which may be substituted by one or more $R^2$ radicals, where one or more nonadjacent $CH_2$ groups may be replaced by $R^2C=CR^2$, $C\equiv C$, $Si(R^2)_2$, $C=O$, $NR^2$, O, S or $CONR^2$, and where one or more hydrogen atoms may be replaced by D or F, or an aromatic or heteroaromatic ring system which has 5 to 24 aromatic ring atoms and may be substituted in each case by one or more $R^2$ radicals, or an aryloxy or heteroaryloxy group which has 5 to 24 aromatic ring atoms and may be substituted by one or more $R^2$ radicals, or an aralkyl or heteroaralkyl group which has 5 to 24 aromatic ring atoms and may be substituted by one or more $R^2$ radicals; at the same time, two $R^3$ radicals bonded to the same carbon atom together may form an aliphatic or aromatic ring system and thus form a Spiro system; in addition, $R^3$ with an adjacent R or $R^1$ radical may form an aliphatic ring system;

with the proviso that no two identical heteroatoms in the aforementioned groups are bonded directly to one another and no two $C=O$ groups are bonded directly to one another, and, in addition, if the two Y groups together form a ring structure of the formulae (12) or (13)

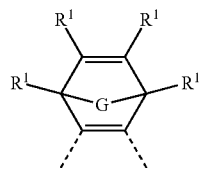

Formula (12)

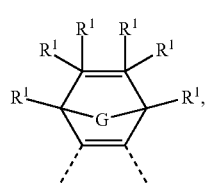

Formula (13)

the $X^1$ radical is not a group of the formula (14)

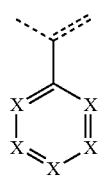

Formula (14)

in which X is as defined above and the dotted lines represent the bonds of the carbon atoms of the $X^1$ radical to two further carbon atoms of the ring including the $X^1$ radical of formula (1).

It is preferable when G in the compound of the formula (1) is selected from O, $N(R^2)$, an alkylene group which has 1, 2 or 3 carbon atoms and may be substituted by one or more $R^2$ radicals, —$CR^2$=$CR^2$— or an ortho-bonded arylene or heteroarylene group which has 5 to 14 aromatic ring atoms and may be substituted by one or more $R^2$ radicals.

It is very preferable when G in the compound of the formula (1) is selected from O, an alkylene group which has 1, 2 or 3 carbon atoms and may be substituted by one or more $R^2$ radicals, —$CR^2$=$CR^2$— or an ortho-bonded arylene or heteroarylene group which has 5 to 14 aromatic ring atoms and may be substituted by one or more $R^2$ radicals.

It is very particularly preferable when G in the compound of the formula (1) is selected from an alkylene group which has 1, 2 or 3 carbon atoms and may be substituted by one or more $R^2$ radicals, —$CR^2$=$CR^2$— or an ortho-bonded arylene or heteroarylene group which has 5 to 14 aromatic ring atoms and may be substituted by one or more $R^2$ radicals.

If G is an alkylene group, it may be a 1,1-, 1,2- or 1,3-alkylene group.

At the same time, the presence of an additional ring based on the Y groups is essential to the invention, preferably of a fused-on ring system which is more preferably aliphatic. As apparent from the abovementioned formula (1), the Y radical does not contain any acidic benzylic protons. What is meant by acidic benzylic protons in the context of the present invention is defined further down.

In the above-depicted structures of the formula (1) and the further embodiments of these structures specified as preferred, a double bond is formally depicted on the carbon atoms to which the Y radicals are bonded. This is a simplification of the chemical structure, since these two carbon atoms are incorporated into a heteroaromatic system and hence the bond between these two carbon atoms is formally between the bonding level of a single bond and that of a double bond. The drawing of the formal double bond should thus not be interpreted so as to limit the structure; instead, it will be apparent to the person skilled in the art that what is meant thereby is an aromatic bond.

The absence of acidic benzylic protons in the formulae (5) to (7) is achieved by virtue of $A^1$ and $A^3$, when they are $C(R^3)_2$, being defined such that $R^3$ is not hydrogen. The absence of acidic benzylic protons is achieved in the formulae (8) to (11) in that the structure is a bicyclic structure. Because of the rigid arrangement, $R^1$, when it is H, is much less acidic than benzylic protons since the corresponding anion of the bicyclic structure is not mesomerically stabilized. Even when $R^1$ in formulae (8) to (11) is H, this is therefore a non-acidic proton in the context of the present application.

In this context, "adjacent carbon atoms" means that the carbon atoms are bonded directly to one another. In addition, "adjacent radicals" in the definition of the radicals means that these radicals are bonded to the same carbon atom or to adjacent carbon atoms. These definitions apply correspondingly, inter alia, to the terms "adjacent groups" and "adjacent substituents".

An aryl group in the context of this invention contains 6 to 40 carbon atoms; a heteroaryl group in the context of this invention contains 2 to 40 carbon atoms and at least one heteroatom, with the proviso that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 60 carbon atoms in the ring system. A heteroaromatic ring system in the context of this invention contains 1 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. are also to be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl or terphenyl, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$- to $C_{40}$-alkyl group in which individual hydrogen atoms or $CH_2$ groups may also be replaced by the abovementioned groups are understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5-60 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In addition, it may be the case that the heteroaromatic ring system having the $X^1$ radical is a system having 10 to 30 aromatic ring atoms, preferably 10 to 24 and more preferably 10 to 18.

Preferred compounds are those comprising structures of the formula (15)

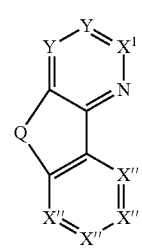

Formula (15)

where X″ is the same or different at each instance and is $CR^1$ or N, preference being given to $CR^1$, where the symbols used are each as defined above.

Preference is further given to compounds having structures of the formulae (16), (17), (18), (19), (20) and/or (21)

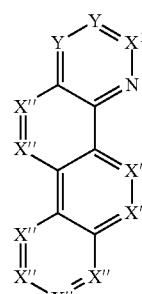

Formula (16)

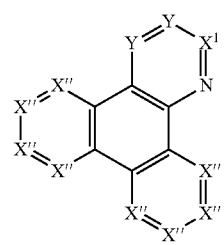

Formula (17)

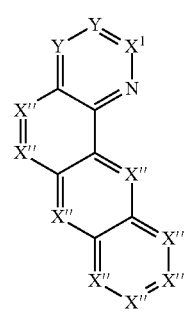

Formula (18)

-continued

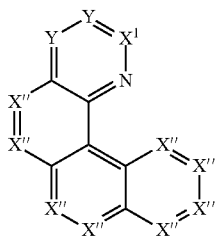

Formula (19)

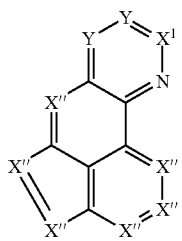

Formula (20)

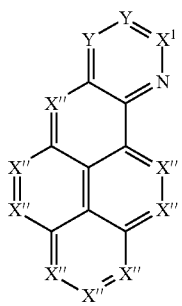

Formula (21)

where the symbols used have the definitions given above.

It is preferable in the context of the present invention when not more than one of the $A^2$ groups in the formulae (5) to (11) is a group other than $C(R^1)_2$, it being very preferable when all $A^2$ groups are the same or different at each instance and are a $C(R^1)_2$ group.

It is very preferable in the context of the present invention when not more than one of the $A^1$, $A^3$ and $A^2$ groups in the formulae (5) to (11) is a group other than $C(R^1)_2$ or $C(R^3)_2$, it being very preferable when all $A^1$, $A^3$ and $A^2$ groups are the same or different at each instance and are a $C(R^1)_2$ or $C(R^3)_2$ group.

Preference is further given to compounds of formula (1) in which the ring structures of one of the formulae (5), (6), (7), (8), (9), (10) and/or (11) not more than two and preferably not more than one of the $A^1$, $A^2$ and $A^3$ groups is O, S or $NR^3$, and especially preferably none of the $A^1$, $A^2$ and $A^3$ groups is O, S or $NR^3$.

Preference is further given to compounds of formula (1) in which not more than one Y and preferably no Y is C(=O). In addition, it may be the case that, in the ring structures of one of the formulae (5), (6), (7), (8), (9), (10) and/or (11), not more than two and preferably not more than one of the $A^1$, $A^2$ and $A^3$ groups is C(=O), and especially preferably none of the $A^1$, $A^2$ and $A^3$ groups is C(=O).

Preference is further given to compounds having the feature that, in the ring structures of one of the formulae (5), (6), (7), (8), (9), (10) and/or (11), at least one of the $A^1$ and $A^3$ groups is the same or different and is O or $NR^3$ and $A^2$ is $C(R^1)_2$.

In a further configuration of the present invention, preference is given to compounds which are characterized in that, in the ring structures of one of the formulae (5), (6), (7), (8), (9), (10) and/or (11), the $A^1$ and $A^3$ groups are the same or different at each instance and are $C(R^3)_2$ and $A^2$ is $C(R^1)_2$, preferably $C(R^3)_2$ or $CH_2$ and more preferably $CH_2$.

Preference is further given to compounds in which, in the ring structures of formula (8), (9), (10) and/or (11), the $R^1$ radicals bonded to the bridgehead are H, D, F or $CH_3$.

It may further be the case that, in the structure of formula (1), the two Y groups form a ring structure of one of the following formulae (5-A), (5-B), (5-C), (5-D), (5-E) and/or (5-F):

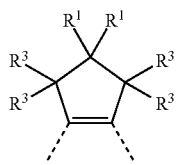

Formula (5-A)

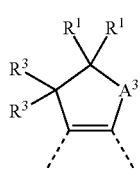

Formula (5-B)

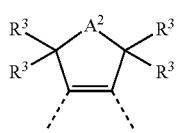

Formula (5-C)

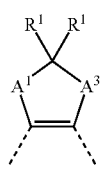

Formula (5-D)

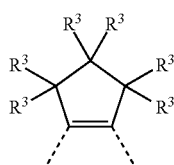

Formula (5-E)

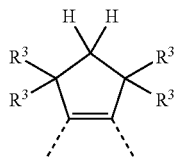

Formula (5-F)

where $A^1$, $A^2$ and $A^3$ are the same or different at each instance and are O or $NR^3$, the dotted lines the bonds of the two Y radicals to the ring comprising the $X^1$ radical of formula (1), $R^1$ and $R^3$ are each as defined above. Of the compounds mentioned having structures of the formulae (5-A), (5-B), (5-C), (5-D), (5-E) or (5-F), preference is given to compounds having structures of the formulae (5-A), (5-B), (5-C), (5-E) and/or (5-F) and particular preference to those having structures of the formulae (5-C), (5-E) and/or (5-F).

Examples of particularly preferred groups of the formula (5-A) to (5-F) are the following groups of the formulae (5-1) to (5-69):

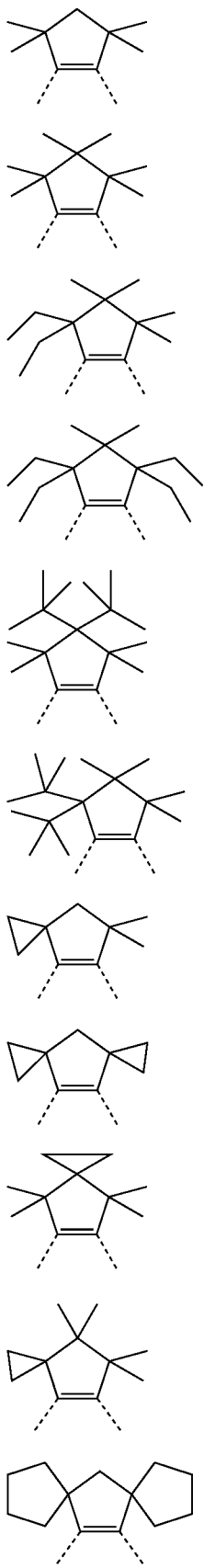
Formula (5-1)
Formula (5-2)
Formula (5-3)
Formula (5-4)
Formula (5-5)
Formula (5-6)
Formula (5-7)
Formula (5-8)
Formula (5-9)
Formula (5-10)
Formula (5-11)
Formula (5-12)
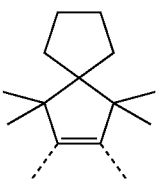
Formula (5-13)
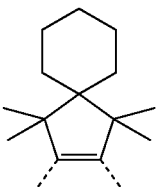
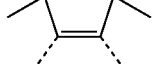
Formula (5-14)
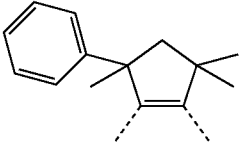
Formula (5-15)
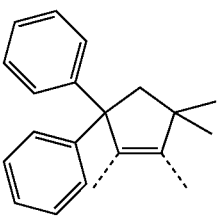
Formula (5-16)
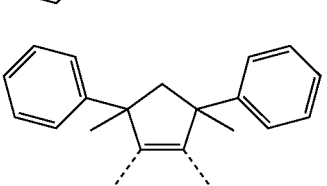
Formula (5-17)
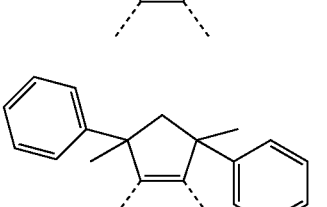
Formula (5-18)
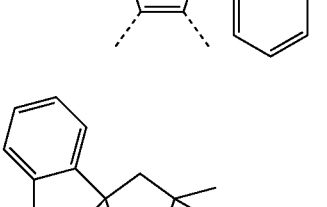
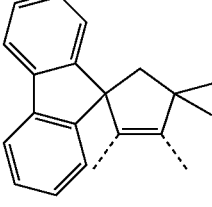
Formula (5-19)
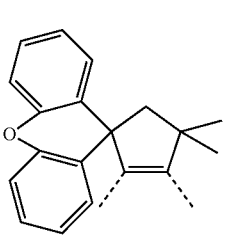

Formula (5-20)
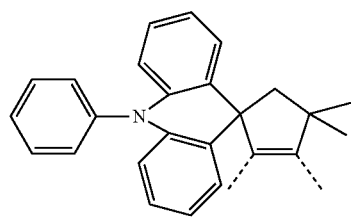
Formula (5-21)
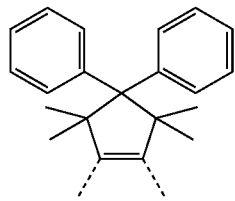
Formula (5-22)
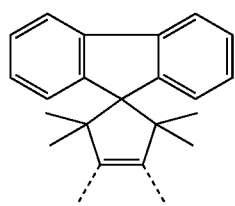
Formula (5-23)
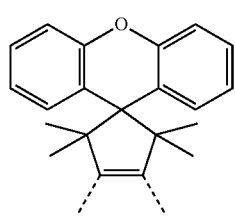
Formula (5-24)
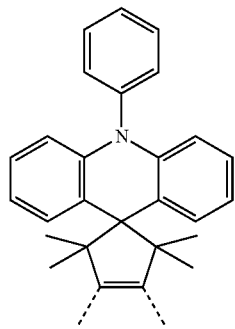
Formula (5-25)
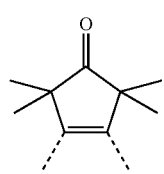
Formula (5-26)
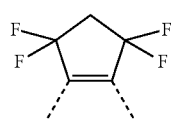
Formula (5-27)
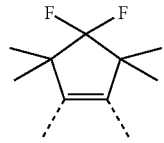
Formula (5-28)
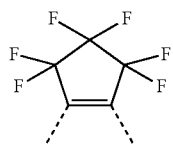
Formula (5-29)
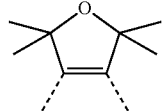
Formula (5-30)
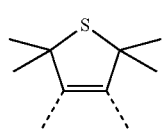
Formula (5-31)
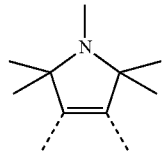
Formula (5-32)
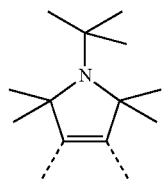
Formula (5-33)
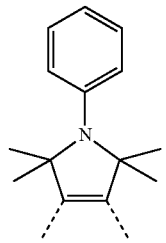
Formula (5-34)
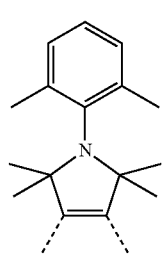
Formula (5-35)
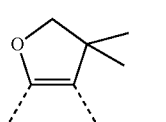
Formula (5-36)
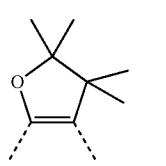

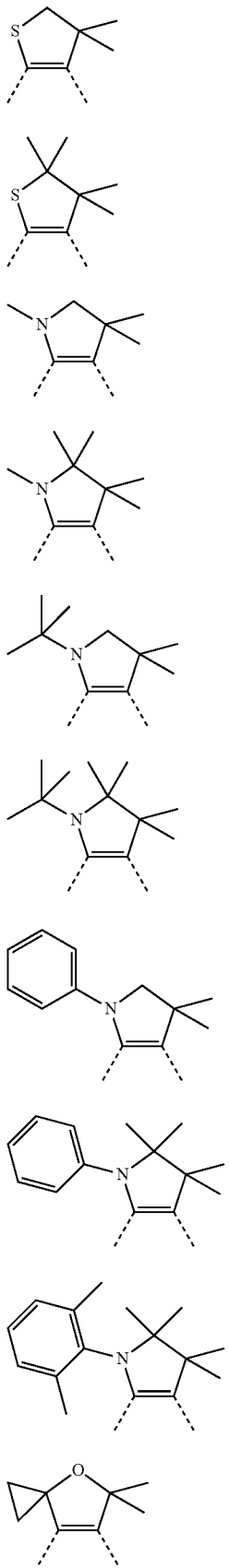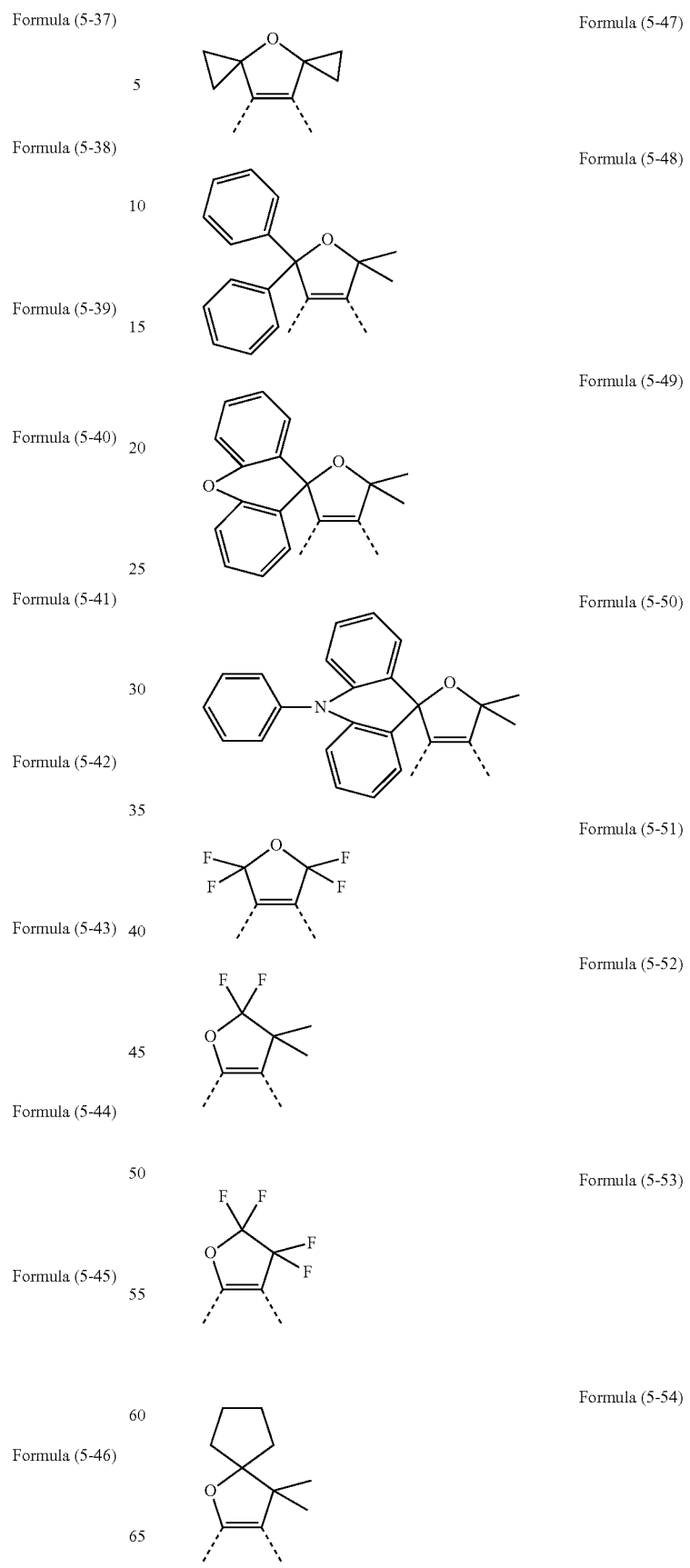

-continued
Formula (5-55)
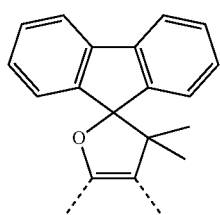
Formula (5-56)
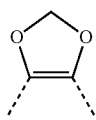
Formula (5-57)
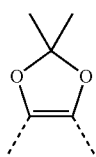
Formula (5-58)
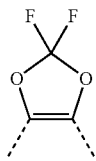
Formula (5-59)
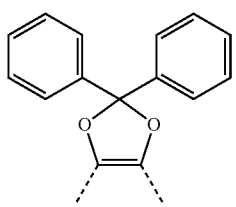
Formula (5-60)
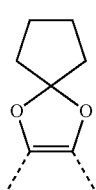
Formula (5-61)
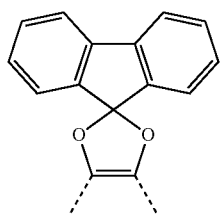
Formula (5-62)
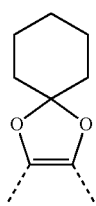
Formula (5-63)
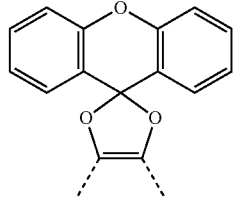
Formula (5-64)
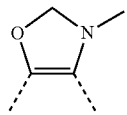
Formula (5-65)
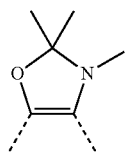
Formula (5-66)
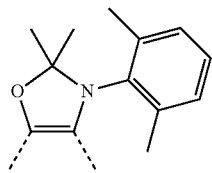
Formula (5-67)
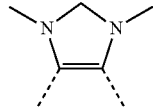
Formula (5-68)
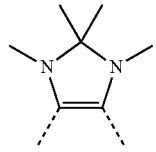
Formula (5-69)
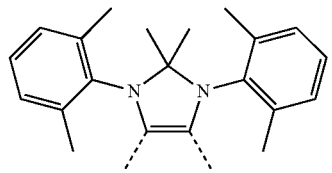
In a particular aspect of the present invention, it may be the case that, in the structure of formula (1), the two Y groups form a ring structure of one of the following formulae (6-A) to (6-F):
Formula (6-A)
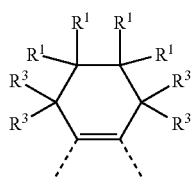

Formula (6-B)

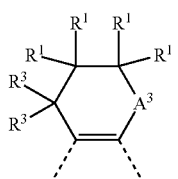

Formula (6-C)

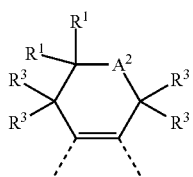

Formula (6-D)

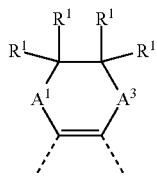

Formula (6-E)

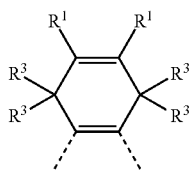

Formula (6-F)

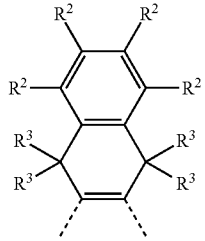

where $A^1$, $A^2$ and $A^3$ are the same or different at each instance and are O or $NR^3$, the dotted lines the bonds of the two Y radicals to the ring comprising the $X^1$ radical of formula (1), $R^1$ and $R^3$ are each as defined above.

Of the compounds mentioned having structures of the formulae (6-A) to (6-F), preference is given to compounds having structures of the formulae (6-A), (6-B), (6-C), (6-E) and/or (6-F) and particular preference to those having structures of the formulae (6-A), (6-E) and/or (6-F).

Examples of particularly preferred groups of the formula (6-A) to (6-F) are the following groups of the formulae (6-1) to (6-14):

Formula (6-1)

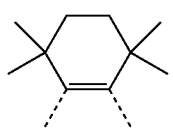

Formula (6-2)

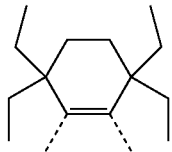

Formula (6-3)

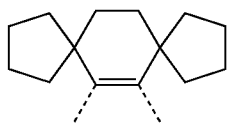

Formula (6-4)

Formula (6-5)

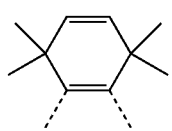

Formula (6-6)

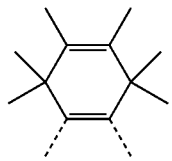

Formula (6-7)

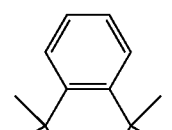

Formula (6-8)

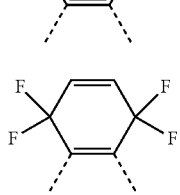

Formula (6-9)

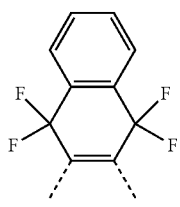

Formula (6-10)

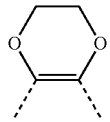

Formula (6-11)

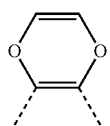

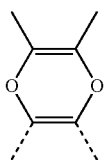

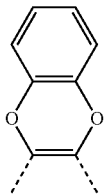

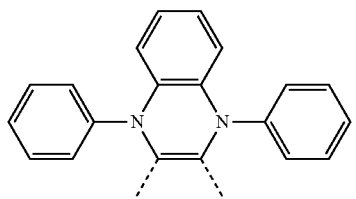

Preferably, the two Y groups in compounds having structures of formula (1) may form a ring structure of one of the following formulae (7-A) to (7-E):

Formula (7-A)

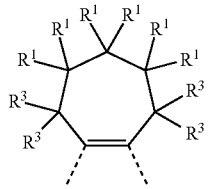

Formula (7-B)

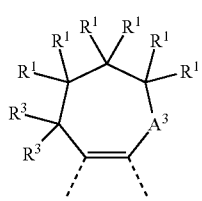

Formula (7-C)

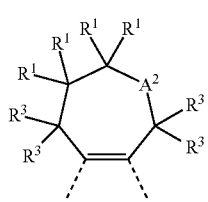

Formula (7-D)

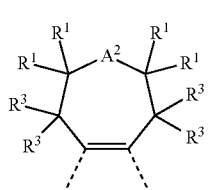

Formula (7-E)

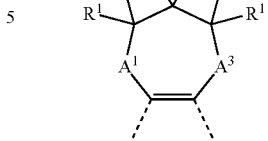

where $R^1$ and $R^3$ are each as defined above, $A^1$, $A^2$ and $A^3$ are the same or different at each instance and are O or $NR^3$ and the dotted lines are the bonds of the two Y radicals to the ring comprising the $X^1$ radical of formula (1).

One example of a particularly preferred group of the formula (7-A) is the following group of the formula (7-1):

Formula (7-1)

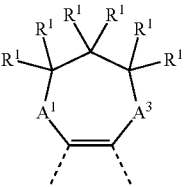

Preferably, the two Y groups in the structure of formula (1) may form a ring structure of one of the following formulae (8-A) to (8-C):

Formula (8-A)

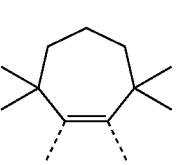

Formula (8-B)

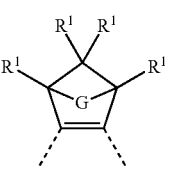

Formula (8-C)

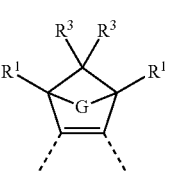

where the symbols used are each as defined above and the dotted lines represent the bonds of the two Y radicals to the ring comprising the $X^1$ radical of formula (1). Of the compounds mentioned having ring structures according to (8-A) to (8-C), preference is given to those compounds which have structures of formula (8-B) and (8-C), particular preference being given to compounds having structures of formula (8-C).

Even more preferred are the formulae (8-A1) to (8-C1)

Formula (8-A1)
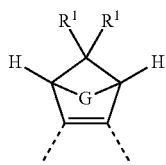

Formula (8-B1)
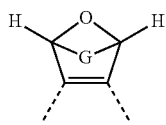

Formula (8-C1)
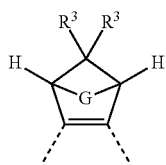

Examples of particularly preferred groups of the formula (8-A) and (8-C) are the following groups of the formulae (8-1) to (8-3):

Formula (8-1)

Formula (8-2)
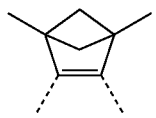

Formula (8-3)
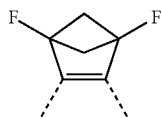

Preference is further given to compounds in which the two Y groups in the structure of formula (1) form a ring structure of one of the following formulae (9-A), (10-A) and (11-A):

Formula (9-A)
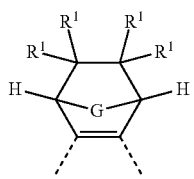

Formula (10-A)
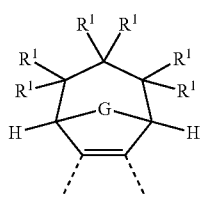

Formula (11-A)
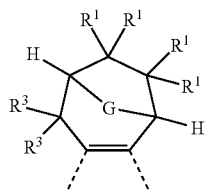

where the symbols used are each as defined above and the dotted lines represent the bonds of the two Y radicals to the ring comprising the $X^1$ radical of formula (1).

Examples of particularly preferred groups of the formula (9-A), (10-A) and (11-A) are the following groups of the formulae (9-1) to (9-27):

Formula (9-1)

Formula (9-2)
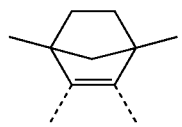

Formula (9-3)
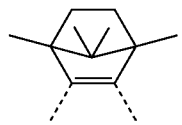

Formula (9-4)
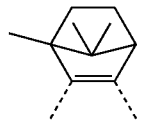

Formula (9-5)
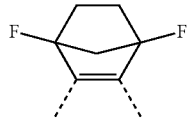

Formula (9-6)
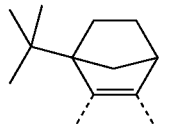

Formula (9-7)
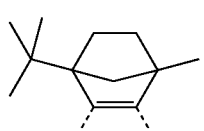

Formula (9-8)
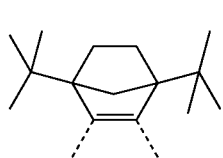

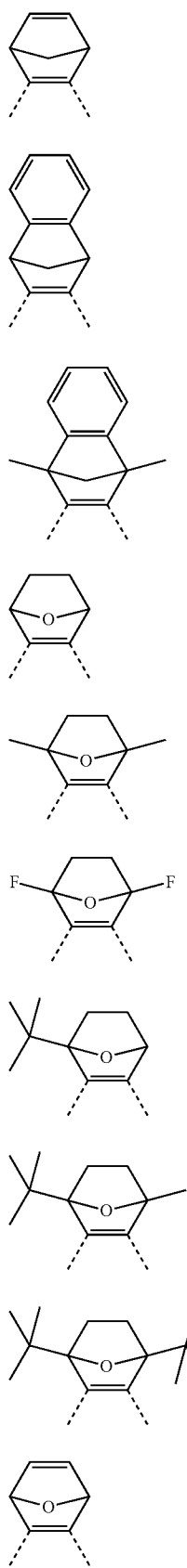
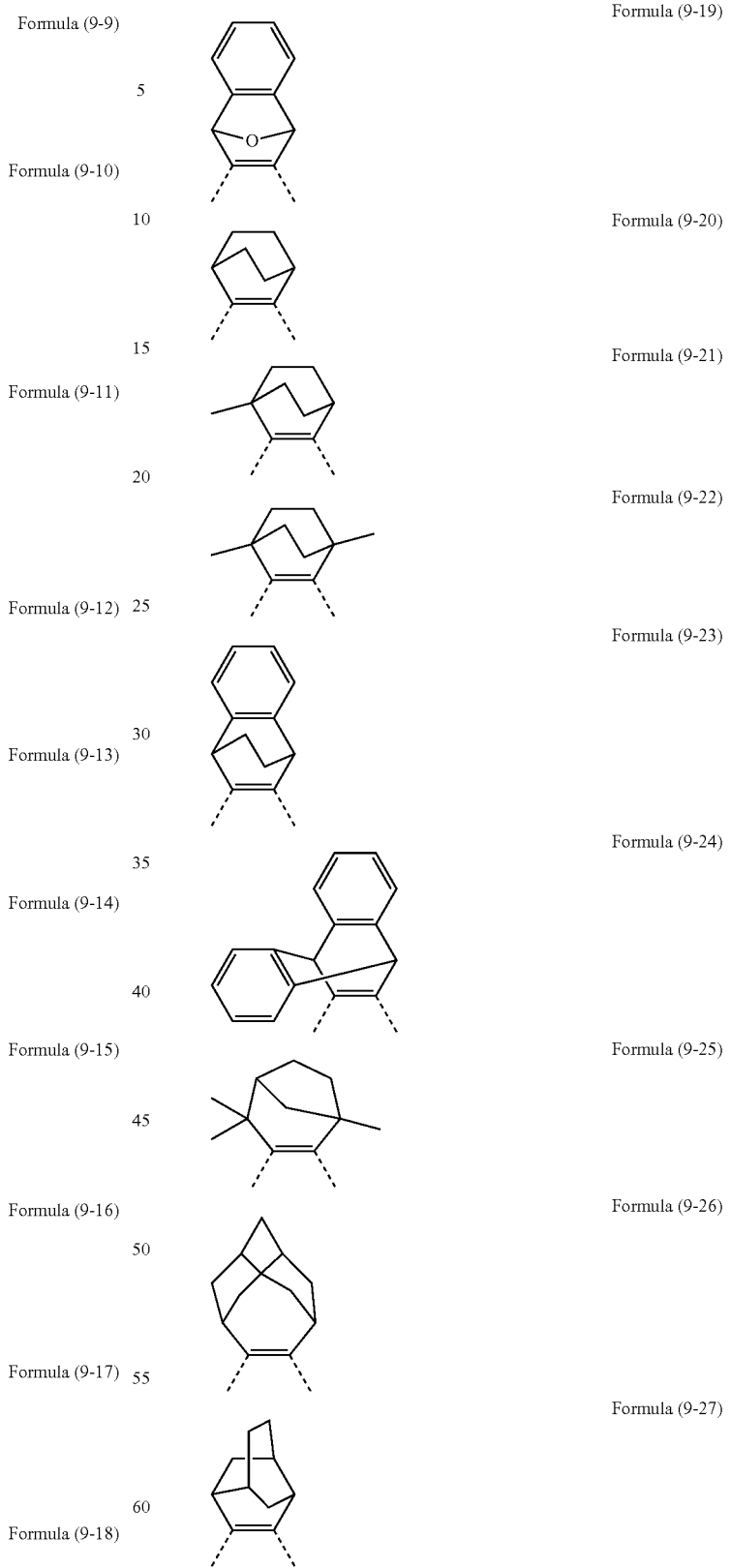
It may additionally be the case that, in the structure of the formulae (8), (8-A), (8-B), (8-C), (9), (9-A), (10), (10-A), (11) and (11-A), the G group in is a 1,2-ethylene group which may be substituted by one or more $R^2$ radicals, where $R^2$ is preferably the same or different at each instance and is H or an alkyl group having 1 to 4 carbon atoms, or an ortho-arylene group which has 6 to 10 carbon atoms in the ring and may be substituted by one or more $R^2$ radicals, but is preferably unsubstituted, especially an ortho-phenylene group which may be substituted by one or more $R^2$ radicals, but is preferably unsubstituted.

In addition, it may be the case that, in the structure of the formulae (5) to (11), the $R^3$ radical is the same or different at each instance and is F, a straight-chain alkyl group having 1 to 10 carbon atoms or a branched or cyclic alkyl group having 3 to 20 carbon atoms, where one or more nonadjacent $CH_2$ groups in each case may be replaced by $R^2C=CR^2$ and one or more hydrogen atoms may be replaced by D or F, or an aromatic or heteroaromatic ring system which has 5 to 14 aromatic ring atoms and may be substituted in each case by one or more $R^2$ radicals; at the same time, two $R^3$ radicals bonded to the same carbon atom may together form an aliphatic or aromatic ring system and thus form a Spiro system; in addition, $R^3$ may form an aliphatic ring system with an adjacent R or $R^1$ radical.

In compounds having structures of the formulae (5) to (11), the $R^3$ radical may preferably be the same or different at each instance and may be F, a straight-chain alkyl group having 1 to 3 carbon atoms, especially methyl, or an aromatic or heteroaromatic ring system which has 5 to 12 aromatic ring atoms and may be substituted in each case by one or more $R^2$ radicals, but is preferably unsubstituted; at the same time, two $R^3$ radicals bonded to the same carbon atom may together form an aliphatic or aromatic ring system and thus form a spiro system; in addition, $R^3$ may form an aliphatic ring system with an adjacent R or $R^1$ radical.

Preferably, not more than three X symbols in the above-detailed formula (1) and in the preferred embodiments of this formula are N, more preferably not more than two X symbols in formula (1) are N, and most preferably, not more than one X symbol in formula (1) is N. Especially preferably, all X symbols are CR in structures of the formula (1).

More preferably, it may be the case that the compounds have at least two ring structures of the formulae (5) to (11).

Especially preferred compounds are those having structures of the formula $CyG(CyH)_n$ where CyG and CyH together in each case form a ring and the symbols and indices are as follows:
n is 2 or 3 or 4, it being preferable that n is 2 or 3;
CyG is a structural element selected from the formulae

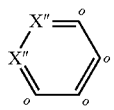
(CyG-1)

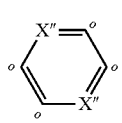
(CyG-2)

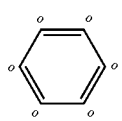
(CyG-3)

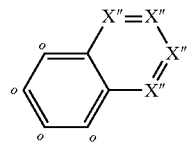
(CyG-4)

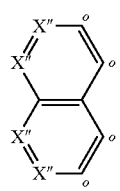
(CyG-5)

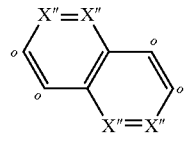
(CyG-6)

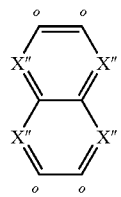
(CyG-7)

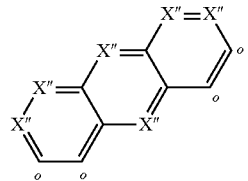
(CyG-8)

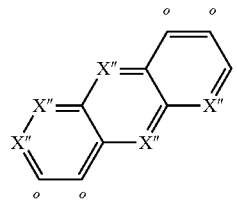
(CyG-9)

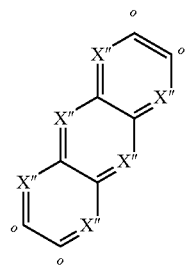
(CyG-10)

(CyG-11)
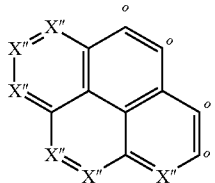
(CyG-12)
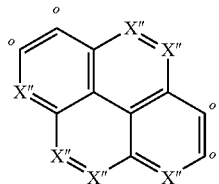
(CyG-13)
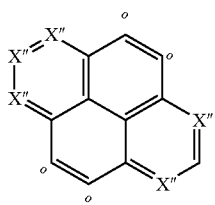
(CyG-14)
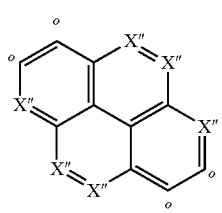
(CyG-15)
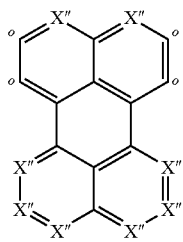
(CyG-16)
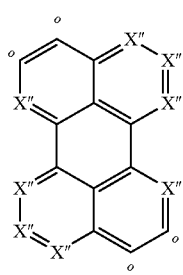
(CyG-17)
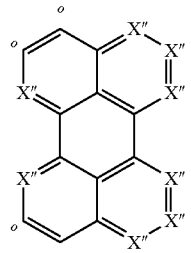
(CyG-18)
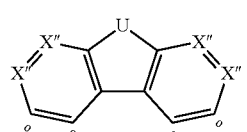
(CyG-19)
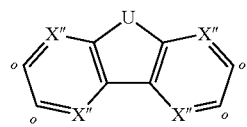
(CyG-20)
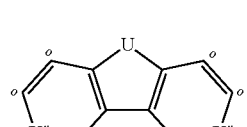
(CyG-21)
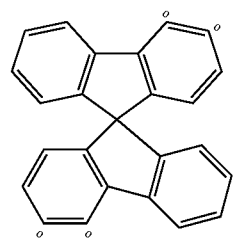
(CyG-22)
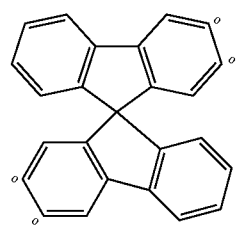
(CyG-23)
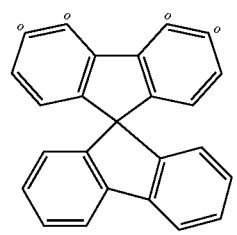

(CyG-24)
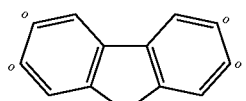

(CyG-25)
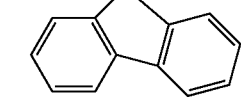

(CyG-26)
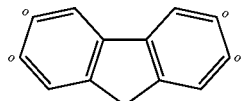

(CyG-27)
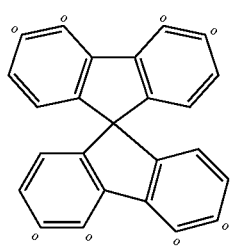

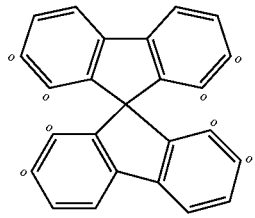

and CyH is at least one structural element of the following formula:

(CyH)
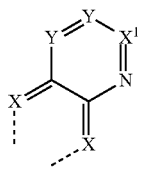

where the symbols Y, X, X" and $X^1$ used are as defined above, U is selected from O, S, C(R)$_2$, N(R), B(R), Si(R)$_2$, C=O, S=O, SO$_2$, P(R) and P(=O)R, the dotted lines in formulae CyH indicate the bonds to CyG, and CyH binds to CyG in each case at the positions indicated by "o" to form a ring.

Preferably not more than three X and X" symbols in CyG and/or CyH are N, more preferably not more than two X and X" symbols in CyG and/or CyH are N, and even more preferably not more than one X and X" symbol in CyG and/or CyH is N. Especially preferably, all X symbols are CR and all X" symbols are $CR^1$ in structures of the formula CyG(CyH)$_n$.

It is clear that regioisomers are also encompassed in the present case, which arise from the way in which the CyH ring is fused on.

The heterocyclic compounds of the invention comprising structures of the formula (1) may also be chiral according to the structure. This is the case especially when they contain substituents, for example alkyl, alkoxy or aralkyl groups, having one or more stereocenters. Since the base structure of the heterocyclic compound may also be a chiral structure, the formation of diastereomers and multiple pairs of enantiomers is possible. In that case, the compounds of the invention include both the mixtures of the different diastereomers or the corresponding racemates and the individual isolated diastereomers or enantiomers.

Preferably, the compound may be in the form of an enantiomer mixture, more preferably of a diastereomer mixture. As a result, it is unexpectedly possible to enhance the properties of electronic devices obtainable using the compounds of the invention. These properties especially include the lifetime of the devices.

Preferred embodiments of compounds of the invention are detailed specifically in the examples, these compounds being usable alone or in combination with further compounds for all purposes of the invention. In a particular embodiment of the present invention, compounds of the formulae

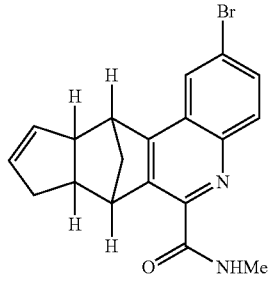

1451566-65-6
1451566-62-3

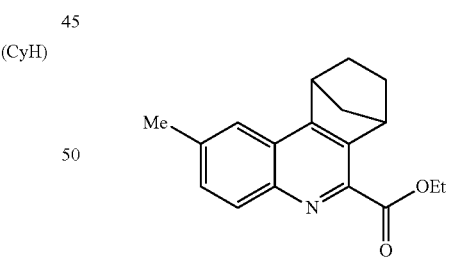

1441062-61-8

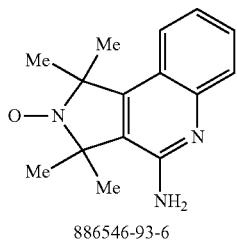

886546-93-6

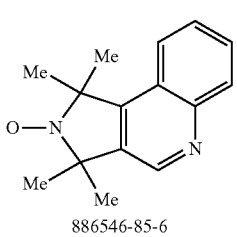

886546-85-6

-continued

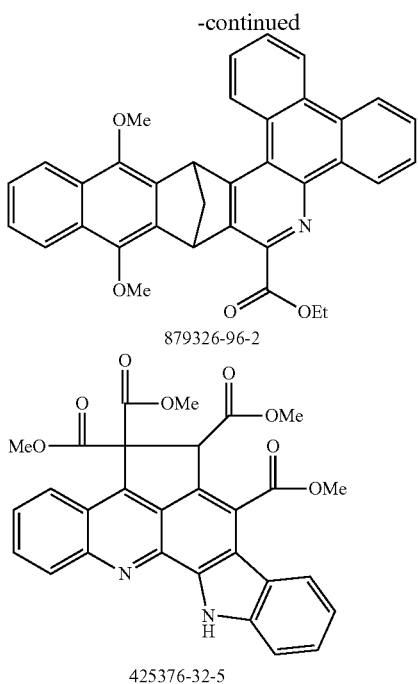

are excluded from protection and are preferably not covered by formula (1).

It may additionally be the case that the compound of formula (1) does not have any N-oxide, ester or amide groups.

Provided that the conditions specified in claim 1 are complied with, the abovementioned preferred embodiments can be combined with one another as desired. In a particularly preferred embodiment of the invention, the abovementioned preferred embodiments apply simultaneously.

The compounds of the invention are preparable in principle by various processes. However, the processes described hereinafter have been found to be particularly suitable.

Therefore, the present invention further provides a process for preparing the compounds comprising structures of formula (1) in which at least one primary arylamine is reacted with at least one β-keto vinyl alcohol (or the tautomeric β-keto aldehyde) to give a β-keto enamine compound which is subsequently cyclized.

The principles of the preparation processes detailed above are known in principle from the literature for similar compounds and can be adapted easily by the person skilled in the art to the preparation of the compounds of the invention. Further information can be found in the examples.

It is possible by these processes, if necessary followed by purification, for example recrystallization or sublimation, to obtain the compounds of the invention comprising structures of formula (1) in high purity, preferably more than 99% (determined by means of $^1$H NMR and/or HPLC).

The compounds of the invention may also have suitable substituents, for example by relatively long alkyl groups (about 4 to 20 carbon atoms), especially branched alkyl groups, or optionally substituted aryl groups, for example xylyl, mesityl or branched terphenyl or quaterphenyl groups, which bring about solubility in standard organic solvents, for example toluene or xylene, at room temperature in a sufficient concentration soluble, in order to be able to process the complexes from solution. These soluble compounds are of particularly good suitability for processing from solution, for example by printing methods. In addition, it should be emphasized that the compounds of the invention comprising at least one structure of the formula (1) already have enhanced solubility in these solvents.

The following overview contains some examples of compounds of the invention:

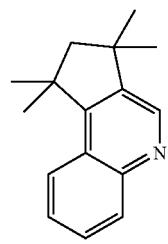

Formula (E-1)

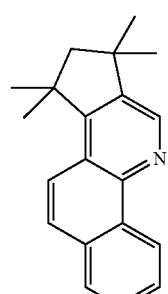

Formula (E-2)

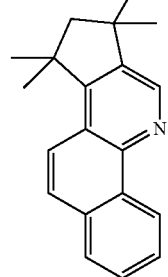

Formula (E-3)

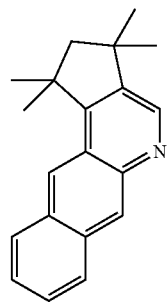

Formula (E-4)

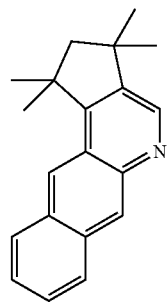

Formula (E-5)

-continued
Formula (E-6)
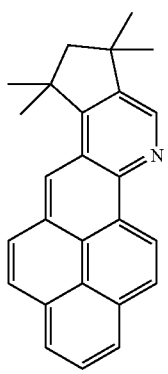
Formula (E-7)
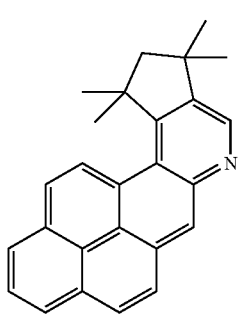
Formula (E-8)
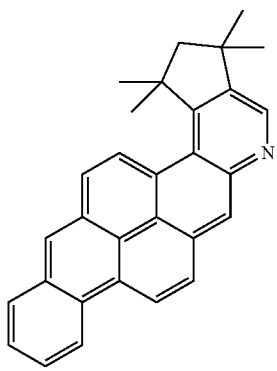
Formula (E-9)
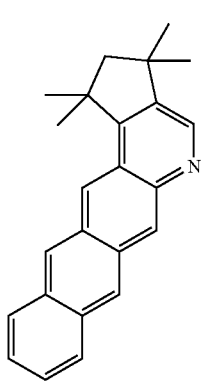
Formula (E-10)
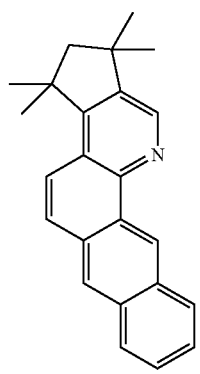
Formula (E-11)
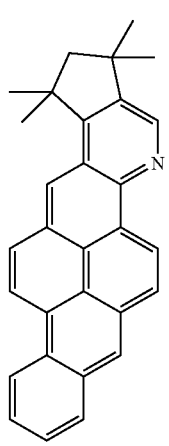
Formula (E-12)
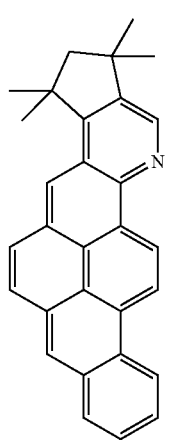
Formula (E-13)
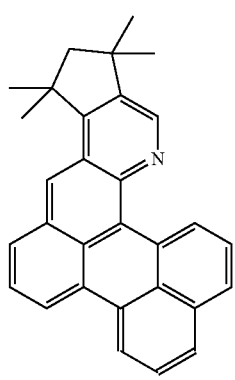

Formula (E-14)
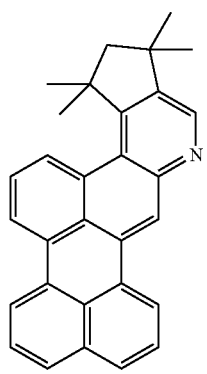
Formula (E-15)
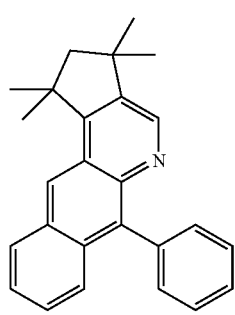
Formula (E-16)
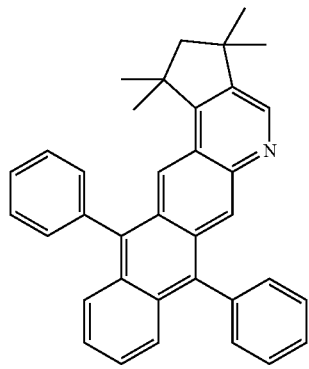
Formula (E-17)
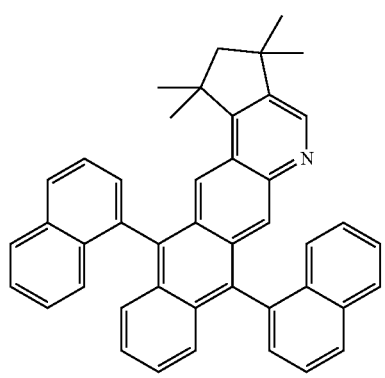
Formula (E-18)
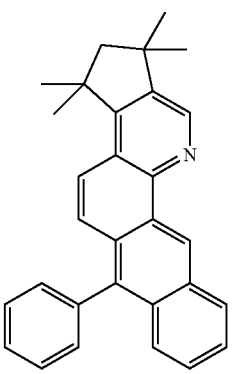
Formula (E-19)
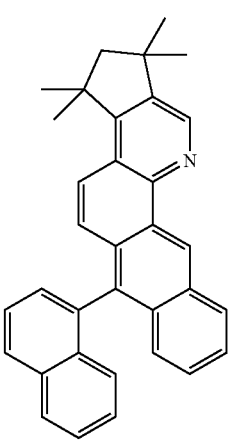
Formula (E-20)
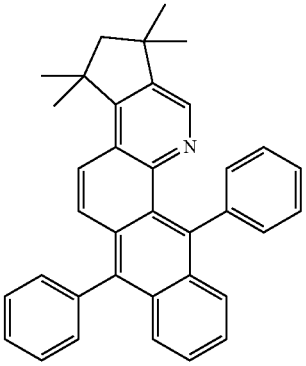
Formula (E-21)
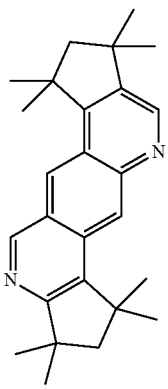

Formula (E-22)
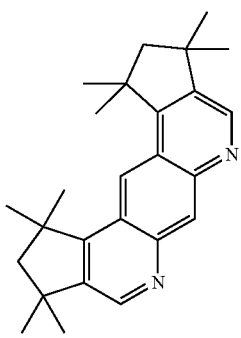
Formula (E-23)
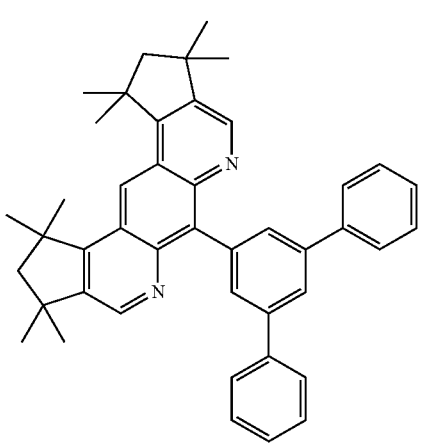
Formula (E-24)
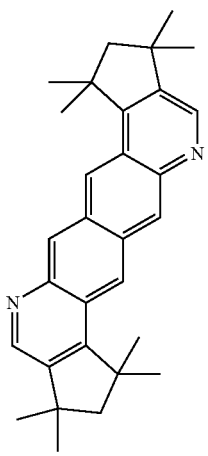
Formula (E-25)
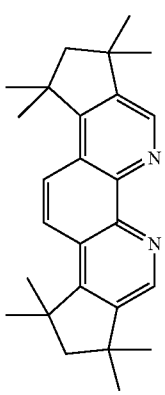
Formula (E-26)
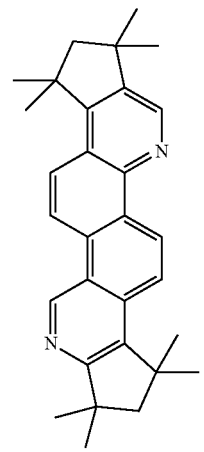
Formula (E-27)
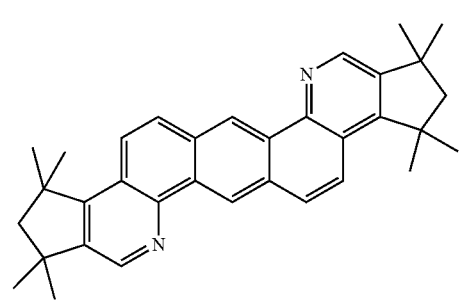
Formula (E-28)
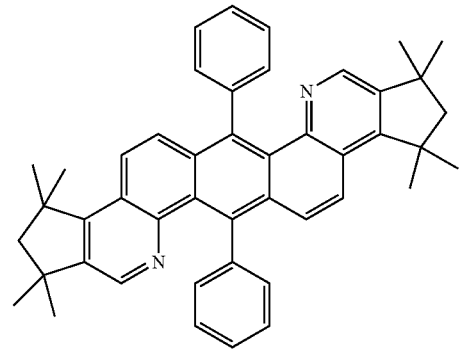
Formula (E-29)
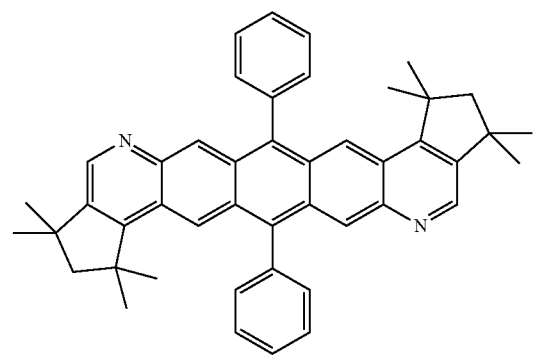

Formula (E-30)

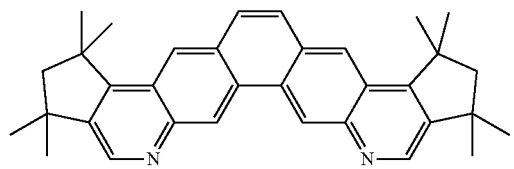

Formula (E-31)

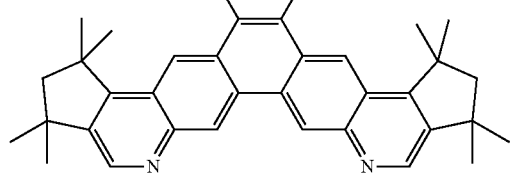

Formula (E-32)

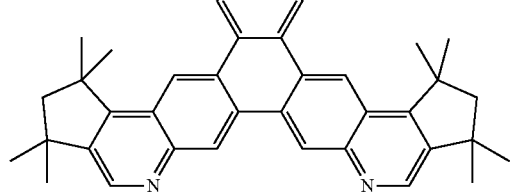

Formula (E-33)

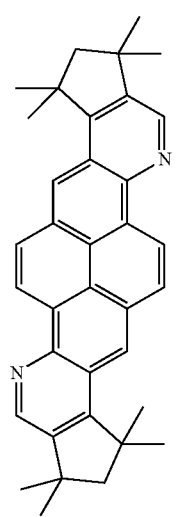

Formula (E-34)

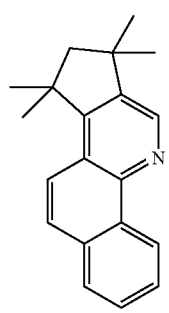

Formula (E-35)

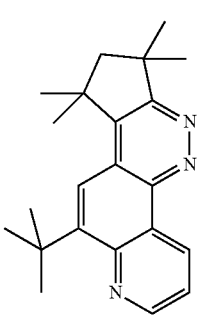

Formula (E-36)

Formula (E-37)

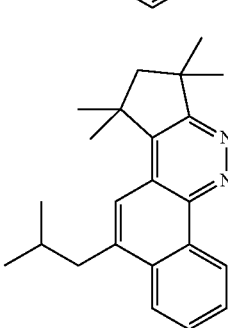

Formula (E-38)

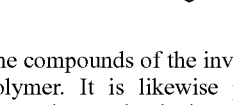

The compounds of the invention may also be mixed with a polymer. It is likewise possible to incorporate these compounds covalently into a polymer. This is especially possible with compounds substituted by reactive leaving groups such as bromine, iodine, chlorine, boronic acid or boronic ester, or by reactive polymerizable groups such as olefins or oxetanes. These may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The compounds of the invention and polymers may be used in the form of a crosslinked or uncrosslinked layer.

The invention therefore further provides oligomers, polymers or dendrimers containing one or more of the above-detailed structures of the formula (1) or compounds of the invention, wherein one or more bonds of compounds of the invention or of the structures of the formula (1) to the polymer, oligomer or dendrimer are present. According to the linkage of the structures of the formula (1) or of the compounds, these therefore form a side chain of the oligomer or polymer or are bonded within the main chain. The polymers, oligomers or dendrimers may be conjugated, partly conjugated or nonconjugated. The oligomers or polymers may be linear, branched or dendritic. For the repeat units of the compounds of the invention in oligomers, dendrimers and polymers, the same preferences apply as described above.

For preparation of the oligomers or polymers, the monomers of the invention are homopolymerized or copolymerized with further monomers. Preference is given to copolymers wherein the units of formula (1) or the above-recited preferred embodiments are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/022026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units.

In addition, the present compounds may have a relatively low molecular weight. The present invention accordingly further provides a compound having a molecular weight of preferably not more than 10 000 g/mol, more preferably not more than 5000 g/mol and especially preferably not more than 3000 g/mol.

In addition, it is a feature of preferred compounds that they are sublimable. These compounds generally have a molar mass of less than about 1200 g/mol.

Additionally of particular interest are compounds of the invention which feature a high glass transition temperature. In this connection, preference is given especially to compounds of the invention comprising structures of the general formula (1) having a glass transition temperature of at least 70° C., more preferably of at least 110° C., even more preferably of at least 125° C. and especially preferably of at least 150° C., determined in accordance with DIN 51005.

The present invention still further provides a formulation comprising a compound of the invention or an oligomer, polymer or dendrimer of the invention and at least one further compound. The further compound may preferably be a solvent. The further compound may alternatively be a further organic or inorganic compound which is likewise used in the electronic device, for example a matrix material. This further compound may also be polymeric.

Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention still further provides a composition comprising a compound of the invention and at least one further organic functional material. Functional materials are generally the organic or inorganic materials introduced between the anode and cathode. Preferably, the organic functional material is selected from the group consisting of fluorescent emitters, phosphorescent emitters, host materials, matrix materials, electron transport materials, electron injection materials, hole conductor materials, hole injection materials, n-dopants, wide band gap materials, electron blocker materials and hole blocker materials.

The present invention therefore also relates to a composition comprising at least one compound comprising structures of formula (1) and at least one further matrix material. According to a particular aspect of the present invention, the further matrix material has hole-transporting properties.

The present invention further provides a composition comprising at least one compound comprising at least one structure of formula (1) and at least one wide band gap material, a wide band gap material being understood to mean a material in the sense of the disclosure of U.S. Pat. No. 7,294,849. These systems exhibit particularly advantageous performance data in electroluminescent devices.

Preferably, the additional compound may have a band gap of 2.5 eV or more, preferably 3.0 eV or more, very preferably of 3.5 eV or more. One way of calculating the band gap is via the energy levels of the highest occupied molecular orbital (HOMO) and the lowest unoccupied molecular orbital (LUMO).

Molecular orbitals, especially also the highest occupied molecular orbital (HOMO) and the lowest unoccupied molecular orbital (LUMO), the energy levels thereof and the energy of the lowest triplet state $T_1$ and that of the lowest excited singlet state $S_1$ of the materials are determined via quantum-chemical calculations. For calculation of organic substances without metals, an optimization of geometry is first conducted by the "Ground State/Semi-empirical/Default Spin/AM1/Charge 0/Spin Singlet" method. Subsequently, an energy calculation is effected on the basis of the optimized geometry. This is done using the "TD-SCF/DFT/Default Spin/B3PW91" method with the "6-31G(d)" basis set (charge 0, spin singlet). For metal-containing compounds, the geometry is optimized via the "Ground State/Hartree-Fock/Default Spin/LanL2 MB/Charge 0/Spin Singlet" method. The energy calculation is effected analogously to the above-described method for the organic substances, except that the "LanL2DZ" basis set is used for the metal atom and the "6-31G(d)" basis set for the ligands. The HOMO energy level HEh or LUMO energy level LEh is obtained from the energy calculation in Hartree units. This is used to determine the HOMO and LUMO energy levels in electron volts, calibrated by cyclic voltammetry measurements, as follows:

HOMO(eV)=((HEh*27.212)−0.9899)/1.1206

LUMO(eV)=((LEh*27.212)−2.0041)/1.385

These values are to be regarded as HOMO and LUMO energy levels of the materials in the context of this application.

The lowest triplet state $T_1$ is defined as the energy of the triplet state having the lowest energy, which is apparent from the quantum-chemical calculation described.

The lowest excited singlet state $S_1$ is defined as the energy of the excited singlet state having the lowest energy, which is apparent from the quantum-chemical calculation described.

The method described herein is independent of the software package used and always gives the same results. Examples of frequently utilized programs for this purpose are "Gaussian09W" (Gaussian Inc.) and Q-Chem 4.1 (Q-Chem, Inc.).

The present invention also relates to a composition comprising at least one compound comprising structures of formula (1) and at least one phosphorescent emitter, the term "phosphorescent emitter" also being understood to mean phosphorescent dopants.

The term "phosphorescent dopants" typically encompasses compounds where the emission of light is effected through a spin-forbidden transition, for example a transition from an excited triplet state or a state having a higher spin quantum number, for example a quintet state.

Suitable phosphorescent dopants are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent dopants, compounds containing copper, molybdenum, tungsten, rhenium, ruthenium, osmium, rhodium, iridium, palladium, platinum, silver, gold or europium, especially compounds containing iridium, platinum or copper.

In the context of the present application, all luminescent iridium, platinum or copper complexes are considered to be phosphorescent compounds. Examples of phosphorescent dopants are adduced in a section which follows.

A dopant in a system comprising a matrix material and a dopant is understood to mean that component having the smaller proportion in the mixture. Correspondingly, a matrix material in a system comprising a matrix material and a dopant is understood to mean that component having the greater proportion in the mixture.

Preferred phosphorescent dopants for use in mixed matrix systems are the preferred phosphorescent dopants specified hereinafter.

Examples of phosphorescent dopants can be found in applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used for phosphorescent OLEDs according to the prior art and as known to those skilled in the art in the field of organic electroluminescent devices are suitable for use in the inventive devices.

Explicit examples of phosphorescent dopants are adduced in the following table:

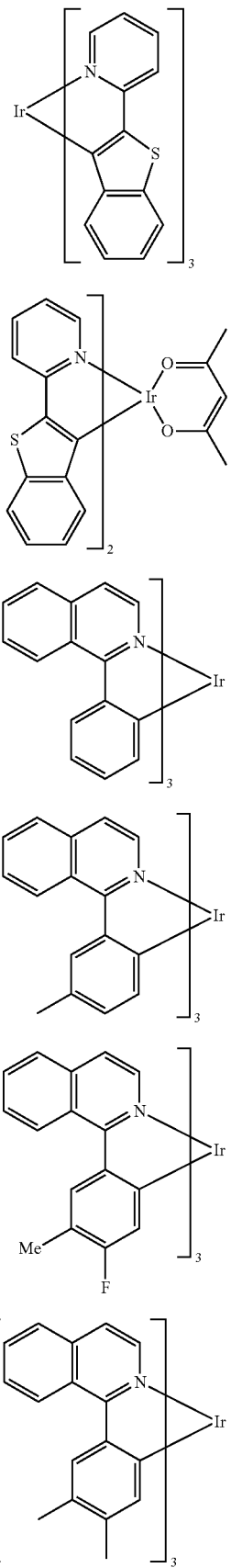

-continued
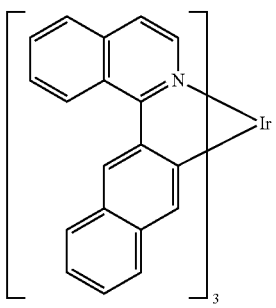
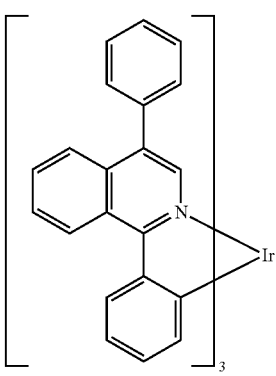
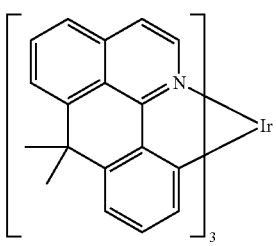
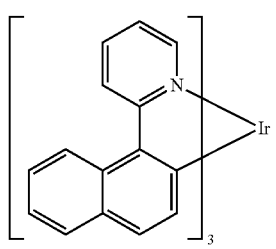
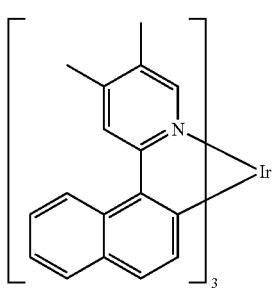
-continued
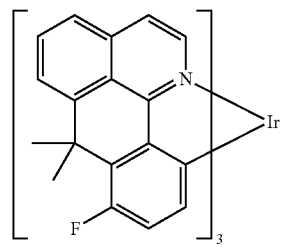
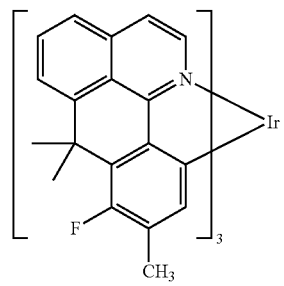
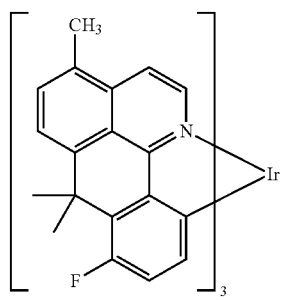
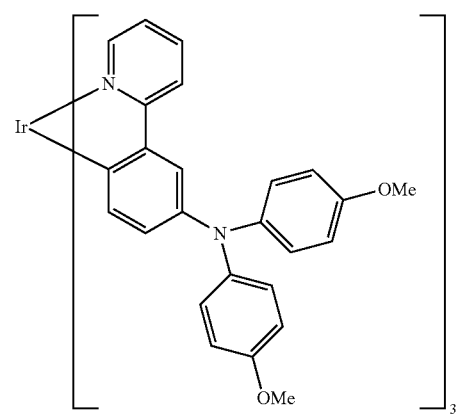
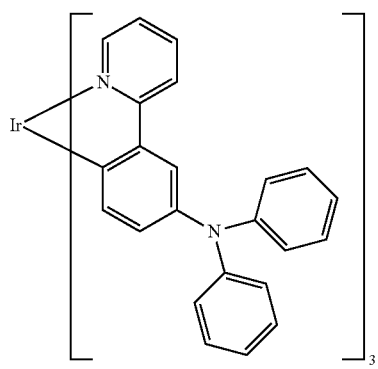

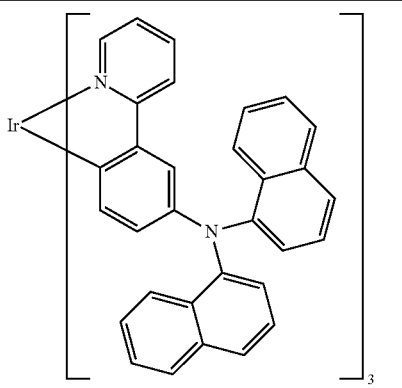
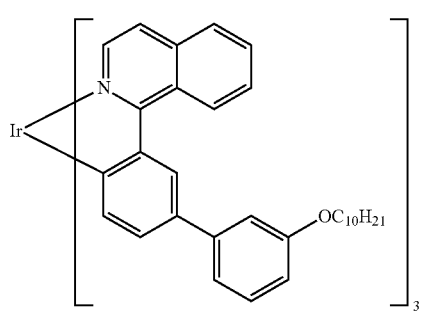
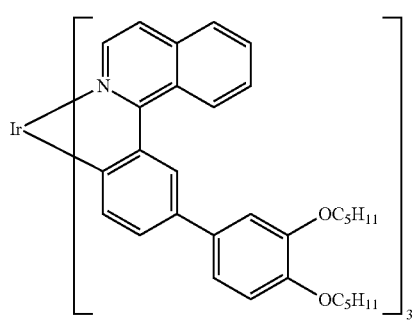
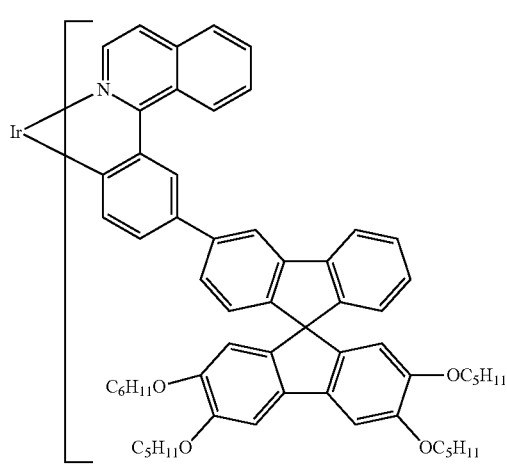
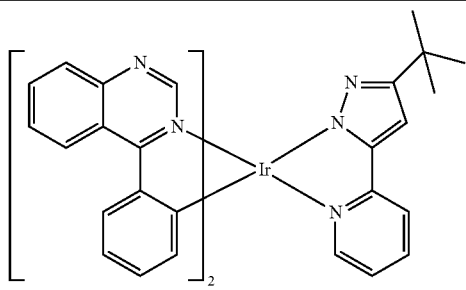
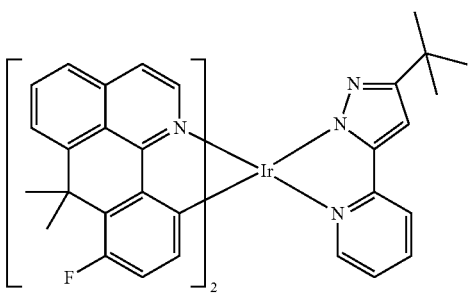
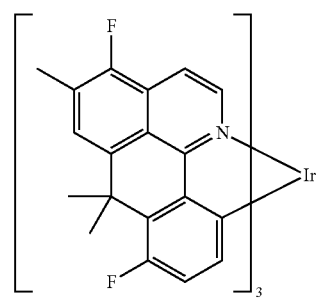
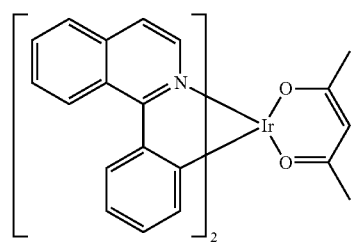
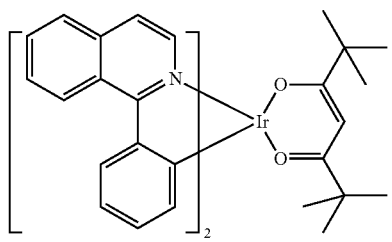
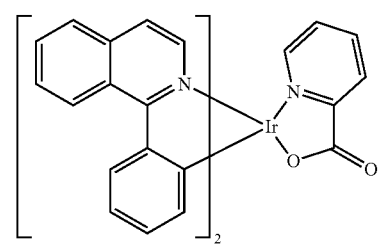

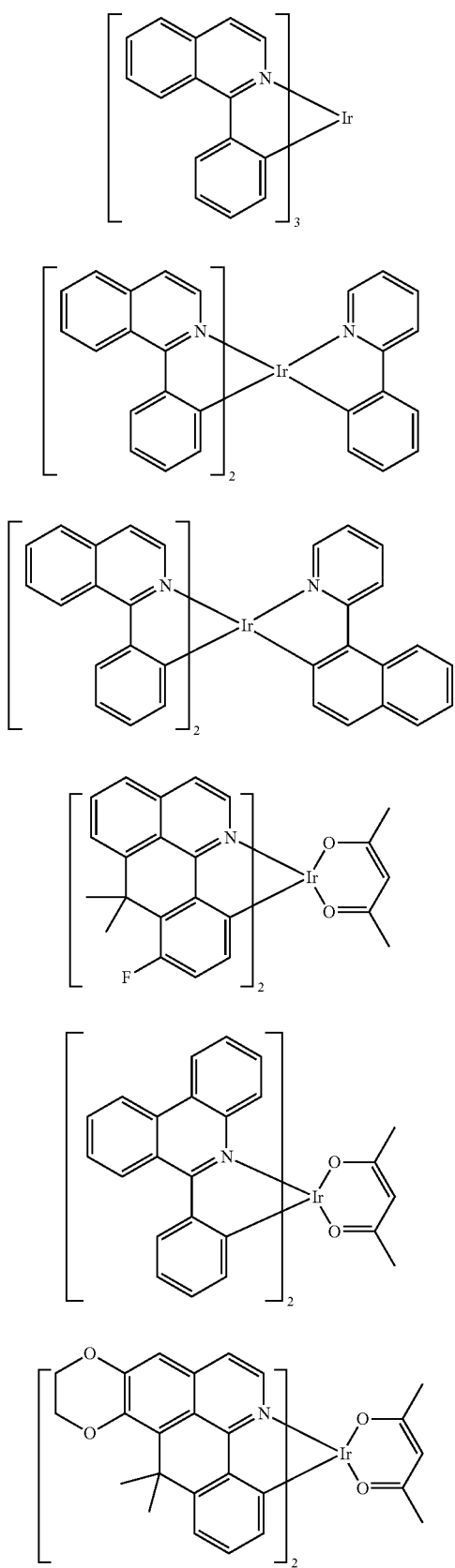
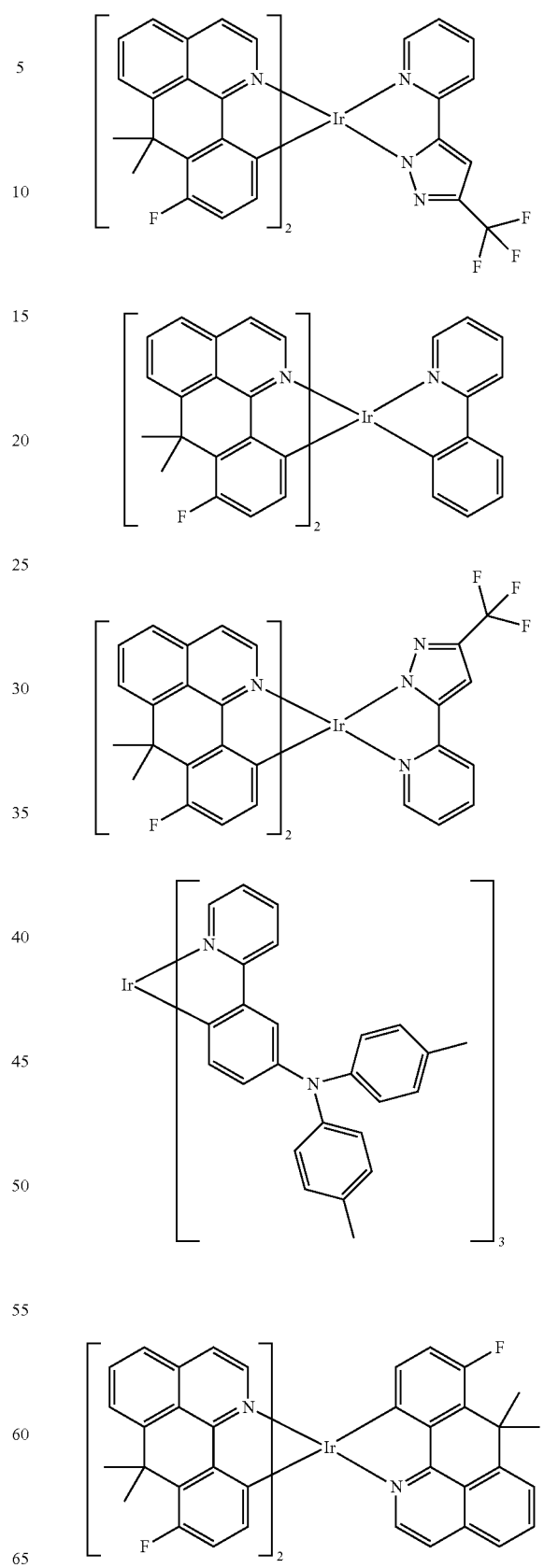

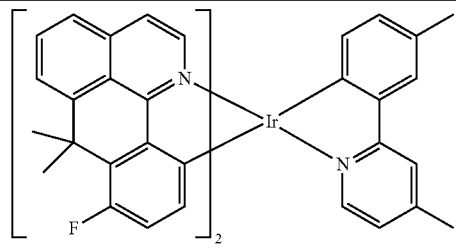
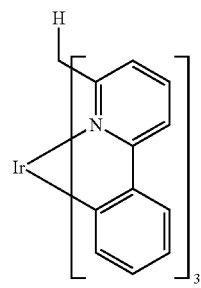
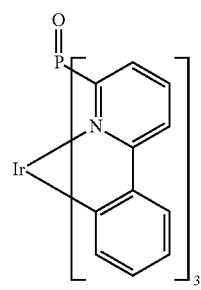
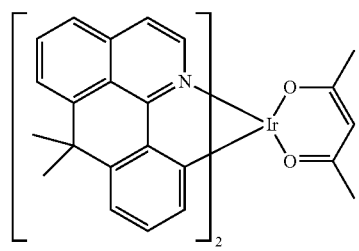
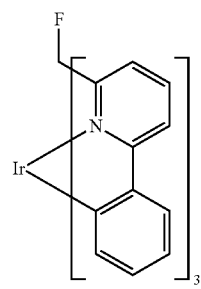
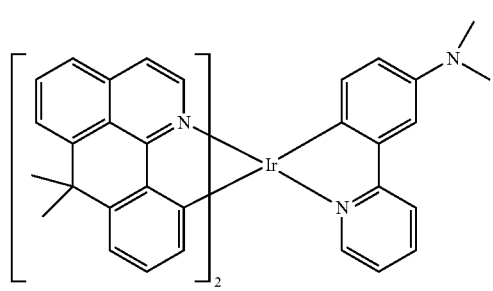
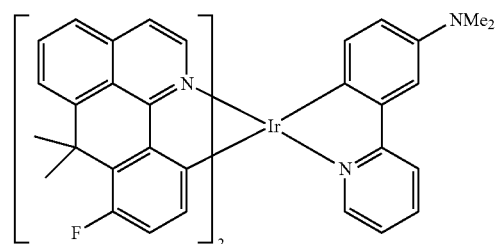
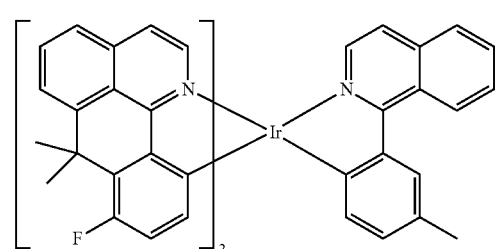
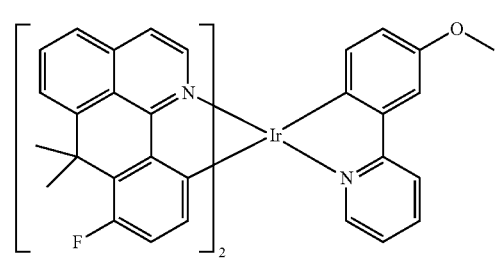
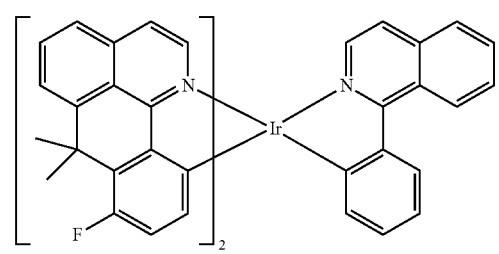
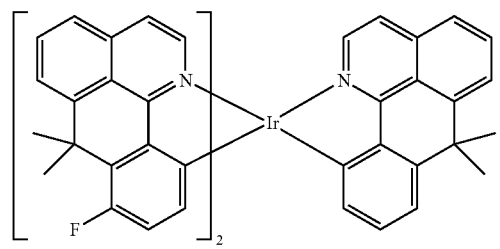
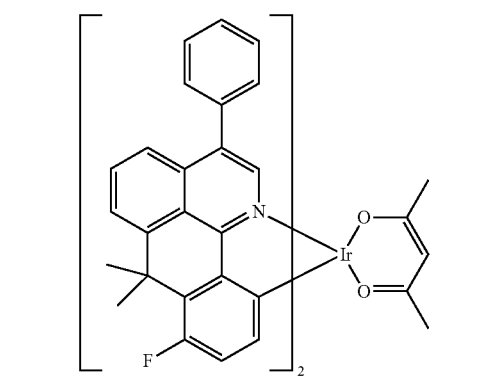

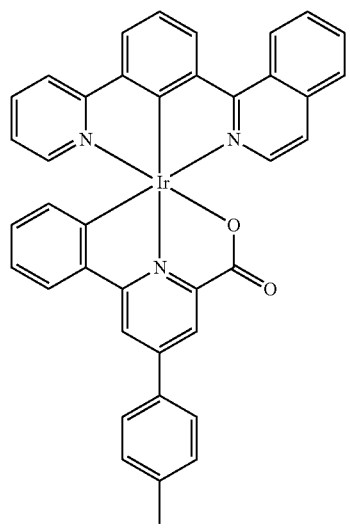
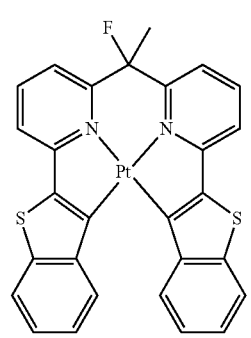
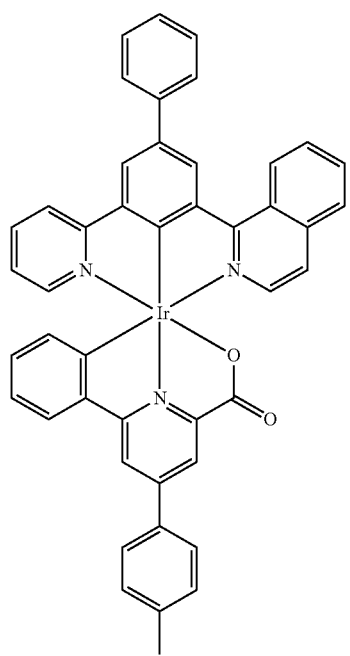
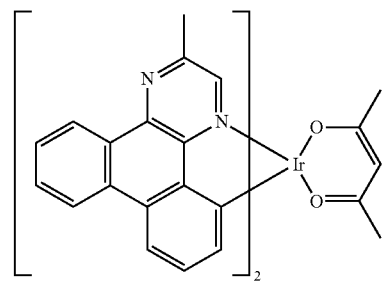
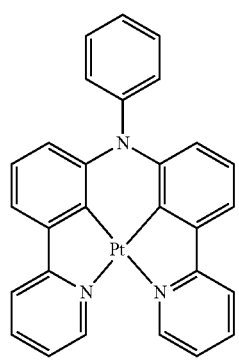
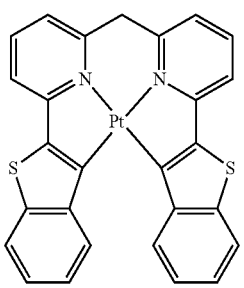
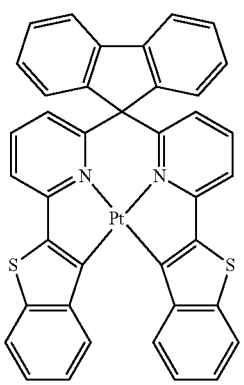
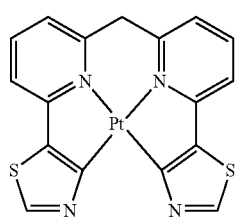

-continued
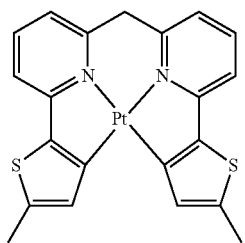
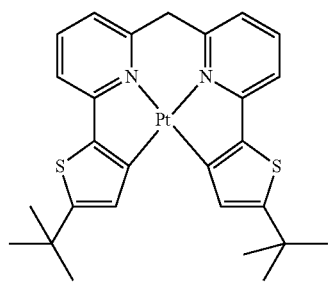
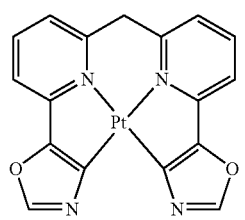
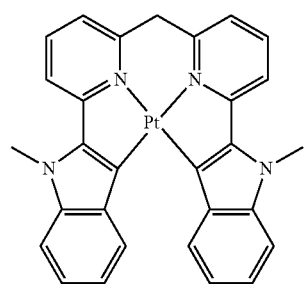
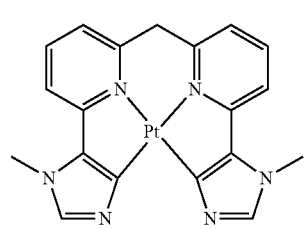
-continued
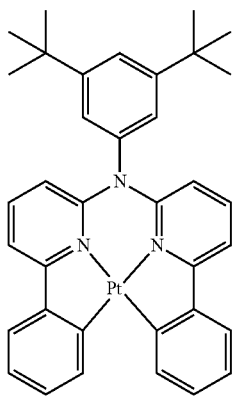
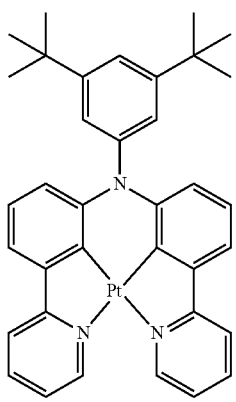
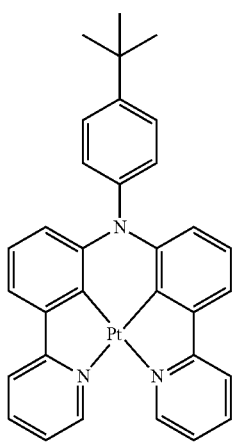
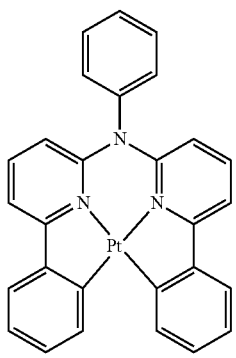

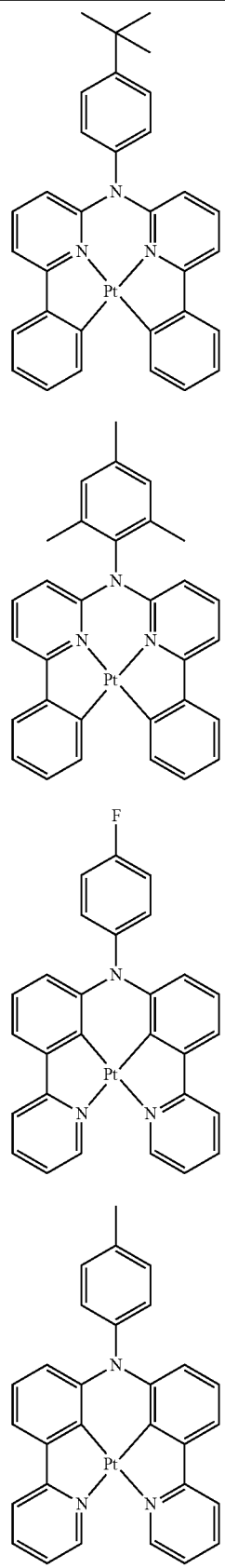
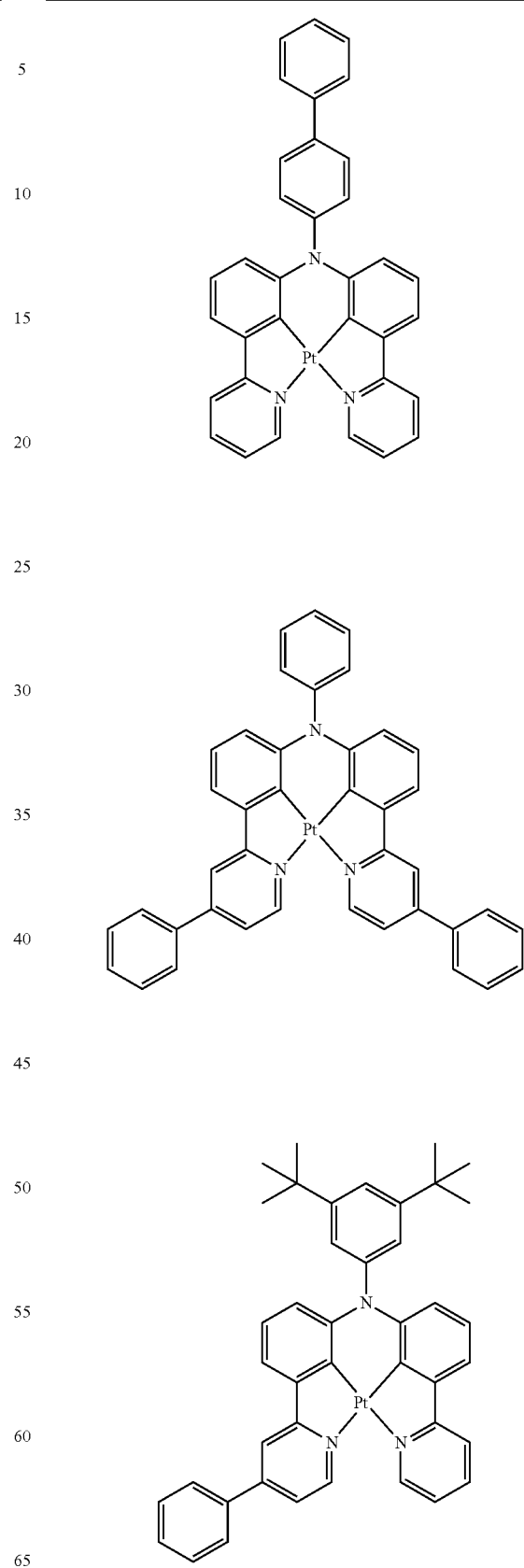

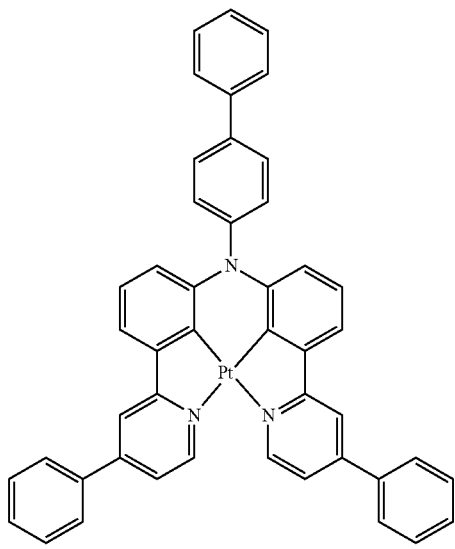
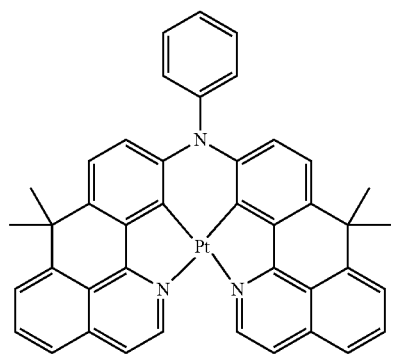
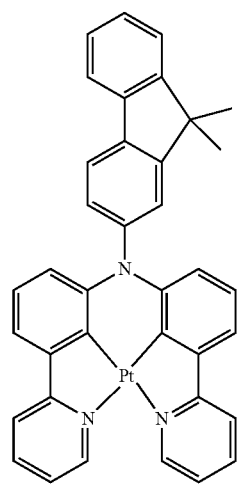
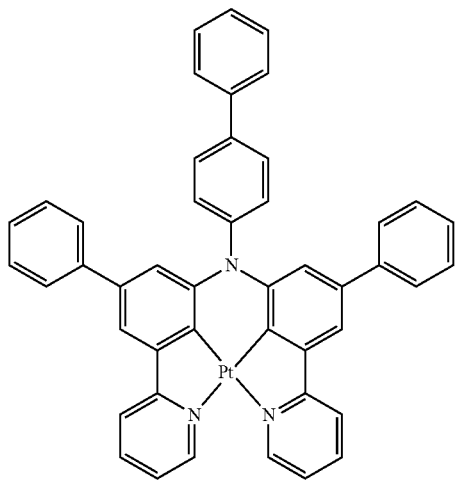
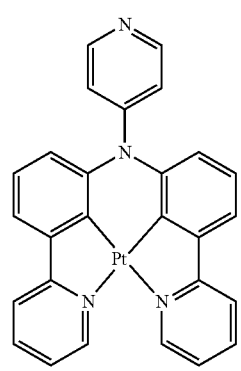
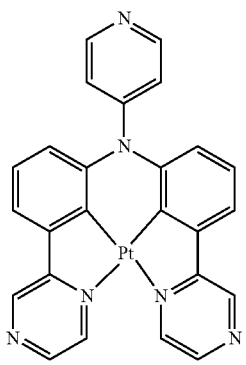
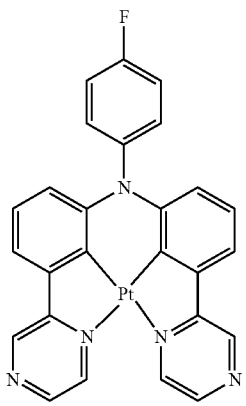

63
-continued
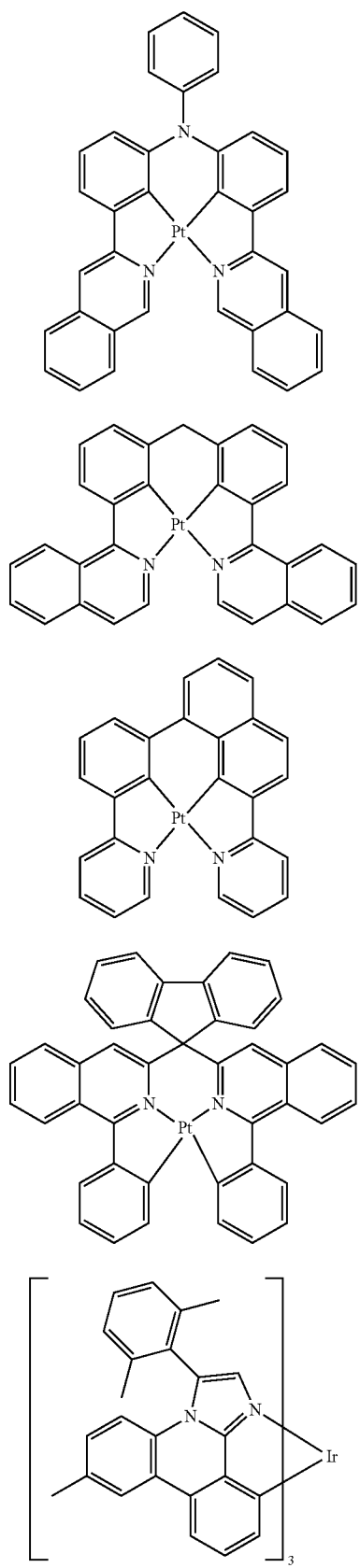
64
-continued
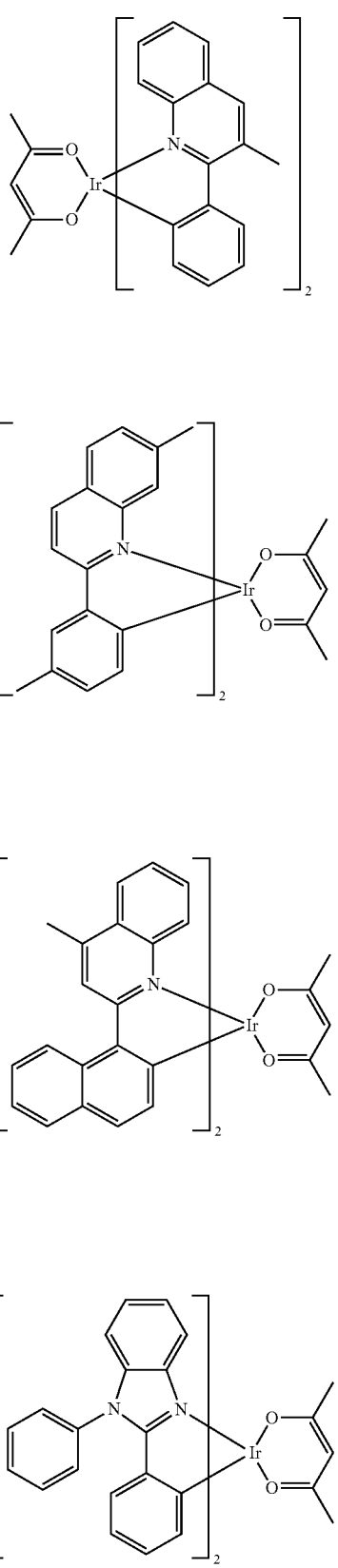

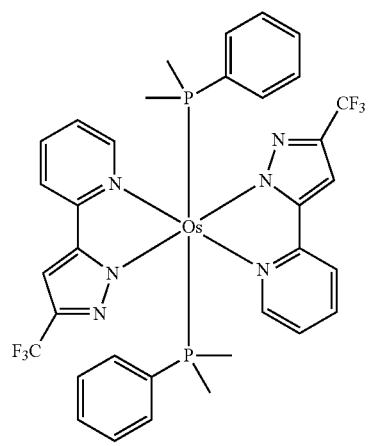
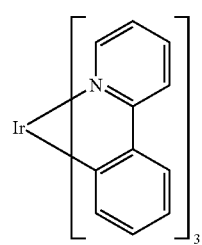
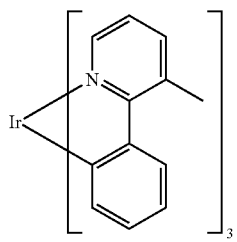
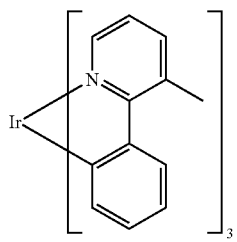
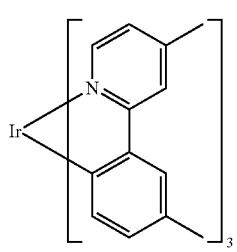
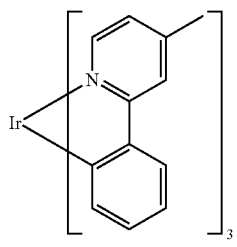
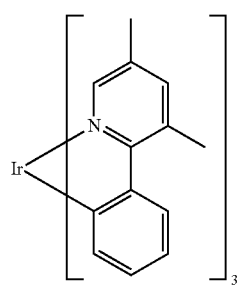
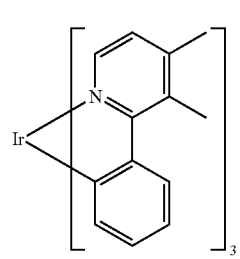
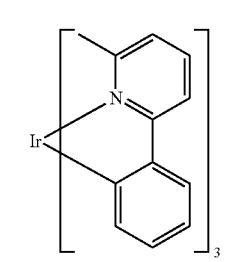
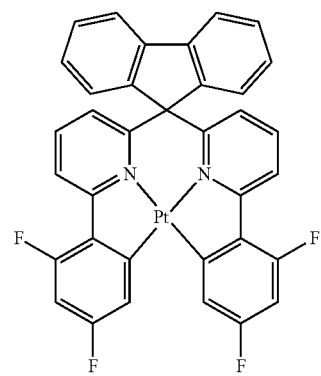
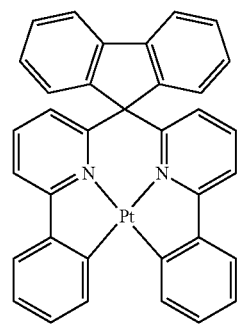

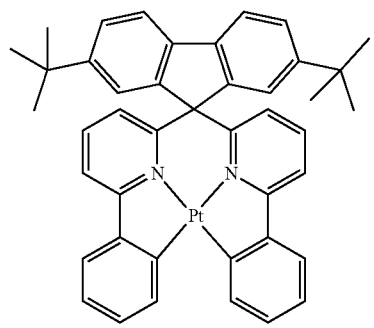
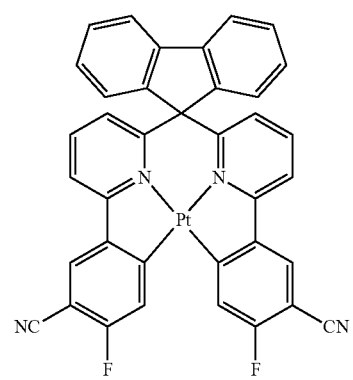
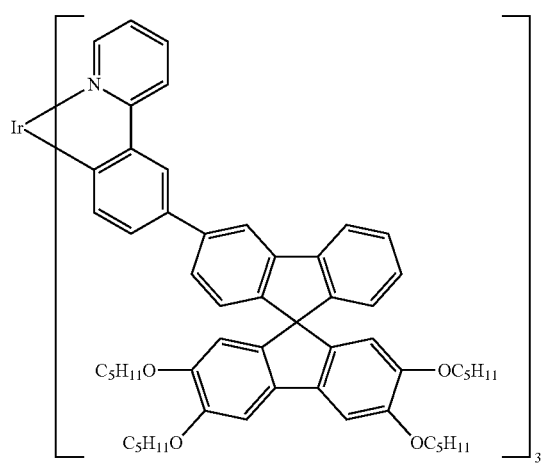
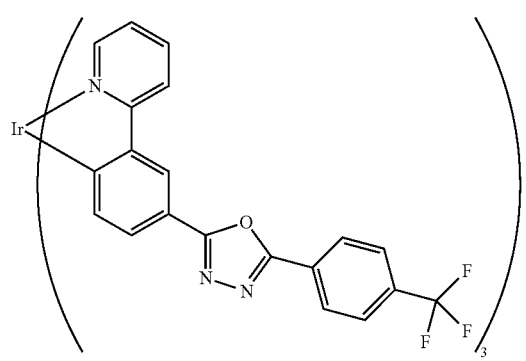
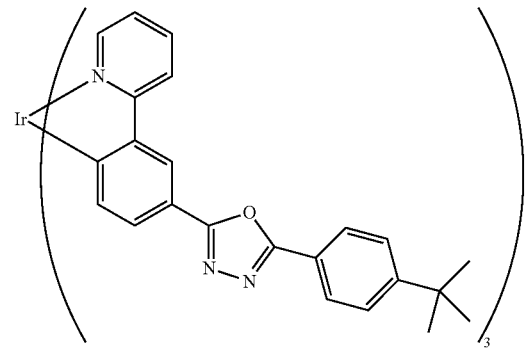
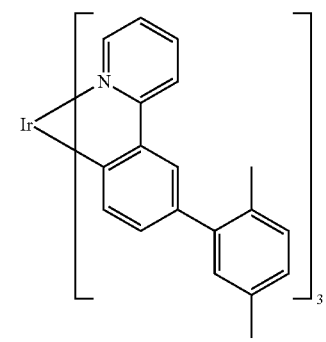
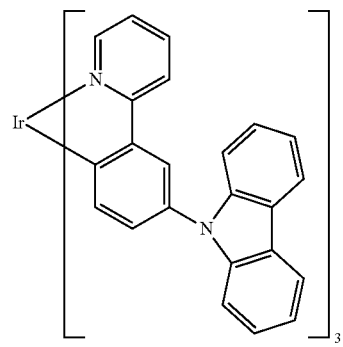
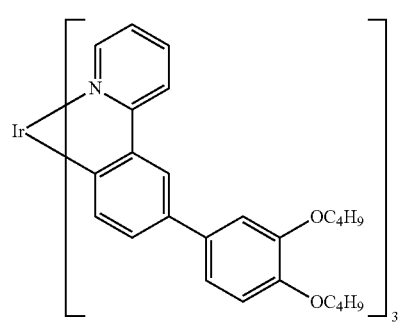

69
-continued
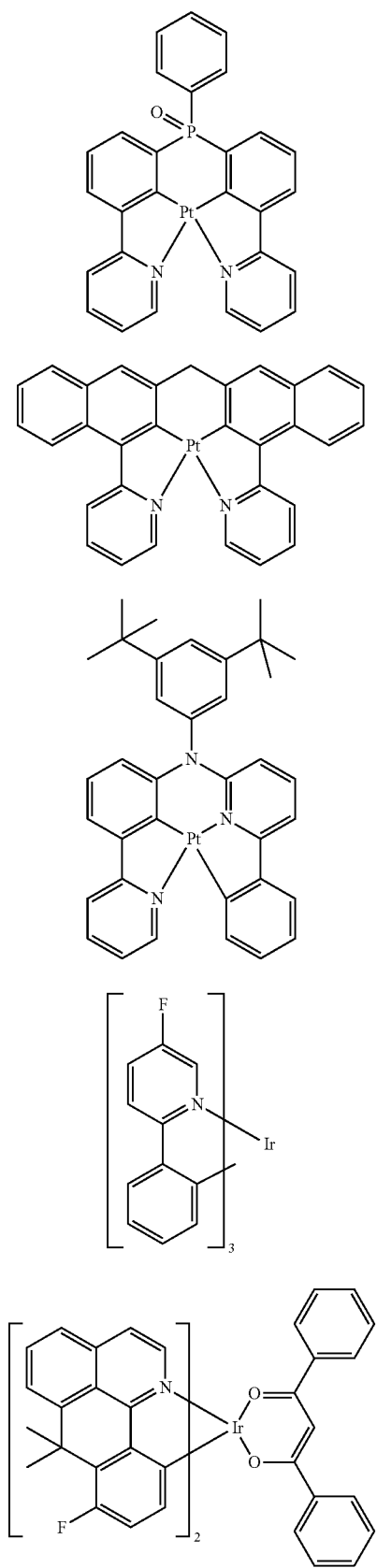
70
-continued
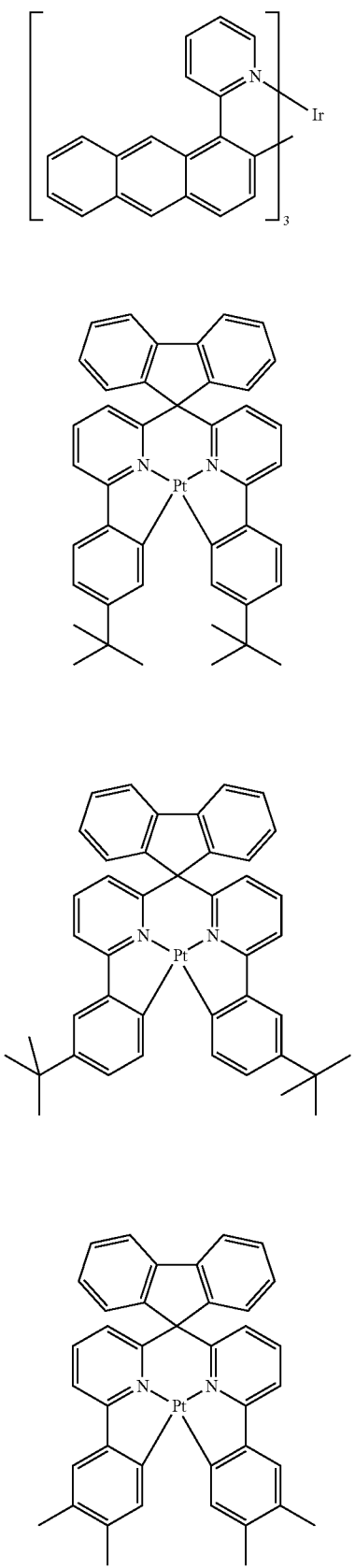

-continued
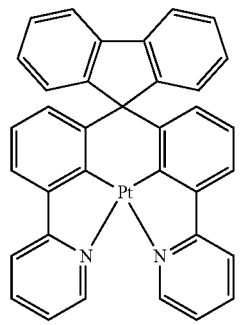
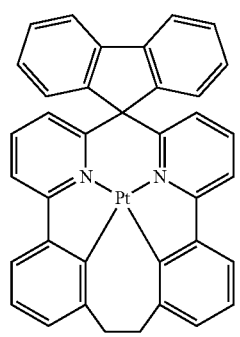
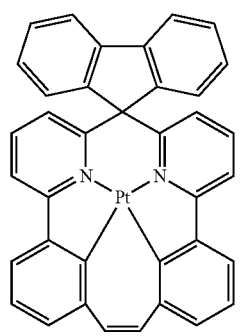
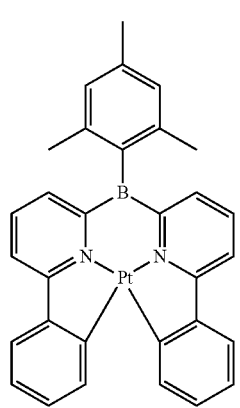
-continued
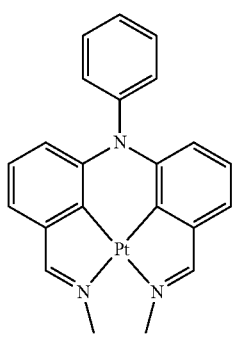
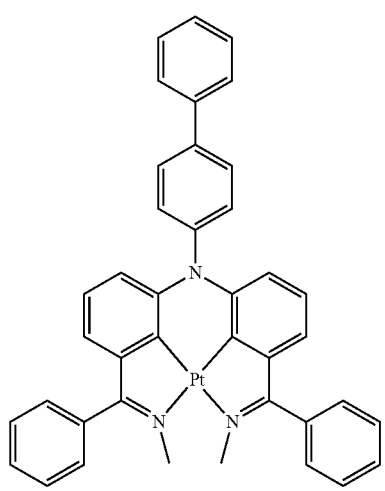
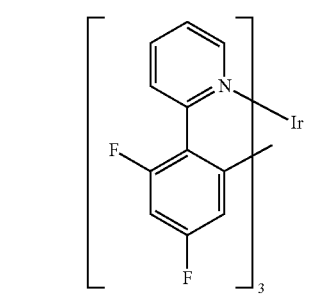
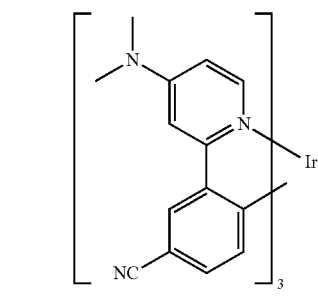

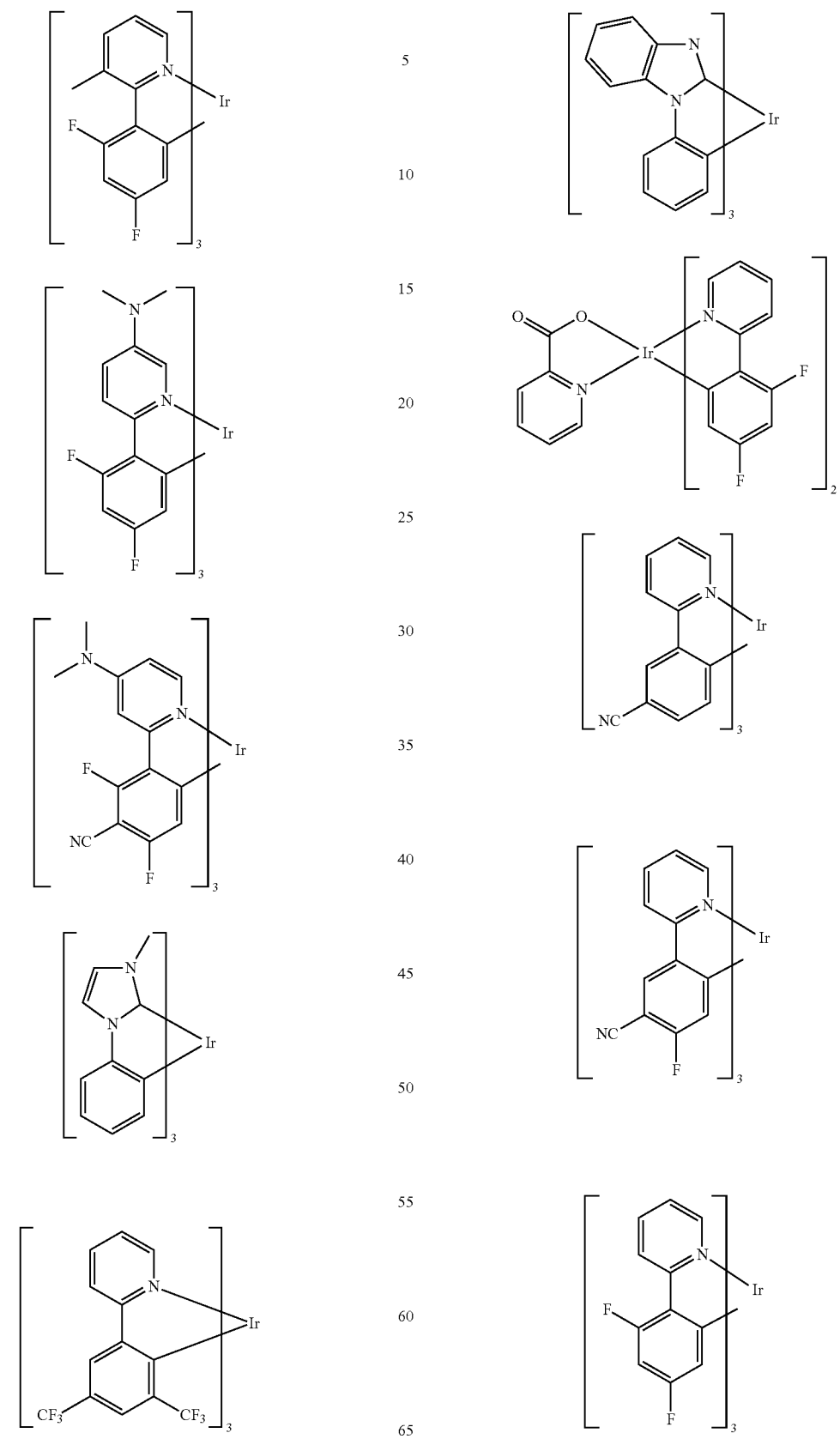

-continued
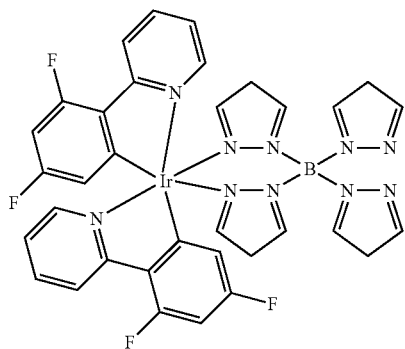
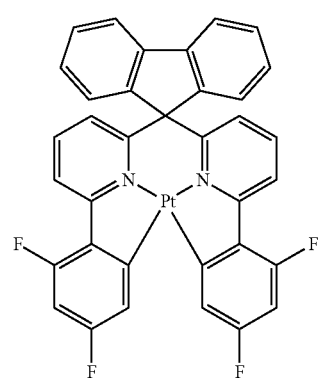
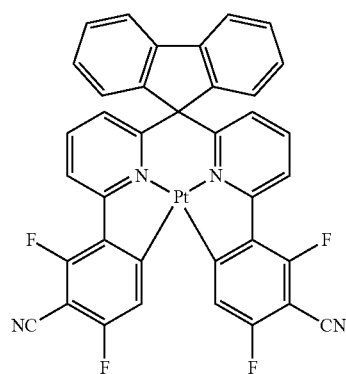
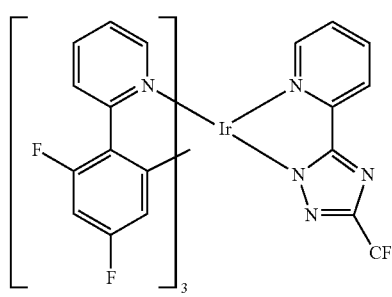
-continued
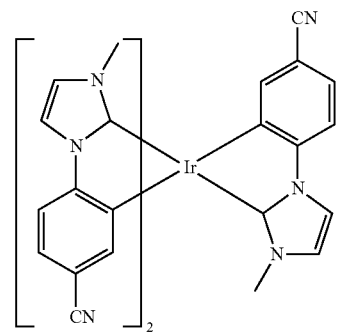
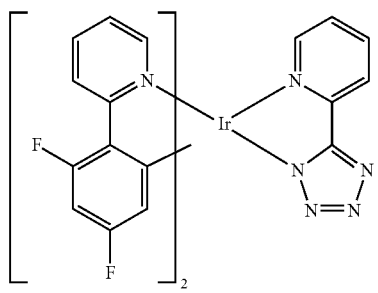
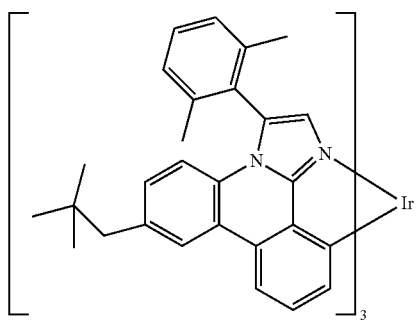
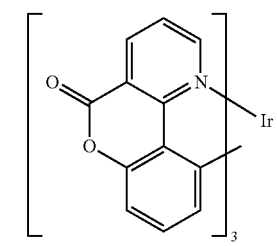
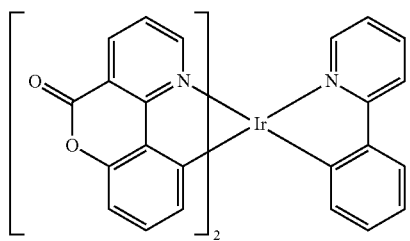

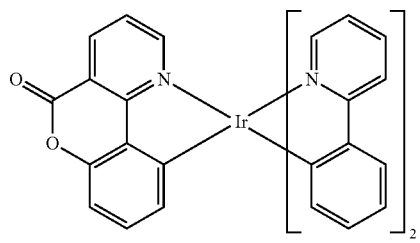
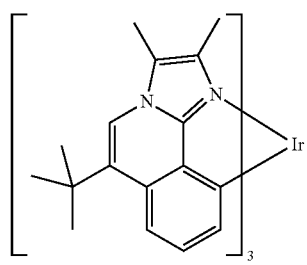
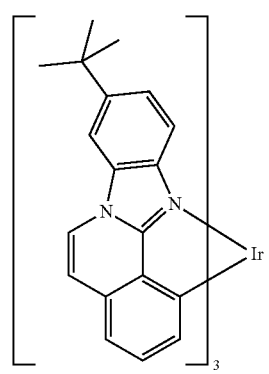
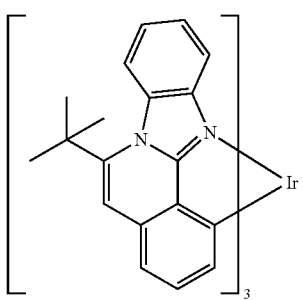
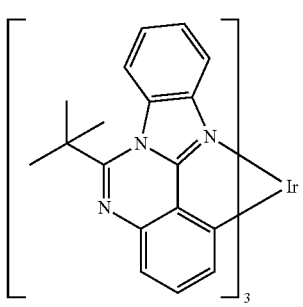
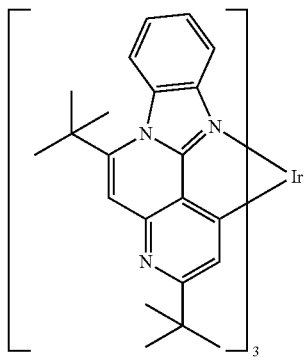
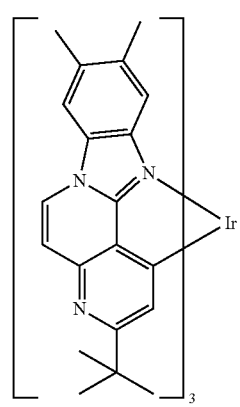
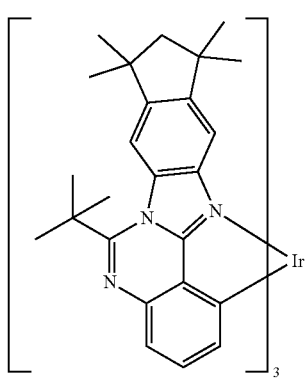
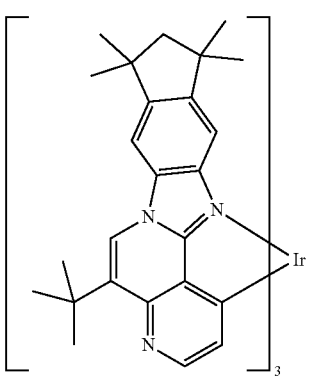

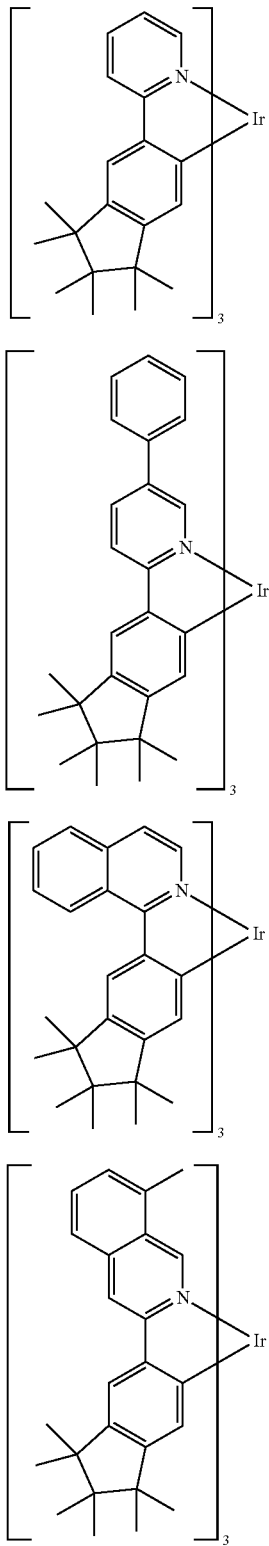

The above-described compound comprising structures of the formula (1) or the above-detailed preferred embodiments can preferably be used as active component in an electronic device. An electronic device is understood to mean any device comprising anode, cathode and at least one layer, said layer comprising at least one organic or organometallic compound. The electronic device of the invention thus comprises anode, cathode and at least one layer containing at least one compound comprising structures of the formula (1). Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), organic electrical sensors, light-emitting electrochemical cells (LECs) and organic laser diodes (O-lasers), containing at least one compound comprising structures of the formula (1) in at least one layer. Particular preference is given to organic electroluminescent devices. Active components are generally the organic or inorganic materials introduced between the anode and cathode, for example charge injection, charge transport or charge blocker materials, but especially emission materials and matrix materials.

A preferred embodiment of the invention is organic electroluminescent devices. The organic electroluminescent device comprises cathode, anode and at least one emitting layer. Apart from these layers, it may comprise further layers, for example in each case one or more hole injection layers, hole transport layers, hole blocker layers, electron transport layers, electron injection layers, exciton blocker layers, electron blocker layers, charge generation layers and/or organic or inorganic p/n junctions. At the same time, it is possible that one or more hole transport layers are p-doped, for example with metal oxides such as $MoO_3$ or $WO_3$ or with (per)fluorinated electron-deficient aromatic systems, and/or that one or more electron transport layers are n-doped. It is likewise possible for interlayers to be introduced between two emitting layers, these having, for example, an exciton-blocking function and/or controlling the charge balance in the electroluminescent device. However, it should be pointed out that not necessarily every one of these layers need be present.

In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are three-layer systems where the three layers exhibit blue, green and orange or red emission (for the basic construction see, for example, WO 2005/011013), or systems having more than three emitting layers. The system may also be a hybrid system wherein one or more layers fluoresce and one or more other layers phosphoresce.

In a preferred embodiment of the invention, the organic electroluminescent device contains the compound of the invention comprising structures of formula (1) or the above-detailed preferred embodiments as matrix material, preferably as electron-conducting matrix material, in one or more emitting layers, preferably in combination with a further matrix material, preferably a hole-conducting matrix material. An emitting layer comprises at least one emitting compound.

The matrix material used may generally be any materials which are known for the purpose according to the prior art. The triplet level of the matrix material is preferably higher than the triplet level of the emitter.

Suitable matrix materials for the compounds of the invention are ketones, phosphine oxides, sulfoxides and sulfones, for example according to WO 2004/013080, WO 2004/093207, WO 2006/005627 or WO 2010/006680, triarylamines, carbazole derivatives, e.g. CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example according to WO 2007/063754 or WO 2008/056746, indenocarbazole derivatives, for example according to WO 2010/136109 or WO 2011/000455, azacarbazoles, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, diazasilole derivatives, for example according to WO 2010/054729, diazaphosphole derivatives, for example according to WO 2010/054730, triazine derivatives, for example according to WO 2010/015306, WO 2007/063754 or WO 2008/056746, zinc complexes, for example according to EP 652273 or WO 2009/062578, dibenzofuran derivatives, for example according to WO 2009/148015, or bridged carbazole derivatives, for example according to US 2009/0136779, WO 2010/050778, WO 2011/042107 or WO 2011/088877.

It may also be preferable to use a plurality of different matrix materials as a mixture, especially at least one electron-conducting matrix material and at least one hole-conducting matrix material. Preference is likewise given to the use of a mixture of a charge-transporting matrix material and an electrically inert matrix material having no significant involvement, if any, in the charge transport, as described, for example, in WO 2010/108579.

It is further preferable to use a mixture of two or more triplet emitters together with a matrix. In this case, the triplet emitter having the shorter-wave emission spectrum serves as co-matrix for the triplet emitter having the longer-wave emission spectrum.

More preferably, it is possible to use a compound of the invention comprising structures of formula (1), in a preferred embodiment, as matrix material in an emission layer of an organic electronic device, especially in an organic electroluminescent device, for example in an OLED or OLEC. In this case, the matrix material containing compound comprising structures of formula (1) is present in the electronic device in combination with one or more dopants, preferably phosphorescent dopants.

The proportion of the matrix material in the emitting layer in this case is between 50.0% and 99.9% by volume, preferably between 80.0% and 99.5% by volume, and more preferably between 92.0% and 99.5% by volume for fluorescent emitting layers and between 85.0% and 97.0% by volume for phosphorescent emitting layers.

Correspondingly, the proportion of the dopant is between 0.1% and 50.0% by volume, preferably between 0.5% and 20.0% by volume, and more preferably between 0.5% and 8.0% by volume for fluorescent emitting layers and between 3.0% and 15.0% by volume for phosphorescent emitting layers.

An emitting layer of an organic electroluminescent device may also comprise systems comprising a plurality of matrix materials (mixed matrix systems) and/or a plurality of dopants. In this case too, the dopants are generally those materials having the smaller proportion in the system and the matrix materials are those materials having the greater proportion in the system. In individual cases, however, the proportion of a single matrix material in the system may be less than the proportion of a single dopant.

In a further preferred embodiment of the invention, the compound comprising structures of formula (1) is used as a component of mixed matrix systems. The mixed matrix systems preferably comprise two or three different matrix materials, more preferably two different matrix materials. Preferably, in this case, one of the two materials is a material having hole-transporting properties and the other material is a material having electron-transporting properties. The desired electron-transporting and hole-transporting properties of the mixed matrix components may, however, also be combined mainly or entirely in a single mixed matrix component, in which case the further mixed matrix component(s) fulfill(s) other functions. The two different matrix materials may be present in a ratio of 1:50 to 1:1, preferably 1:20 to 1:1, more preferably 1:10 to 1:1 and most preferably 1:4 to 1:1. Preference is given to using mixed matrix systems in phosphorescent organic electroluminescent devices. One source of more detailed information about mixed matrix systems is the application WO 2010/108579.

The present invention further provides an electronic device, preferably an organic electroluminescent device, comprising one or more compounds of the invention and/or at least one oligomer, polymer or dendrimer of the invention in one or more electron-conducting layers, as electron-conducting compound.

Preferred cathodes are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag, in which case combinations of the metals such as Mg/Ag, Ca/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). Likewise useful for this purpose are organic alkali metal complexes, e.g. Liq (lithium quinolinate). The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/$NiO_x$, Al/$PtO_x$) may also be preferred. For some applications, at least one of the electrodes has to be transparent or partly transparent in order to enable either the irradiation of the organic material (O-SC) or the emission of light (OLED/PLED, O-laser). Preferred anode materials here are conductive mixed metal oxides. Particular preference is given to indium tin oxide (ITO) or indium zinc oxide (IZO). Preference is further given to conductive doped organic materials, especially conductive doped polymers, for example PEDOT, PANI or derivatives of these polymers. It is further preferable when a p-doped hole transport material is applied to the anode as hole injection layer, in which case suitable p-dopants are metal oxides, for example $MoO_3$ or $WO_3$, or (per)fluorinated electron-deficient aromatic systems. Further suitable p-dopants are HAT-CN (hexacyanohexaazatriphenylene) or the compound NPD9 from Novaled. Such a layer simplifies hole injection into materials having a low HOMO, i.e. a large HOMO in terms of magnitude.

In the further layers, it is generally possible to use any materials as used according to the prior art for the layers, and the person skilled in the art is able, without exercising inventive skill, to combine any of these materials with the materials of the invention in an electronic device.

The device is correspondingly (according to the application) structured, contact-connected and finally hermetically sealed, since the lifetime of such devices is severely shortened in the presence of water and/or air.

Additionally preferred is an electronic device, especially an organic electroluminescent device, which is characterized in that one or more layers are coated by a sublimation process. In this case, the materials are applied by vapor deposition in vacuum sublimation systems at an initial pressure of typically less than $10^{-5}$ mbar, preferably less than $10^{-6}$ mbar. It is also possible that the initial pressure is even lower or even higher, for example less than $10^{-7}$ mbar.

Preference is likewise given to an electronic device, especially an organic electroluminescent device, which is characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example, M. S. Arnold et al., *Appl. Phys. Lett.* 2008, 92, 053301).

Preference is additionally given to an electronic device, especially an organic electroluminescent device, which is characterized in that one or more layers are produced from solution, for example by spin-coating, or by any printing method, for example screen printing, flexographic printing, offset printing or nozzle printing, but more preferably LITI (light-induced thermal imaging, thermal transfer printing) or inkjet printing. For this purpose, soluble compounds are needed, which are obtained, for example, through suitable substitution.

The electronic device, especially the organic electroluminescent device can also be produced as a hybrid system by applying one or more layers from solution and applying one or more other layers by vapor deposition. For example, it is possible to apply an emitting layer comprising a compound of the invention comprising structures of formula (1) and a matrix material from solution, and to apply a hole blocker layer and/or an electron transport layer thereto by vapor deposition under reduced pressure.

These methods are known in general terms to those skilled in the art and can be applied without difficulty to electronic devices, especially organic electroluminescent devices comprising compounds of the invention comprising structures of formula (1) or the above-detailed preferred embodiments.

The electronic devices of the invention, especially organic electroluminescent devices, are notable for one or more of the following surprising advantages over the prior art:

1. Electronic devices, especially organic electroluminescent devices, comprising compounds, oligomers, polymers or dendrimers having structures of formula (1), especially as electron-conducting materials, have a very good lifetime.
2. Electronic devices, especially organic electroluminescent devices, comprising compounds, oligomers, polymers or dendrimers having structures of formula (1) as electron-conducting materials have excellent efficiency. More particularly, efficiency is much higher compared to analogous compounds containing no structural unit of formula (1).
3. The compounds, oligomers, polymers and dendrimers of the invention having structures of the formula (1) exhibit very high stability and lead to compounds having a very long lifetime.
4. With compounds, oligomers, polymers or dendrimers having structures of formula (1), it is possible to avoid the formation of optical loss channels in electronic devices, especially organic electroluminescent devices. As a result, these devices feature a high PL efficiency and hence high EL efficiency of emitters, and excellent energy transmission of the matrices to dopants.
5. The use of compounds, oligomers, polymers or dendrimers having structures of formula (1) in layers of electronic devices, especially organic electroluminescent devices, leads to a high mobility of the electron conductor structures.
6. Compounds, oligomers, polymers and dendrimers having structures of formula (1) feature excellent thermal stability, and compounds having a molar mass of less than about 1200 g/mol have good sublimability.
7. Compounds, oligomers, polymers and dendrimers having structures of formula (1) have excellent glass film formation.
8. Compounds, oligomers, polymers and dendrimers having structures of formula (1) form very good films from solutions.
9. Some of the compounds, oligomers, polymers or dendrimers comprising structures of formula (1) have a surprisingly high triplet level $T_1$.

These abovementioned advantages are not accompanied by a deterioration in the further electronic properties.

The present invention further provides for the use of a compound of the invention and/or an oligomer, polymer or dendrimer of the invention in an electronic device as hole blocker material, electron injection material and/or electron transport material.

It should be pointed out that variations of the embodiments described in the present invention are covered by the scope of this invention. Any feature disclosed in the present invention may, unless this is explicitly ruled out, be exchanged for alternative features which serve the same purpose or an equivalent or similar purpose. Thus, any feature disclosed in the present invention, unless stated otherwise, should be considered as an example of a generic series or as an equivalent or similar feature.

All features of the present invention may be combined with one another in any manner, unless particular features and/or steps are mutually exclusive. This is especially true of preferred features of the present invention. Equally, features of non-essential combinations may be used separately (and not in combination).

It should also be pointed out that many of the features, and especially those of the preferred embodiments of the present invention, are themselves inventive and should not be regarded merely as some of the embodiments of the present invention. For these features, independent protection may be sought in addition to or as an alternative to any currently claimed invention.

The technical teaching disclosed with the present invention may be abstracted and combined with other examples.

The invention is illustrated in detail by the examples which follow, without any intention of restricting it thereby.

The person skilled in the art will be able to use the details given, without exercising inventive skill, to produce further electronic devices of the invention and hence to execute the invention over the entire scope claimed.

EXAMPLES

The syntheses which follow, unless stated otherwise, are conducted under a protective gas atmosphere in dried solvents. The metal complexes are additionally handled with exclusion of light or under yellow light. The solvents and reagents can be purchased, for example, from Sigma-ALDRICH or ABCR. The respective figures in square brackets or the numbers quoted for individual compounds relate to the CAS numbers of the compounds known from the literature.

A: Synthesis of the Synthons

Example S1

5-[1-Hydroxymeth-(E)-ylidene]-2,2-4,4-tetramethyl-cyclopentanone [81887-98-1]

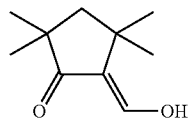

To a well-stirred suspension of 9.6 g (100 mmol) of sodium tert-butoxide in 300 mL of methyl tert-butyl ether is added dropwise a mixture of 14.0 g (100 mmol) of 2,2,4,4-tetramethylcyclopentanone [4694-11-5], 9.6 g (130 mmol) of ethyl formate [109-94-4] and 250 mL of methyl tert-butyl ether (caution: exothermic). After the addition has ended, the mixture is heated to 60° C. for 16 h. After cooling, the precipitated beige-red solid is filtered off with suction, washed once with a little methyl tert-butyl ether, resuspended in 300 mL of methyl tert-butyl ether and hydrolyzed by addition of 200 mL of saturated ammonium chloride solution. The clear organic phase is removed, washed three times with 100 mL each time of water and once with 100 mL of saturated sodium chloride solution and dried over magnesium sulfate, and then the solvent is removed under reduced pressure, leaving a yellow oil which crystallizes over time and which can be used in the next step without further purification. Yield: 14.5 g (86 mmol), 86%; purity: about 95% by $^1$H NMR.

In an analogous manner, it is possible to prepare the following compounds:

| Ex. | Ketone | Product | Yield |
|---|---|---|---|
| S2 | 5455-94-7 | 7441-66-9 | 78% |
| S3 | 497/-38 | 122901-79-5 | 82% |
| S4 | 464-49-3 | 14681-31-3 | 77% |
| S5 | 2716-23-6 | 935-82-0 | 80% |
| S6 | 24669-56-5 | | 81% |

It is well-known to those skilled in the art that the products S1 to S6 may be present not just in the Z form but also in the E form. In addition, it is well-known to those skilled in the art that the enol form of the products S1 to S6 shown is not the only form in which the products may be present. In fact, keto-enol tautomerism is present, and so the products S1 to S6 may also be present in the keto form.

B: Synthesis of the Inventive Heterocycles H

Example H1

7,7,9,9-Tetramethyl-8,9-dihydro-7H-benzo[h]cyclopenta[c]quinoline

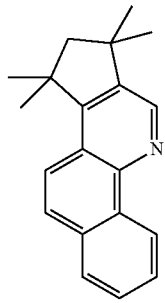

A mixture of 16.8 g (100 mmol) of 5-[1-hydroxymeth-(E)-ylidene]-2,2-4,4-tetramethylcyclopentanone, S1, and 14.3 g (100 mmol) of 1-amino-naphthalene, [134-32-7], is heated gradually to 160° C. on a water separator, in the course of which the water formed in the reaction is distilled gradually out of the melt. After 10 h at 160° C., 100 mL of toluene are slowly added dropwise and the latter is distilled off by means of the water separator, in order to remove the rest of the water from the melt and the apparatus. To the deep brown melt thus obtained are added, in an argon countercurrent, about 300 g of polyphosphoric acid (Merck KGaA) and then the mixture is stirred at 160° C. for a further 16 h. After cooling to 120° C., 400 mL of water are added dropwise to the black viscous melt (caution: exothermic!) and the mixture is stirred further until the melt has fully homogenized, with precipitation of a brown solid. The suspension is transferred to a beaker containing 2 L of water and stirred for a further 1 h, and the solids are filtered off with suction and washed once with 300 mL of water. After sucking the solids dry, they are resuspended in 1 L of 15% by weight ammonia solution and the mixture is stirred for a further hour, and the solids are filtered off with suction again, washed to neutrality with water and then sucked dry. The solids are dissolved in 500 mL of dichloromethane, the solution is washed with saturated sodium chloride solution, and the organic phase is dried over magnesium sulfate. After the desiccant has been removed, the solution is concentrated and the glassy residue is columned once on Alox, basic, activity level 1, and once on silica gel with dichloromethane. The viscous oil thus obtained is freed of low boilers and nonvolatile secondary components by fractional Kugelrohr distillation twice. Yield: 15.2 g (55 mmol), 55%; purity: about 99.5% by $^1$H NMR.

Example H2

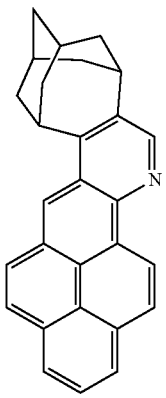

A mixture of 19.2 g (100 mmol) of 5-[1-hydroxymeth-[E]-ylidene-9-tricyclo[4.3.1.1*3,8*]undecan-4-one, S6, and 21.7 g (100 mmol) of 1-amino-pyrene, [1606-67-3], is heated gradually to 160° C. on a water separator, in the course of which the water formed in the reaction is distilled gradually out of the melt. After 10 h at 160° C., 100 mL of toluene are slowly added dropwise and the latter is distilled off by means of the water separator, in order to remove the rest of the water from the melt and the apparatus. To the deep brown melt thus obtained are added, in an argon countercurrent, about 300 g of polyphosphoric acid (Merck KGaA) and then the mixture is stirred at 160° C. for a further 16 h. After cooling to 120° C., 400 mL of water are added dropwise to the black viscous melt (caution: exothermic!) and the mixture is stirred further until the melt has fully homogenized, with precipitation of a brown solid. The suspension is transferred to a beaker containing 2 L of water and stirred for a further 1 h, and the solids are filtered off with suction and washed once with 300 mL of water. After sucking the solids dry, they are resuspended in 1 L of 15% by weight ammonia solution and the mixture is stirred for a further hour, and the solids are filtered off with suction again, washed to neutrality with water and then sucked dry. The solids are dissolved in 500 mL of dichloromethane, the solution is washed with saturated sodium chloride solution, and the organic phase is dried over magnesium sulfate. After the desiccant has been removed, the solution is concentrated and the glassy residue is columned once on Alox, basic, activity level 1, and twice on silica gel with dichloromethane. The solids thus obtained are recrystallized three times from DMF/EtOH and then fractionally sublimed twice (p about $10^{-5}$ mbar, T 290° C.). Yield: 13.5 g (36 mmol), 36%; purity: about 99.9% by $^1$H NMR.

In an analogous manner, it is possible to prepare the following compounds, where the ratio of amine to β-hydroxymethylene ketone in the case of the di-, tri- and tetraamines is correspondingly adjusted stoichiometrically:

| Ex. | β-Hydroxymethylene ketone | Product | Yield |
|---|---|---|---|
| | | Monoamine | |
| H3 | S1 78832-53-8 | | 46% |

-continued
| Ex. | β-Hydroxymethylene ketone | Product | Yield |
|---|---|---|---|
| H4 | 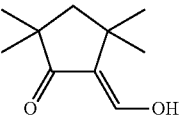 S1 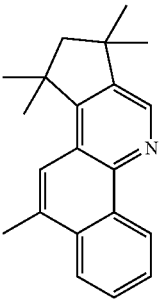 4523-45-9 | 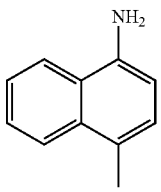 | 51% |
| H5 | 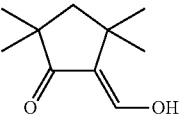 S1 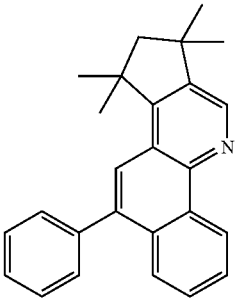 87833-80-5 | 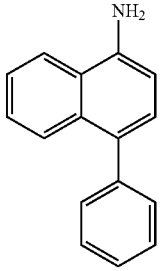 [SMILES: Nc1ccc(-c2ccccc2)c2ccccc12] | 53% |
| H6 | 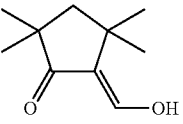 S1 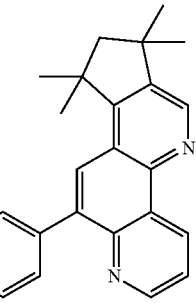 216059-99-3 | 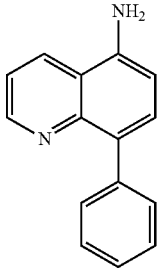 [SMILES: Nc1ccc(-c2ccccc2)c2ncccc12] | 46% |

| Ex. | β-Hydroxymethylene ketone | Product | Yield |
|---|---|---|---|
| H7 | 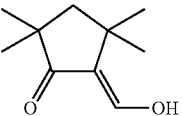<br>S1<br>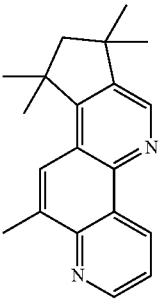<br>50358-40-2 | 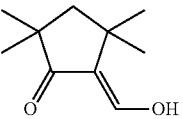 | 42% |
| H8 | 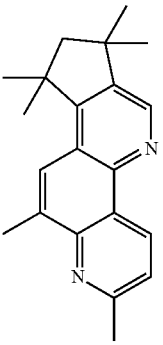 [SMILES: Cc1ccc2c(n1)c(C)cc1c3c(cnc12)C(C)(C)CC3(C)C]<br>S1<br>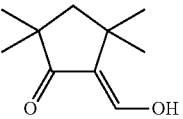<br>64485-52-5 | 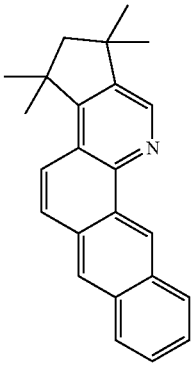 [SMILES: CC1(C)CC(C)(C)c2c1cnc1c2ccc2cc3ccccc3cc21] | 44% |
| H9 | <br>S1<br>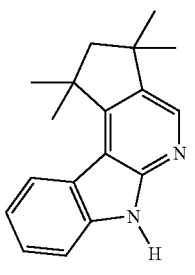 [SMILES: CC1(C)CC(C)(C)c2c1cnc1[nH]c3ccccc3c21]<br>610-49-1 |  | 36% |
| H10 | <br>S1<br><br>36946-70-0 |  | 32% |

-continued
| Ex. | β-Hydroxymethylene ketone | Product | Yield |
|---|---|---|---|
| H11 | 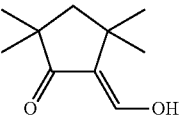 S2<br>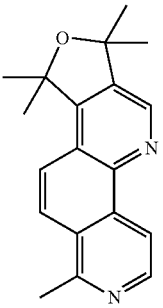 [SMILES: Cc1nccc2c1ccc1c3c(cnc12)C(C)(C)OC3(C)C] 20335-61-9 | 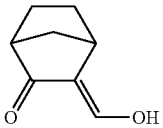 | 24% |
| H12 | 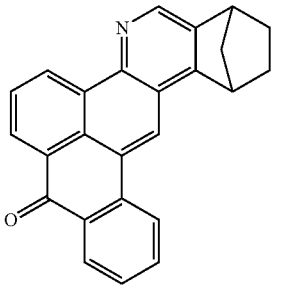 [SMILES: O=C1c2ccccc2-c2cc3c4c(cnc3c3cccc1c23)C1CCC4C1] S3<br>13456-80-9 |  | 38% |
| H13 | S4<br>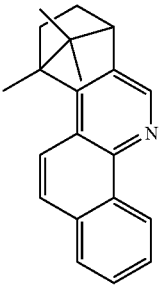 [SMILES: CC12CCC(c3cnc4c(ccc5ccccc54)c31)C2(C)C] 4176-50-5 | | 49% |

-continued
| Ex. | β-Hydroxymethylene ketone | Product | Yield |
|---|---|---|---|
| H14 | 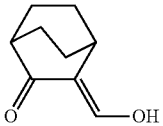<br>S5<br>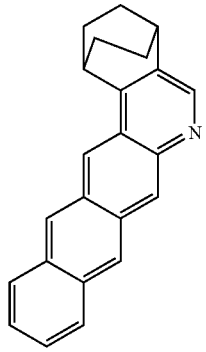 [SMILES: c1ccc2cc3cc4c5c(cnc4cc3cc2c1)C1CCC5CC1]<br>613-13-8 | 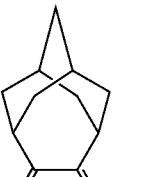 | 44% |
| H15 | 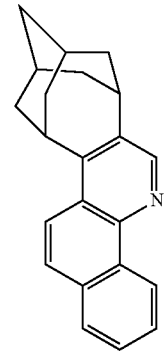 [SMILES: c1ccc2c(c1)ccc1c3c(cnc12)C1CC2CC(C1)CC3C2]<br>S6<br>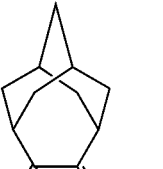<br>4176-50-5 | 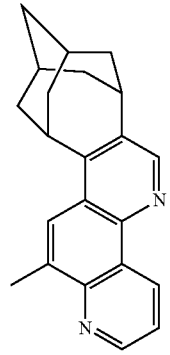 [SMILES: Cc1cc2c3c(cnc2c2cccnc12)C1CC2CC(C1)CC3C2] | 50% |
| H16 | S6<br>50358-40-2 | | 43% |

-continued
| Ex. | β-Hydroxymethylene ketone | Product | Yield |
|---|---|---|---|
| H17 | 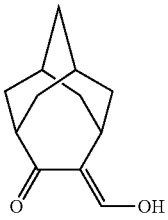<br>S6<br>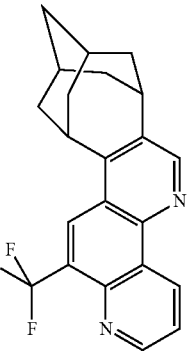<br>161431-57-8 | 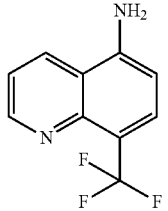 [SMILES: Nc1ccc(C(F)(F)F)c2ncccc12] | 28% |
| H18 | 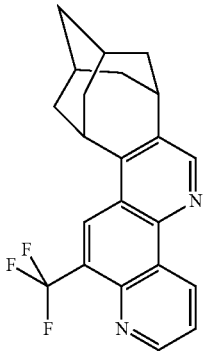 [SMILES: FC(F)(F)c1cc2c3c(cnc2c2cccnc12)C1CC2CC(C1)CC3C2]<br>S6<br>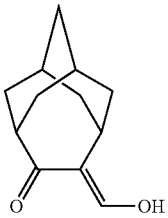 [SMILES: O=C1/C(=C/O)C2CC3CC(CC1C3)C2]<br>175229-87-5 | 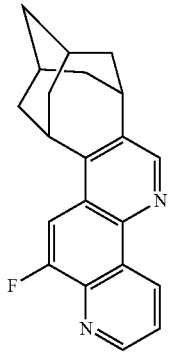 | 29% |
| H19 | 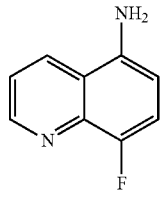 [SMILES: Nc1ccc(F)c2ncccc12]<br>S6<br>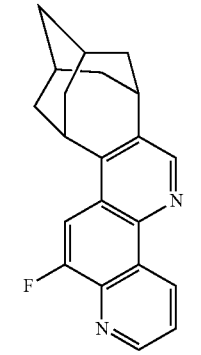 [SMILES: Fc1cc2c3c(cnc2c2cccnc12)C1CC2CC(C1)CC3C2]<br>175229-87-5 | 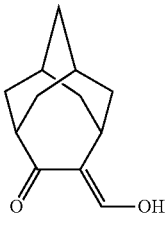 | 44% |

-continued

| Ex. | β-Hydroxymethylene ketone | Product | Yield |
|---|---|---|---|
| H20 | S6; 139266-08-3 | | 30% |
| H21 | S6; 36946-70-0 | | 26% |
| H22 | S6; 1318253-36-9 | | 27% |

-continued
| Ex. | β-Hydroxymethylene ketone | Product | Yield |
|---|---|---|---|
| H23 | 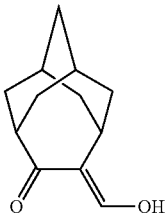<br>S6<br>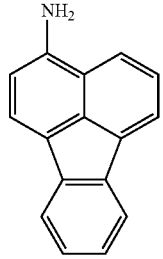 [SMILES: Nc1ccc2c3c(cccc13)-c1ccccc1-2]<br>2693-46-1 | 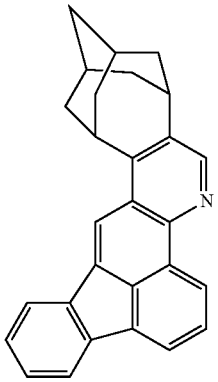 [SMILES: c1ccc2c(c1)-c1cccc3c1c-2cc1c2c(cnc13)C1CC3CC(C1)CC2C3] | 46% |
| H24 | 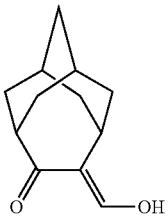 [SMILES: O=C1/C(=C/O)C2CC3CC(CC1C3)C2]<br>S6<br>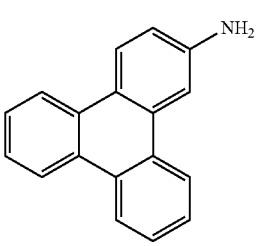 [SMILES: Nc1ccc2c3ccccc3c3ccccc3c2c1]<br>17169-81-2 | 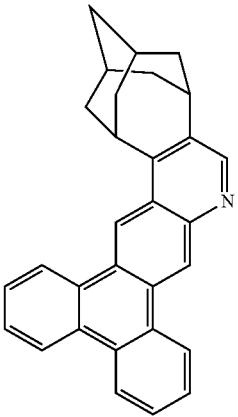 [SMILES: c1ccc2c(c1)c1ccccc1c1cc3c4c(cnc3cc21)C1CC2CC(C1)CC4C2] | 42% |

-continued
| Ex. | β-Hydroxymethylene ketone | Product | Yield |
|---|---|---|---|
| H25 | 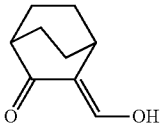-continued<br>S5<br>1606-67-3 | 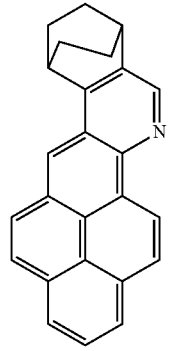 [SMILES: c1cc2ccc3cc4c5c(cnc4c4ccc(c1)c2c34)C1CCC5CC1] | 31% |
| | Diamine | | |
| H26 | 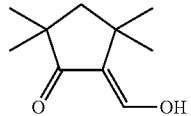<br>S1<br>95-94-5 | 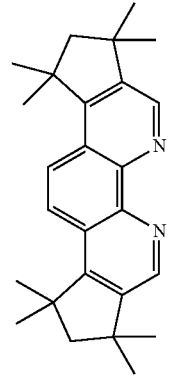 [SMILES: CC1(C)CC(C)(C)c2c1cnc1c2ccc2c3c(cnc21)C(C)(C)CC3(C)C] | 28% |
| H27 | 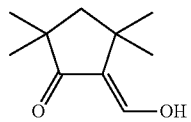<br>S1<br>481-91-4 | 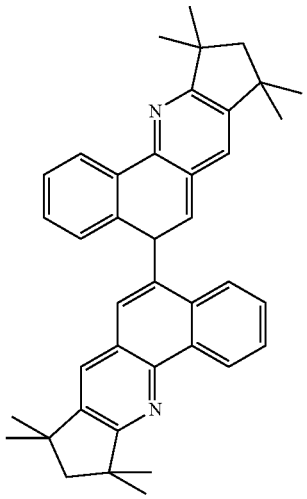 | 26% |

-continued
| Ex. | β-Hydroxymethylene ketone | Product | Yield |
|---|---|---|---|
| H28 | 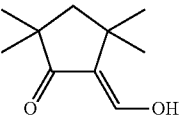<br>S1<br>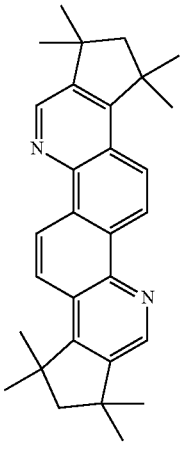<br>2243-62-1 | 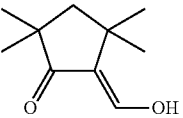 | 30% |
| H29 | 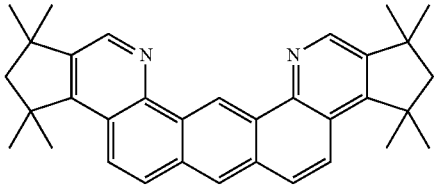 [SMILES: CC1(C)CC(C)(C)c2c1cnc1c2ccc2cc3ccc4c5c(cnc4c3cc21)C(C)(C)CC5(C)C]<br>S1<br><br>79014-49-9 | 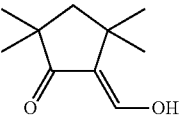 | 23% |
| H30 | 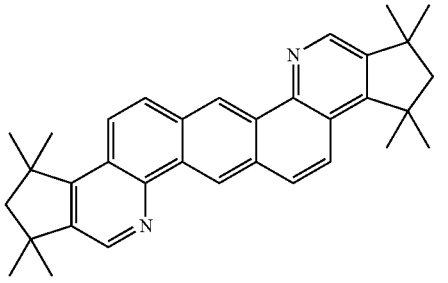 [SMILES: CC1(C)CC(C)(C)c2c1cnc1c2ccc2cc3c(ccc4c5c(cnc43)C(C)(C)CC5(C)C)cc21]<br>S1<br><br>139312-39-3 | | 28% |

-continued
| Ex. | β-Hydroxymethylene ketone | Product | Yield |
|---|---|---|---|
| H31 | 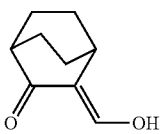<br>S5<br>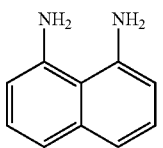<br>2243-62-1 | 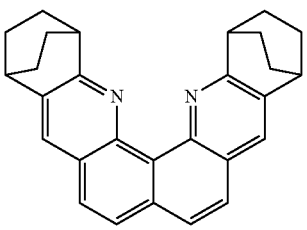 [SMILES: c1cc2ccc3cc4c(nc3c2c2nc3c(cc12)C1CCC3CC1)C1CCC4CC1] | 18% |
| H32 | 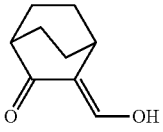 [SMILES: O=C1/C(=C/O)C2CCC1CC2]<br>S5<br>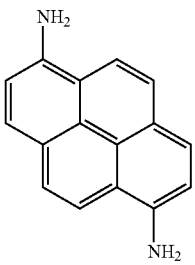 [SMILES: Nc1ccc2ccc3c(N)ccc4ccc1c2c43]<br>14923-84-3 | 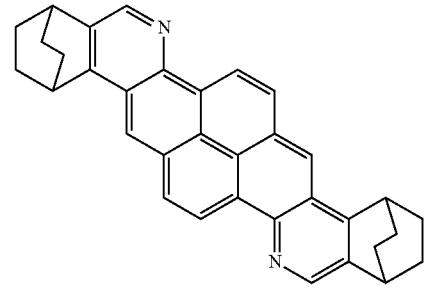 [SMILES: c1nc2c(cc3ccc4c5ncc6c(c5cc5ccc2c3c54)C2CCC6CC2)c2c1C1CCC2CC1] | 34% |
| H33 | 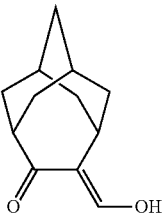<br>S6<br>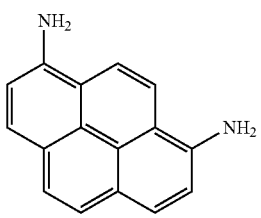 [SMILES: Nc1ccc2ccc3ccc(N)c4ccc1c2c34]<br>30269-04-6 | 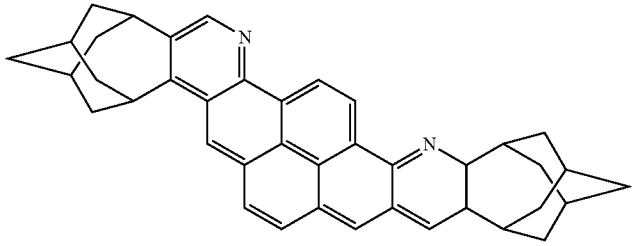 [SMILES: C1=c2cc3ccc4cc5c6c(cnc5c5ccc(c2=NC2C7CC8CC(CC(C8)C12)C7)c3c45)C1CC2CC(C1)CC6C2] | 30% |

-continued

| Ex. | β-Hydroxymethylene ketone | Product | Yield |
|---|---|---|---|
| H34 | S1<br>67665-45-6 | | 29% |
| H35 | S6<br>117110-85-7 | | 27% |

Triamines

| H36 | S6<br>108-72-5 | | 11% |

-continued

| Ex. | β-Hydroxymethylene ketone | Product | Yield |
|---|---|---|---|
| | | Tetraamines | |
| H37 | 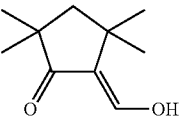 S1 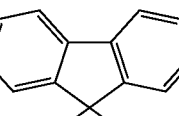 376356-61-5 | 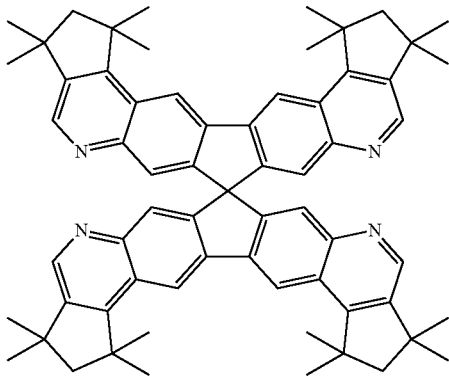 | 17% |

Example H38

6-Phenyl-1,1,3,3-tetramethyl-2,3-dihydro-1H-12-azaindeno[5,4-a]anthracene, H37

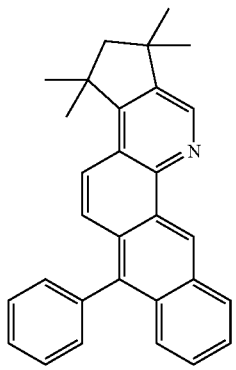 [SMILES: CC1(C)CC(C)(C)c2c1cnc1c2ccc2c(-c3ccccc3)c3ccccc3cc21]

a) 6-Bromo-1,1,3,3-tetramethyl-2,3-dihydro-1H-12-azaindeno[5,4-a]anthracene, H38a

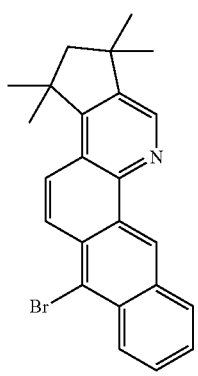 [SMILES: CC1(C)CC(C)(C)c2c1cnc1c2ccc2c(Br)c3ccccc3cc21]

A mixture of 3.3 g (10 mmol) of 1,1,3,3-tetramethyl-2,3-dihydro-1H-12-azaindeno[5,4-a]anthracene, H9, 2.0 g (11 mmol) of N-bromosuccinimide and 50 mL of DMF is stirred at 90° C. for 12 h. After cooling, the DMF is removed under reduced pressure, and the residue is subjected to hot extraction from 50 mL of ethanol and then recrystallized from dioxane/EtOH. Yield: 2.8 g (7 mmol) 70%. Purity: about 98% by $^1$H NMR.

b) 6-Phenyl-1,1,3,3-tetramethyl-2,3-dihydro-1H-12-azaindeno[5,4-a]anthracene, H38

A mixture of 2.8 g (7 mmol) of 6-bromo-1,1,3,3-tetramethyl-2,3-dihydro-1H-12-azaindeno[5,4-a]anthracene, H38a, 1.2 g (10 mmol) of phenylboronic acid [98-80-6], 5.8 g (30 mmol) of tripotassium phosphate, 123 mg (0.5 mmol) of palladium(II)acetate, 913 mg (3 mmol) of tri-o-tolylphosphine, 20 mL of toluene, 10 mL of dioxane and 30 mL of water is heated under reflux for 16 h. After cooling, the precipitated solids are filtered off with suction and dissolved in 200 mL of dichloromethane, the solution is filtered through a Celite bed, the filtrate is concentrated, and the solids thus obtained are crystallized three times from DMF/EtOH and fractionally sublimed (p about $10^{-5}$ mbar, T 310° C.). Yield: 1.4 g (3.5 mmol), 50%; purity: about 99.9% by $^1$H NMR.

Example H39

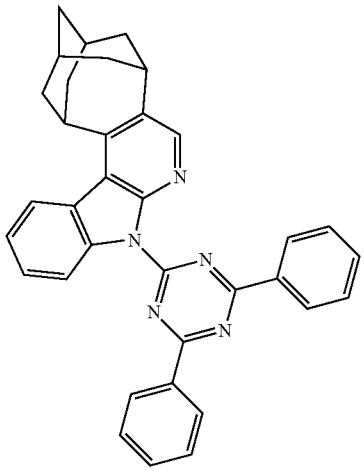 [SMILES: c1ccc(-c2nc(-c3ccccc3)nc(-n3c4ccccc4c4c5c(cnc43)C3CC4CC(C3)CC5C4)n2)cc1]

To a suspension of 264 mg (11 mmol) of sodium hydride in 50 mL of DMF are added 2.9 g (10 mmol) of H21 in portions, and the mixture is stirred at 50° C. for 30 min. Then 3.2 g (12 mmol) of 1-chloro-3,5-diphenyltriazine are added in portions and the mixture is stirred at 50° C. for a further 16 h. After adding 5 mL of methanol, the solvent is removed under reduced pressure, and the residue is taken up in 100 mL of dichloromethane, washed twice with 50 mL of water and dried over magnesium sulfate. After the solvent has been removed, the residue is recrystallized five times from DMF/EtOH and fractionally sublimed twice (p ca. $10^{-5}$ mbar, T 320° C.). Yield: 3.4 g (6.6 mmol), 66%; purity: about 99.9% by $^1$H NMR.

Example H40

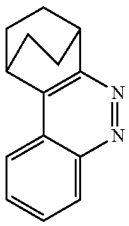 [SMILES: c1ccc2c3c(nnc2c1)C1CCC3CC1]

A mixture of 21.6 g (100 mmol) of 3-hydroxy-3-phenyl-bicyclo[2.2.2]octan-2-one [95800-12-7], 5.1 mL (100 mmol) of hydrazine hydrate and 200 mL of o-dichlorobenzene is heated stepwise on a water separator until the separation of water has ended. Then 1.0 g (5 mmol) of p-toluenesulfonic acid monohydrate [6192-52-4] is added and the mixture is heated again on the water separator until the separation of water has ended. Subsequently, 21.7 g (250 mmol) of activated manganese dioxide are added and the mixture is heated again until the separation of water has ended. After cooling to 70° C., the manganese salts are filtered off using a Celite bed (3 cm) and washed with a little o-dichlorobenzene, and then the o-dichlorobenzene is removed under reduced pressure. The residue is chromatographed on silica gel with n-heptane/ethyl acetate/methanol (5:1:0.1). Yield: 5.5 g (26 mmol), 26%; purity: about 99.8% by $^1$H NMR.

It is possible to prepare the following analogously:

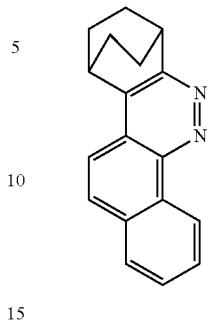

Production of the OLEDs

1) Vacuum-Processed Devices:

OLEDs of the invention and OLEDs according to the prior art are produced by a general method according to WO 2004/058911, which is adapted to the circumstances described here (variation in layer thickness, materials used).

In the examples which follow, the results for various OLEDs are presented. Glass plaques with structured ITO (indium tin oxide) form the substrates to which the OLEDs are applied. The OLEDs basically have the following layer structure: substrate/hole transport layer 1 (HTL1) consisting of HTM doped with 3% NDP-9 (commercially available from Novaled), 20 nm/hole transport layer 2 (HTL2)/optional hole transport layer 3 (HTL3)/emission layer (EML)/optional hole blocker layer (HBL)/electron transport layer (ETL)/optional electron injection layer (EIL) and finally a cathode. The cathode is formed by an aluminum layer of thickness 100 nm.

First of all, vacuum-processed OLEDs are described. For this purpose, all the materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as M3:M2:Ir dopant (55%:35%:10%) mean here that the material M3 is present in the layer in a proportion by volume of 55%, M2 in a proportion of 35% and Ir dopant in a proportion of 10%. Analogously, the electron transport layer may also consist of a mixture of two materials. The exact structure of the OLEDs can be found in Table 1. The materials used for production of the OLEDs are shown in Table 4.

The OLEDs are characterized in a standard manner. For this purpose, the electroluminescence spectra, the power efficiency (measured in cd/A) and the voltage (measured at 1000 cd/m² in V) are determined from current-voltage-brightness characteristics (IUL characteristics). For selected experiments, the lifetime is determined. The lifetime is defined as the time after which the luminance has fallen from a particular starting luminance to a certain proportion. The figure LD50 means that the lifetime specified is the time at which the luminance has dropped to 50% of the starting luminance, i.e. from, for example, 1000 cd/m² to 500 cd/m². According to the emission color, different starting brightnesses are selected. The values for the lifetime can be converted to a figure for other starting luminances with the aid of conversion formulae known to those skilled in the art. In this context, the lifetime for a starting luminance of 1000 cd/m² is a standard figure.

Use of Compounds of the Invention as Emitter Materials in Phosphorescent OLEDs

The uses of the compounds of the invention include uses as triplet matrix material (TMM), electron transport material (ETM), hole blocker material (HBM), blue singlet matrix material (SMB) and blue singlet emitter (SEB) in OLEDs.

TABLE 1

Structure of the OLED

| Ex. | HTL2 thickness | HTL-003 thickness | EML thickness | HBL thickness | ETL thickness |
|---|---|---|---|---|---|
| | | | Use as TMM green | | |
| D1 | HTM 220 nm | — | H6:M2:Ir-G (65%:30%:5%) 25 nm | M1 10 nm | ETM1:ETM2 (50%:50%) 20 nm |
| D2 | HTM 220 nm | — | H20:M2:Ir-G (45%:50%:5%) 25 nm | M1 10 nm | ETM1:ETM2 (50%:50%) 20 nm |
| D3 | HTM 220 nm | — | H39:M2:Ir-G (65%:30%:5%) 25 nm | M1 10 nm | ETM1:ETM2 (50%:50%) 20 nm |
| | | | red | | |
| D4 | HTM 220 nm | — | H12:M2:Ir-R (65%:30%:5%) 30 nm | M1 10 nm | ETM1:ETM2 (50%:50%) 20 nm |
| D5 | HTM 220 nm | — | H19:M2:Ir-R (70%:20%:10%) 30 nm | M1 10 nm | ETM1:ETM2 (50%:50%) 20 nm |
| D6 | HTM 220 nm | — | H22:M2:Ir-R (60%:35%:5%) 30 nm | M1 10 nm | ETM1:ETM2 (50%:50%) 20 nm |
| D7 | HTM 220 nm | — | H23:M2:Ir-R (60%:35%:5%) 30 nm | M1 10 nm | ETM1:ETM2 (50%:50%) 20 nm |
| D8 | HTM 220 nm | — | H27:M2:Ir-R (50%:45%:5%) 30 nm | M1 10 nm | ETM1:ETM2 (50%:50%) 20 nm |
| D9 | HTM 220 nm | — | H28:M2:Ir-R (50%:45%:5%) 30 nm | M1 10 nm | H32:ETM2 (50%:50%) 20 nm |
| D10 | HTM 220 nm | — | H37:M2:Ir-R (45%:50%:5%) 30 nm | M1 10 nm | H37:ETM2 (50%:50%) 20 nm |
| | | | Use as ETM | | |
| D11 | HTM 220 nm | — | M1:M2:Ir-G (65%:30%:5%) 25 nm | M1 10 nm | H32:ETM2 (70%:30%) 30 nm |
| D12 | HTM 220 nm | — | M1:M2:Ir-G (65%:30%:5%) 25 nm | M1 10 nm | H34:ETM2 (50%:50%) 30 nm |
| | | | Use as SEB/SMB | | |
| D13 | HTM 190 nm | — | H25:SEB (95%:5%) 20 nm | — | ETM1:ETM2 (50%:50%) 30 nm |
| D14 | HTM 190 nm | — | H37:SEB (95%:5%) 20 nm | — | ETM1:ETM2 (50%:50%) 30 nm |

TABLE 2

Results for the vacuum-processed OLEDs

| Ex. | EQE (%) 1000 cd/m$^2$ | Voltage (V) 1000 cd/m$^2$ | CIE x/y 1000 cd/m$^2$ | LD50 (h) 1000 cd/m$^2$ |
|---|---|---|---|---|
| | | Use as TMM green | | |
| D1 | 18.8 | 4.2 | 0.35/0.64 | — |
| D2 | 17.5 | 4.0 | 0.35/0.64 | — |
| D3 | 19.1 | 4.1 | 0.35/0.64 | 80000 |
| | | red | | |
| D4 | 8.9 | 3.7 | 0.67/0.33 | 75000 |
| D5 | 15.0 | 3.6 | 0.67/0.33 | — |
| D6 | 16.6 | 3.6 | 0.66/0.34 | — |
| D7 | 10.0 | 3.8 | 0.66/0.34 | — |
| D8 | 15.8 | 3.6 | 0.67/0.33 | 90000 |
| D9 | 15.7 | 3.6 | 0.66/0.34 | 100000 |
| D10 | 10.1 | 3.5 | 0.68/0.31 | — |
| | | Use as ETM | | |
| D11 | 17.6 | 3.8 | 0.35/0.64 | 80000 |
| D12 | 18.4 | 4.0 | 0.34/0.63 | — |
| | | Use as SEB/SMB | | |
| D12 | 6.0 | 4.6 | 0.15/0.18 | 5000 |
| D13 | 6.3 | 4.5 | 0.15/0.17 | — |

2) Solution-Processed Devices:

A: From Soluble Functional Materials

The compounds of the invention may also be processed from solution and lead therein to OLEDs which are much simpler in terms of process technology compared to the vacuum-processed OLEDs, but nevertheless have good properties. The production of such components is based on the production of polymeric light-emitting diodes (PLEDs), which has already been described many times in the literature (for example in WO 2004/037887).

The structure is composed of substrate/ITO/PEDOT (80 nm)/interlayer (80 nm)/emission layer (80 nm)/cathode. For this purpose, substrates from Technoprint (soda-lime glass) are used, to which the ITO structure (indium tin oxide, a transparent conductive anode) is applied. The substrates are cleaned in a cleanroom with DI water and a detergent (Deconex 15 PF) and then activated by a UV/ozone plasma treatment. Thereafter, likewise in the cleanroom, as a buffer layer, an 80 nm layer of PEDOT (PEDOT is a polythiophene derivative (Baytron P VAI 4083sp.) from H. C. Starck, Goslar, which is supplied as an aqueous dispersion) is applied by spin-coating. The required spin rate depends on the degree of dilution and the specific spin-coater geometry (typical value for 80 nm: 4500 rpm). In order to remove residual water from the layer, the substrates are baked on a hotplate at 180° C. for 10 minutes. The interlayer used serves for hole injection; in this case, HIL-012 from Merck is used. The interlayer may alternatively also be replaced by one or more layers which merely have to fulfill the condition of not being leached off again by the subsequent processing step of EML deposition from solution. For production of the emission layer, the emitters of the invention are dissolved together with the matrix materials in toluene. The typical solids content of such solutions is between 16 and 25 g/l when, as here, the layer thickness of 80 nm which is typical of a device is to be achieved by means of spin-coating. The solution-processed devices contain an emission layer composed of (polystyrene):matrix1:matrix2:Ir-G-Sol (25%:

25%:30%:20%). The emission layer is spun on in an inert gas atmosphere, argon in the present case, and baked at 130° C. for 30 min. Lastly, a cathode composed of barium (5 nm) and then aluminum (100 nm) (high-purity metals from Aldrich, particularly barium 99.99% (cat. no. 474711); vapor deposition systems from Lesker or the like, typical vapor deposition pressure $5 \times 10^{-6}$ mbar) is applied by vapor deposition. It is optionally possible first to apply a hole blocker layer and then an electron transport layer and only then the cathode (e.g. Al or LiF/Al) by vapor deposition under reduced pressure. In order to protect the device from air and air humidity, the device is finally encapsulated and then characterized. The OLED examples cited are yet to be optimized; Table 3 summarizes the data obtained.

TABLE 3

Results with materials processed from solution

| Ex. | Matrix1 Matrix2 | EQE (%) 1000 cd/m² | Voltage (V) 1000 cd/m² | CIE x/y 1000 cd/m² |
|---|---|---|---|---|
| | | Green OLEDs | | |
| D-Sol1 | H27 M2 | 16.0 | 5.6 | 0.35/0.62 |
| D-Sol1 | H37 M3 | 15.9 | 5.8 | 0.34/0.63 |

TABLE 4

Structural formulae of the materials used

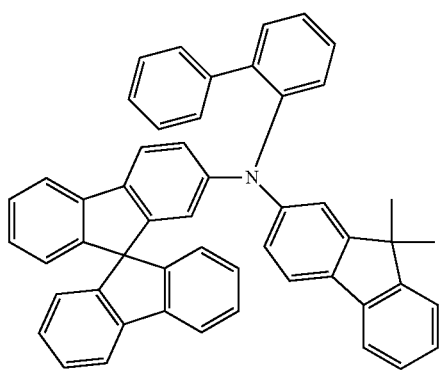 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

HTM

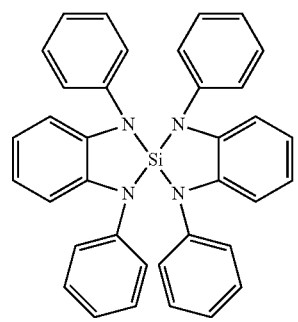 [SMILES: c1ccc(N2c3ccccc3N(c3ccccc3)[Si]23N(c2ccccc2)c2ccccc2N3c2ccccc2)cc1]

EBM

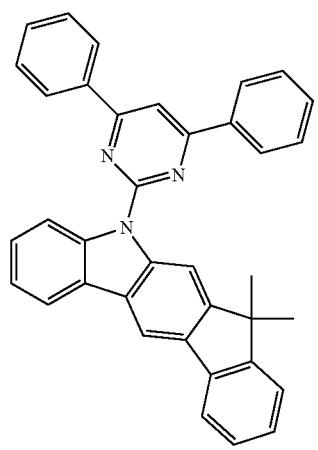 [SMILES: CC1(C)c2ccccc2-c2cc3c4ccccc4n(-c4nc(-c5ccccc5)cc(-c5ccccc5)n4)c3cc21]

M1 = HBM

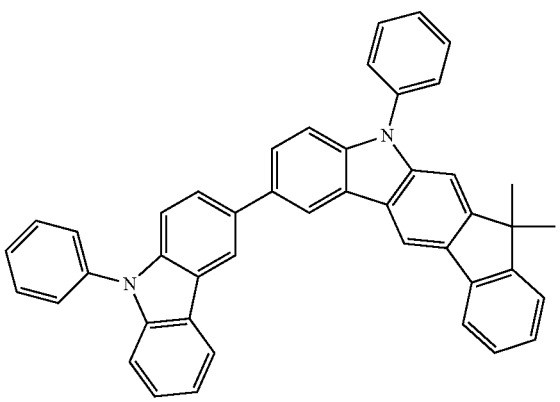 [SMILES: CC1(C)c2ccccc2-c2cc3c4cc(-c5ccc6c(c5)c5ccccc5n6-c5ccccc5)ccc4n(-c4ccccc4)c3cc21]

M2

TABLE 4-continued
Structural formulae of the materials used
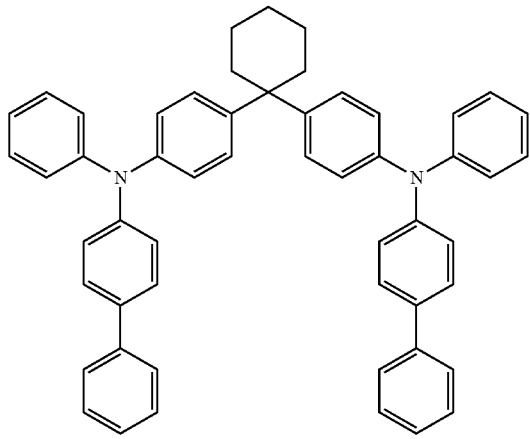 [SMILES: c1ccc(-c2ccc(N(c3ccccc3)c3ccc(C4(c5ccc(N(c6ccccc6)c6ccc(-c7ccccc7)cc6)cc5)CCCCC4)cc3)cc2)cc1]
M3
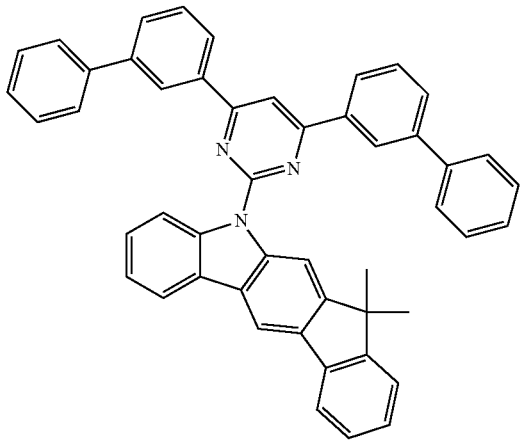 [SMILES: CC1(C)c2ccccc2-c2cc3c4ccccc4n(-c4nc(-c5cccc(-c6ccccc6)c5)cc(-c5cccc(-c6ccccc6)c5)n4)c3cc21]
M4
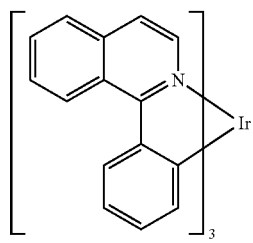
Ir-R
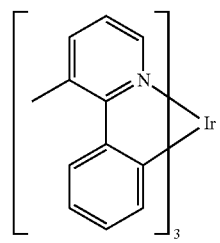
Ir-G
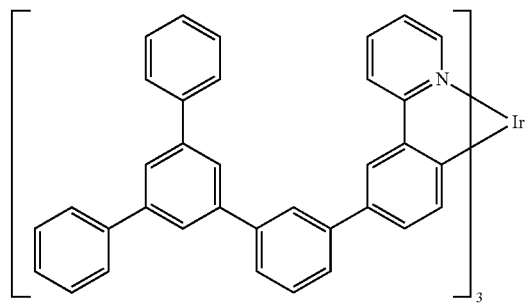
Ir-G-Sol
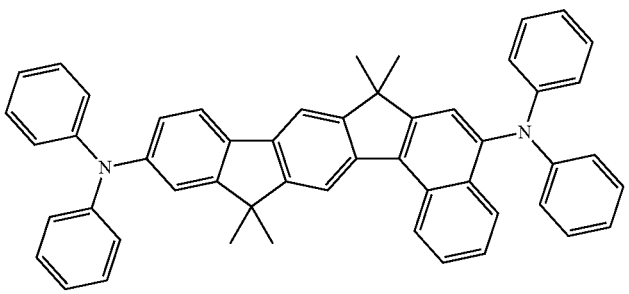 [SMILES: CC1(C)c2cc(N(c3ccccc3)c3ccccc3)ccc2-c2cc3c(cc21)-c1c(cc(N(c2ccccc2)c2ccccc2)c2ccccc12)C3(C)C]
SEB TABLE 4-continued Structural formulae of the materials used

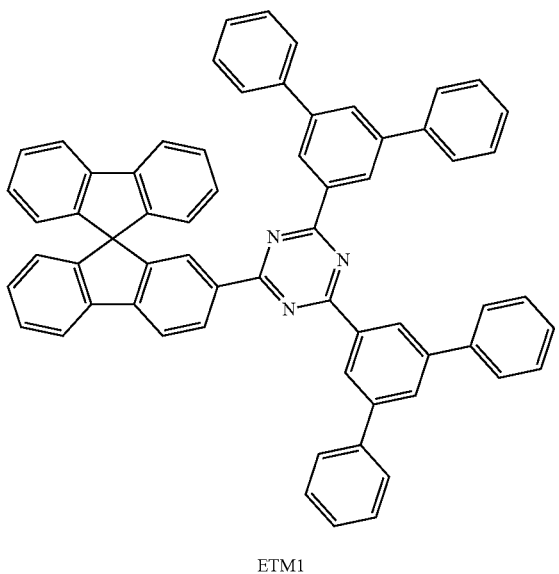

ETM1

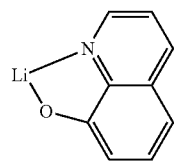

ETM2

The invention claimed is:

1. A compound of the general formula (1)

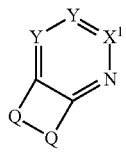

Formula (1)

where the symbols used are as follows:
Q is the same or different at each instance and is X═X, O, NR, S, SO, SO$_2$, PR, POR or BR, where at least one Q is X═X;
$X^1$ is CR or N;
X is the same or different at each instance and is N or CR;
Y is the same or different at each instance and is CR;
R is the same or different at each instance and is H, D, F, Cl, Br, I, N(R$^1$)$_2$, CN, NO$_2$, OH, COOH, C(═O)N(R$^1$)$_2$, Si(R$^1$)$_3$, B(OR$^1$)$_2$, C(═O)R$^1$, P(═O)(R$^1$)$_2$, S(═O)R$^1$, S(═O)$_2$R$^1$, OSO$_2$R$^1$, a straight-chain alkyl, alkoxy or thioalkoxy group having 1 to 20 carbon atoms or an alkenyl or alkynyl group having 2 to 20 carbon atoms or a branched or cyclic alkyl, alkoxy or thioalkoxy group having 3 to 20 carbon atoms, each of which may be substituted by one or more R$^1$ radicals, where one or more nonadjacent CH$_2$ groups may be replaced by R$^1$C═CR$^1$, C≡C, Si(R$^1$)$_2$, C═O, NR$^1$, O, S or CONR$^1$ and where one or more hydrogen atoms may be replaced by D, F, Cl, Br, I or CN, or an aromatic or heteroaromatic ring system which has 5 to 60 aromatic ring atoms and may be substituted in each case by one or more R$^1$ radicals, or an aryloxy or heteroaryloxy group which has 5 to 40 aromatic ring atoms and may be substituted by one or more R$^1$ radicals, or an aralkyl or heteroaralkyl group which has 5 to 40 aromatic ring atoms and may be substituted by one or more R$^1$ radicals, or a diarylamino group, diheteroarylamino group or arylheteroarylamino group which has 10 to 40 aromatic ring atoms and may be substituted by one or more R$^1$ radicals; at the same time, two adjacent R radicals together may also form a mono- or polycyclic, aliphatic, aromatic or heteroaromatic ring system;
R$^1$ is the same or different at each instance and is H, D, F, Cl, Br, I, N(R$^2$)$_2$, CN, NO$_2$, Si(R$^2$)$_3$, B(OR$^2$)$_2$, C(═O)R$^2$, P(═O)(R$^2$)$_2$, S(═O)R$^2$, S(═O)$_2$R$^2$, OSO$_2$R$^2$, a straight-chain alkyl, alkoxy or thioalkoxy group having 1 to 20 carbon atoms or an alkenyl or alkynyl group having 2 to 20 carbon atoms or a branched or cyclic alkyl, alkoxy or thioalkoxy group having 3 to 20 carbon atoms, each of which may be substituted by one or more R$^2$ radicals, where one or more nonadjacent CH$_2$ groups may be replaced by R$^2$C═CR$^2$, C≡C, Si(R$^2$)$_2$, C═O, NR$^2$, O, S or CONR$^2$ and where one or more hydrogen atoms may be replaced by D, F, Cl, Br, I, CN or NO$_2$, or an aromatic or heteroaromatic ring system which has 5 to 60 aromatic ring atoms and may be substituted in each case by one or more R$^2$ radicals, or an aryloxy or heteroaryloxy group which has 5 to 40 aromatic ring atoms and may be substituted by one or more R$^2$ radicals, or an aralkyl or heteroaralkyl group which has 5 to 40 aromatic ring atoms and may be substituted by one or more R$^2$ radicals, or a diarylamino group, diheteroarylamino group or arylheteroarylamino group which has 10 to 40 aromatic ring atoms and may be substituted by one or more R$^2$ radicals; at the same time, two or more adjacent R$^1$ radicals together, or R$^1$ together with R, may form a mono- or polycyclic, aliphatic, aromatic or heteroaromatic ring system;
R$^2$ is the same or different at each instance and is H, D, F or an aliphatic, aromatic and/or heteroaromatic hydrocarbyl radical having 1 to 20 carbon atoms, in which one or more hydrogen atoms may also be replaced by F; at the same time, two or more R² substituents together may also form a mono- or polycyclic aliphatic ring system;

which is characterized in that the respective R radicals of the two Y groups together with the carbon atoms of the heteroaromatic ring form a ring of the following formulae:

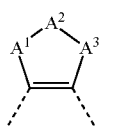

Formula (5)

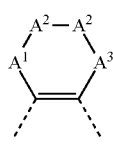

Formula (6)

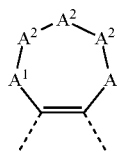

Formula (7)

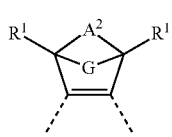

Formula (8)

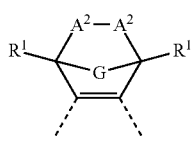

Formula (9)

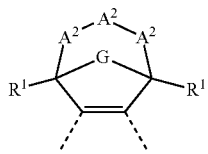

Formula (10)

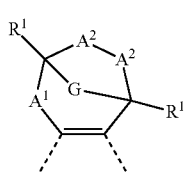

Formula (11)

where

A¹, A³ is the same or different at each instance and is C(R³)₂, O, S, NR³ or C(=O);

A² is C(R¹)₂, O, S, NR³ or C(=O);

G is a bivalent group selected from O, S, N(R²), B(R²), Si(R²)₂, C=O, C=NR², C=C(R²)₂, S=O, SO₂, P(R²) and P(=O)R², an alkylene group which has 1, 2 or 3 carbon atoms and may be substituted by one or more R² radicals, —CR²=CR²- or an ortho-bonded arylene or heteroarylene group which has 5 to 14 aromatic ring atoms and may be substituted by one or more R² radicals;

and where the carbon-carbon double bond shown in the formulae (5) to (11) corresponds to an aromatic double bond from the heteroaromatic ring to which the groups of the formulae (5) to (11) bind;

R³ is the same or different at each instance and is F, a straight-chain alkyl or alkoxy group having 1 to 10 carbon atoms, a branched or cyclic alkyl or alkoxy group having 3 to 10 carbon atoms, each of which may be substituted by one or more R² radicals, where one or more nonadjacent CH₂ groups may be replaced by R²C=CR², C≡C, Si(R²)₂, C=O, NR², O, S or CONR², and where one or more hydrogen atoms may be replaced by D or F, or an aromatic or heteroaromatic ring system which has 5 to 24 aromatic ring atoms and may be substituted in each case by one or more R² radicals, or an aryloxy or heteroaryloxy group which has 5 to 24 aromatic ring atoms and may be substituted by one or more R² radicals, or an aralkyl or heteroaralkyl group which has 5 to 24 aromatic ring atoms and may be substituted by one or more R² radicals; at the same time, two R³ radicals bonded to the same carbon atom together may form an aliphatic or aromatic ring system and thus form a Spiro system; in addition, R³ with an adjacent R or R¹ radical may form an aliphatic ring system;

with the proviso that no two identical heteroatoms in the aforementioned groups are bonded directly to one another and no two C=O groups are bonded directly to one another, and, in addition, if the two Y groups together are a ring structure of the formulae (12) or (13)

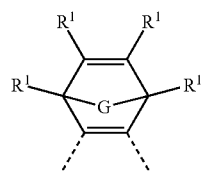

Formula (12)

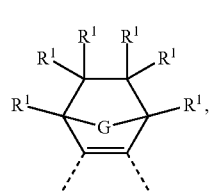

Formula (13)

the X¹ radical is not a group of the formula (14)

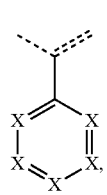

Formula (14)

in which X is as defined above and the dotted lines represent the bonds of the carbon atom of the X¹ radical to two further carbon atoms of the ring including the X¹ radical of formula (1);

wherein, in the ring structures of one of the formulae (5), (6), (7), (8), (9), (10), and/or (11), not more than one of the A¹, A², and A³ groups is O, S or NR³.

2. The compound of claim 1, wherein the heteroaromatic ring system having the $X^1$ radical is a system having 10 to 30 aromatic ring atoms.

3. The compound of claim 1, wherein the compound has a general structure having the formula (15):

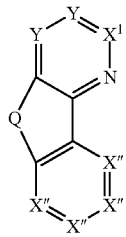

Formula (15)

where X" is the same or different at each instance and is $CR^1$ or N, where the symbols used are each as defined above.

4. The compound of claim 1, wherein Q is the same or different at each instance and is X=X.

5. The compound of claim 1, wherein, in the ring structures of one of the formulae (5), (6), (7), (8), (9), (10) and/or (11), the $A^1$ and $A^3$ groups are the same or different at each instance and are $C(R^3)_2$ and $A_2$ is $C(R^1)_2$.

6. The compound of claim 1, wherein, in the ring structures of formulae (8), (9), (10) and/or (11), the $R^1$ radicals bonded to the bridgehead are H, D, F or $CH_3$.

7. The compound of claim 1, wherein, in the structure of formula (1), the two Y groups form a ring structure of one of the following formulae (5-A), (5-B), (5-C), (5-D), (5-E) or (5-F):

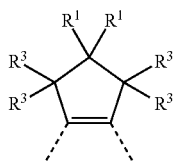

Formula (5-A)

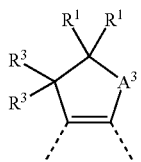

Formula (5-B)

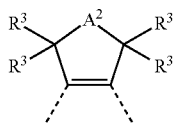

Formula (5-C)

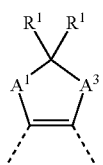

Formula (5-D)

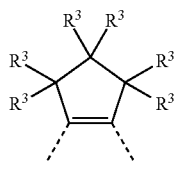

Formula (5-E)

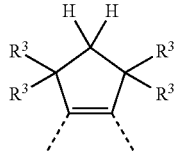

Formula (5-F)

where $A^1$, $A^2$ and $A^3$ are the same or different at each instance and are O or $NR^3$, the dotted lines represent the bonds of the two Y radicals to the ring comprising the $X^1$ radical of formula (1) and $R^1$ and $R^3$ are each as defined above.

8. The compound of claim 1, wherein, in the structure of formula (1), the two Y groups form a ring structure of one of the following formulae (6-A) to (6-F):

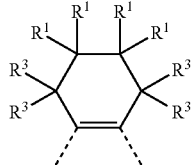

Formula (6-A)

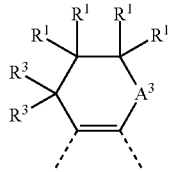

Formula (6-B)

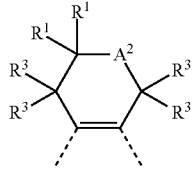

Formula (6-C)

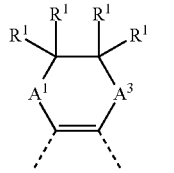

Formula (6-D)

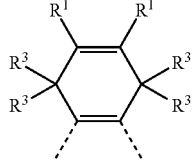

Formula (6-E)

-continued

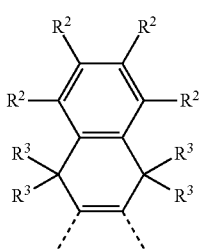

Formula (6-F)

where A¹, A² and A³ are the same or different at each instance and are O or NR³, the dotted lines the bonds of the two Y radicals to the ring comprising the X¹ radical of formula (1), R¹ and R³ are each as defined above.

9. The compound of claim 1, wherein, in the structure of formula (1), the two Y groups form a ring structure of one of the following formulae (8-A) to (8-C):

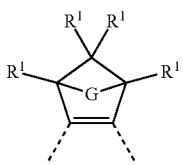

Formula (8-A)

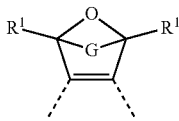

Formula (8-B)

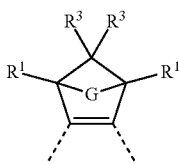

Formula (8-C)

where the symbols used are each as defined above and the dotted lines represent the bonds of the two Y radicals to the ring comprising the X¹ radical of formula (1).

10. The compound of claim 1, wherein, in the structure of formula (1), the two Y radicals together with the groups present for formation of the A ring form a ring structure of one of the following formulae (9-A), (10-A) and (11-A):

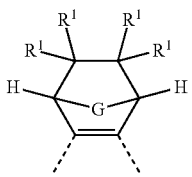

Formula (9-A)

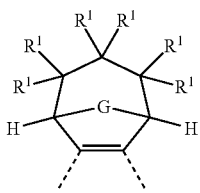

Formula (10-A)

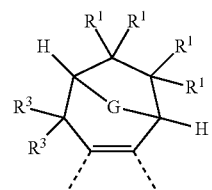

Formula (11-A)

where the symbols used are each as defined above and the dotted lines represent the bonds of the two Y radicals to the ring comprising the X¹ radical of formula (1).

11. The compound of claim 1, wherein the compound has at least two ring structures of the formulae (5) to (11).

12. The compound of claim 1, wherein the compound has a structure of the formula CyG(CyH)$_n$ where CyG and CyH together in each case form a ring and the symbols and indices are as follows:

n is 2 or 3;

CyG is a structural element selected from the formulae

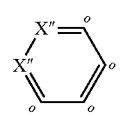

(CyG-1)

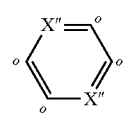

(CyG-2)

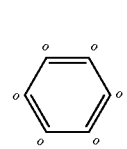

(CyG-3)

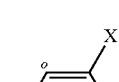

(CyG-4)

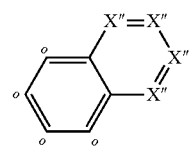

(CyG-5)

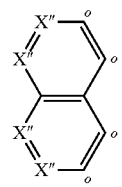

(CyG-6)

(CyG-7) 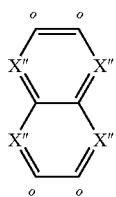
(CyG-8) 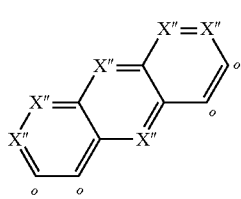
(CyG-9) 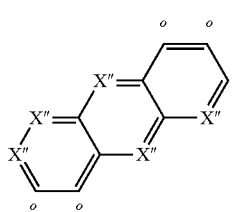
(CyG-10) 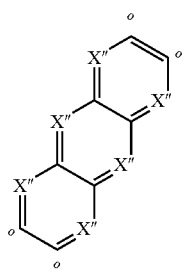
(CyG-11) 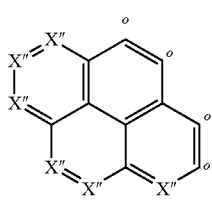
(CyG-12) 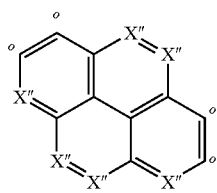
(CyG-13) 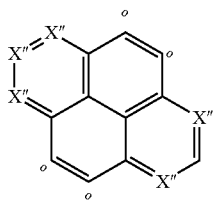
(CyG-14) 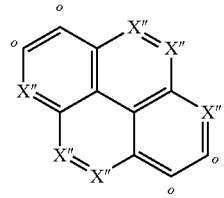
(CyG-15) 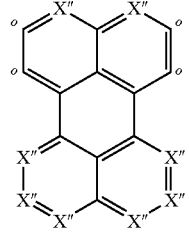
(CyG-16) 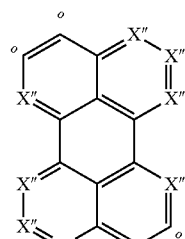
(CyG-17) 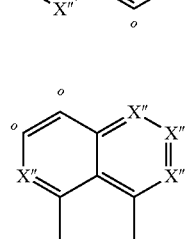
(CyG-18) 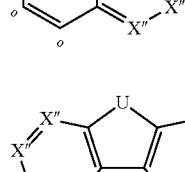
(CyG-19) 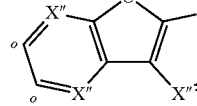
(CyG-20) 

-continued (CyG-21) 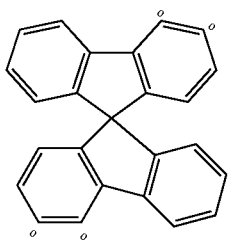

(CyG-22) 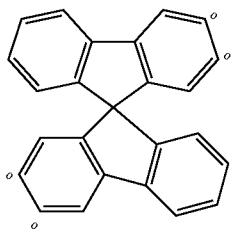

(CyG-23) 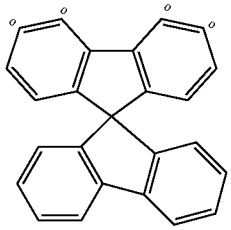

(CyG-24) 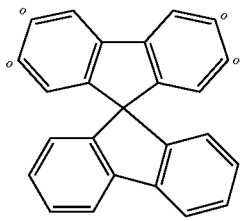

(CyG-25) 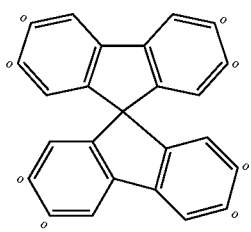

(CyG-26) 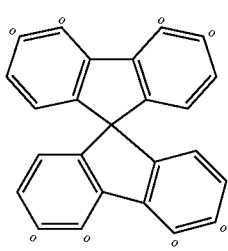

(CyG-27) 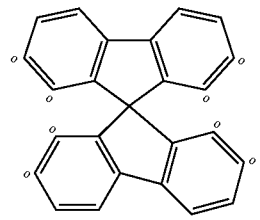

and CyH is at least one structural element of the following formula:

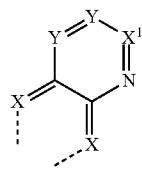

(CyH)

where the symbols used are as defined above, U is selected from the group consisting of O, S, $C(R)_2$, N(R), B(R), $Si(R)_2$, C=O, S=O, $SO_2$, P(R) and P(=O)R, the dotted lines in formulae CyH indicate the bonds to CyG, and CyH binds to CyG in each case at the positions indicated by "o" to form a ring.

13. An oligomer, polymer or dendrimer containing one or more compounds as claimed in claim 1, wherein one or more bonds of the compound to the polymer, oligomer or dendrimer are present.

14. A composition comprising at least one compound as claimed in claim 1 and at least one additional organic functional material.

15. A formulation comprising at least one compound as claimed in claim 1 and at least one solvent.

16. A process for preparing a compound as claimed in claim 1, the process comprising reacting at least one primary arylamine with at least one β-keto vinyl alcohol to give a β-keto enamine compound which is subsequently cyclized.

17. An electronic device comprising a hole blocker material, electron injection material or electron transport material comprising the compound as claimed in claim 1.

18. The electronic device according to claim 17, wherein the electronic device is selected from the group consisting of organic integrated circuits (OICs), organic field-effect transistors (OFETs), organic thin-film transistors (OTFTs), organic electroluminescent devices, organic solar cells (OSCs), organic optical detectors, and organic photoreceptors.

19. The electronic device as claimed in claim 18, wherein the electronic device is an organic electroluminescent device selected from the group consisting of organic light-emitting transistors (OLETs), organic field quench devices (OFQDs), organic light-emitting electrochemical cells (OLECs, LECs, LEECs), organic laser diodes (O-lasers) and organic light-emitting diodes (OLEDs).

20. The compound of claim 1, wherein, in the ring structures of one of the formulae (5), (6), (7), (8), (9), (10), and/or (11), none of the $A^1$, $A^2$, and $A^3$ groups is O, S or $NR^3$.

21. The compound of claim 1, wherein the compound is selected from the group consisting of:

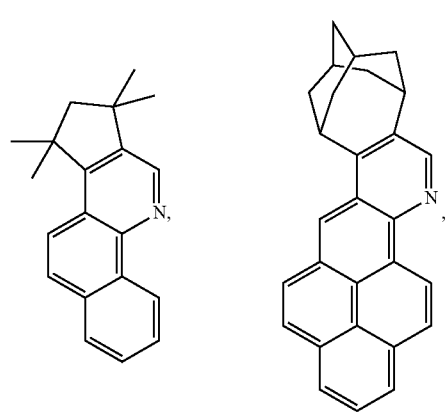
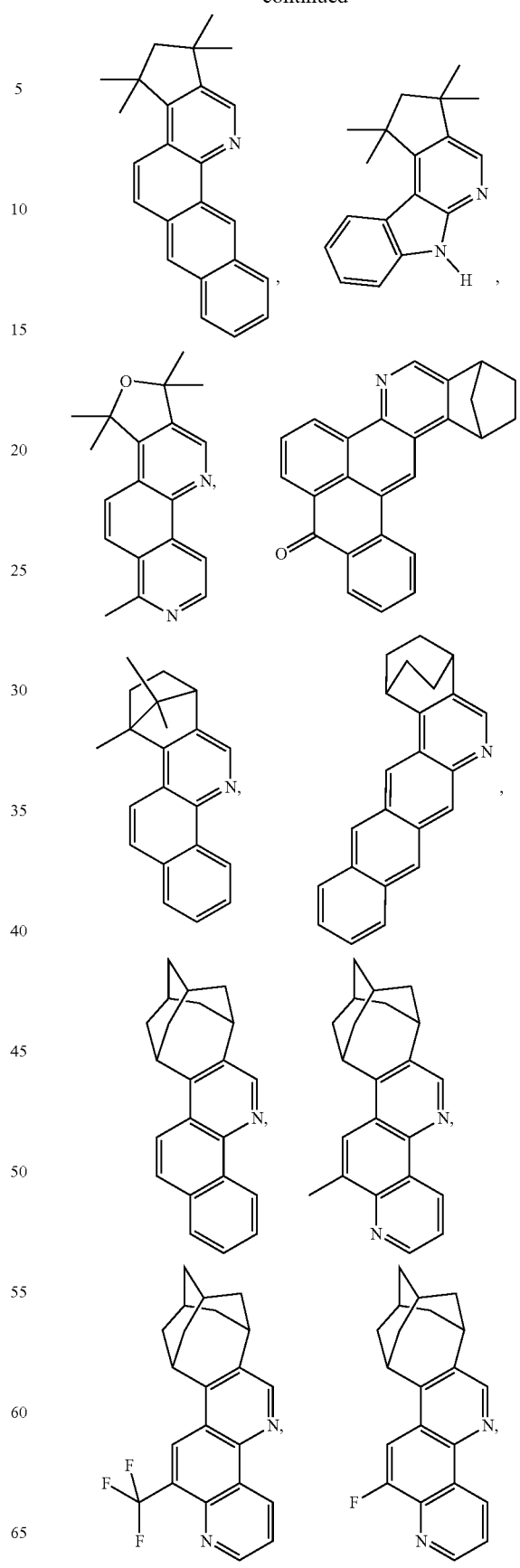

135
-continued
136
-continued
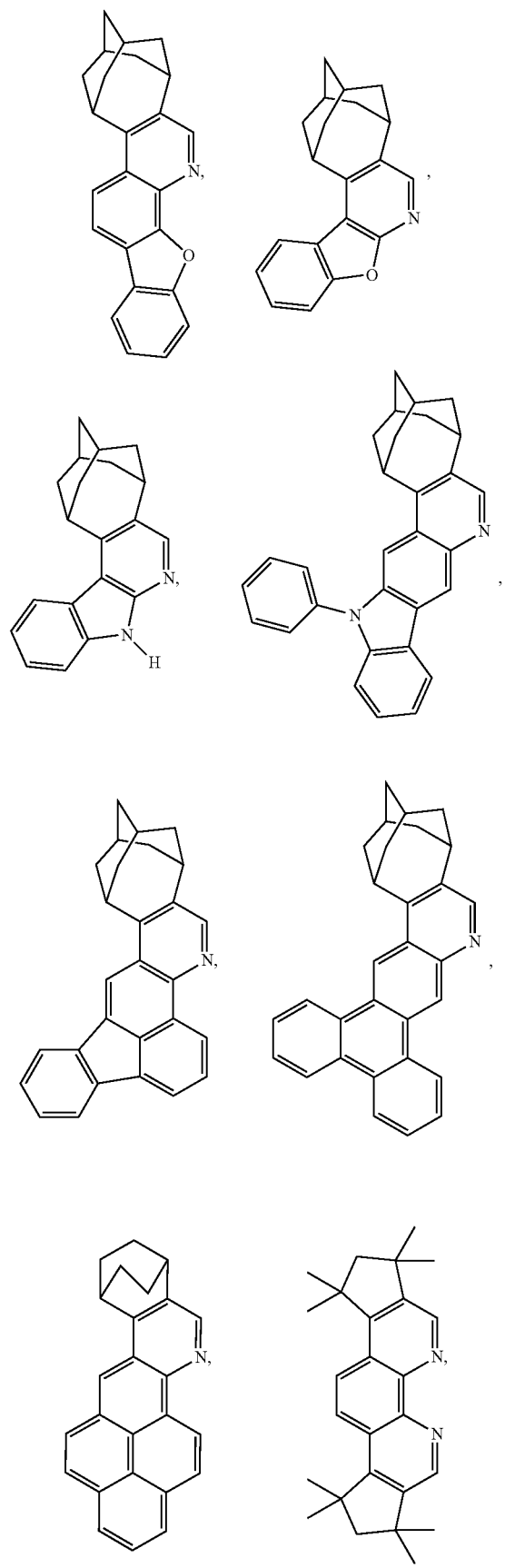
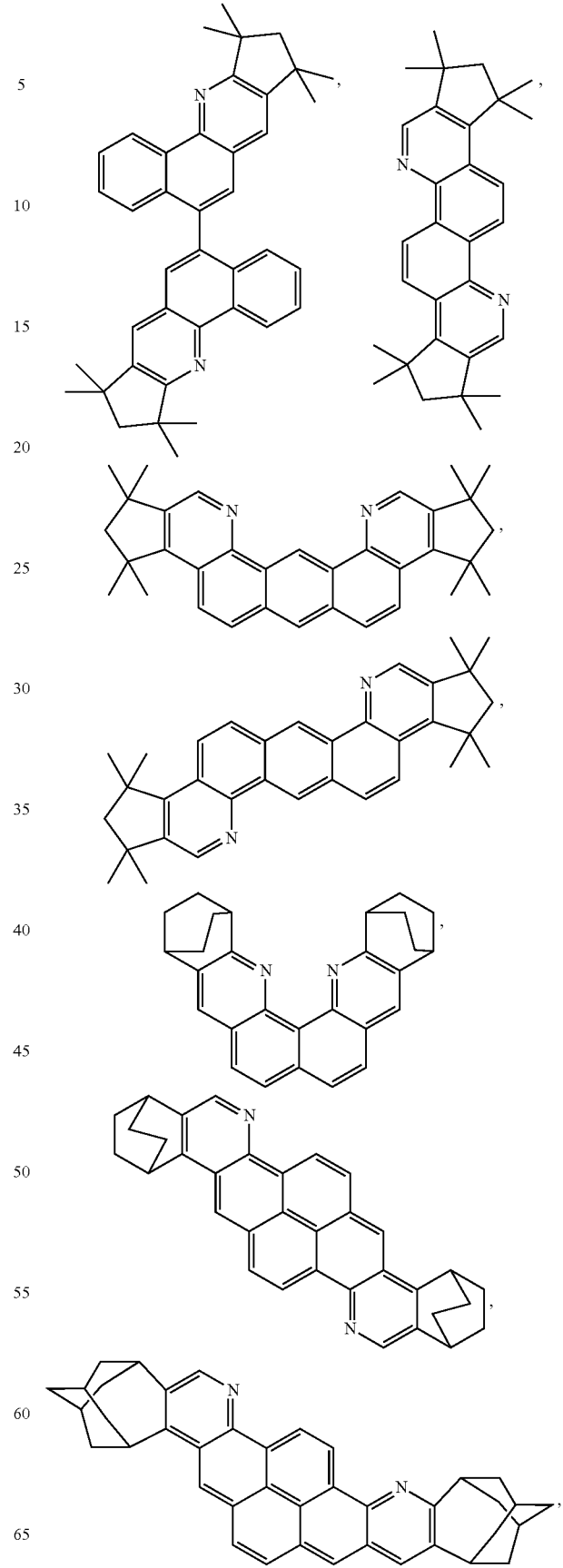

137
-continued
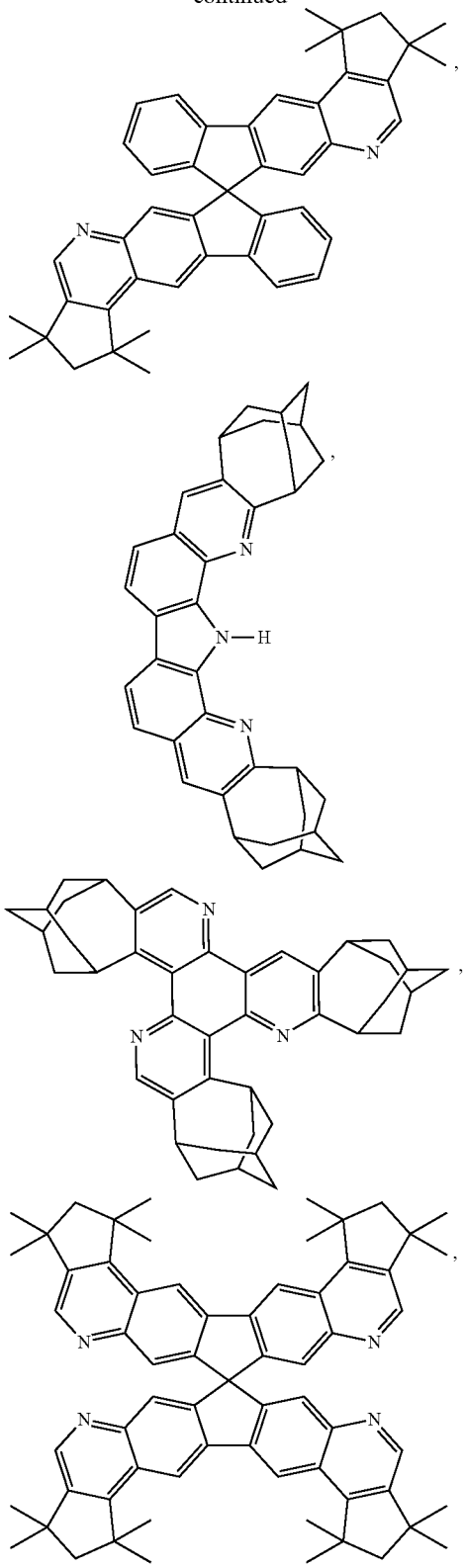
138
-continued
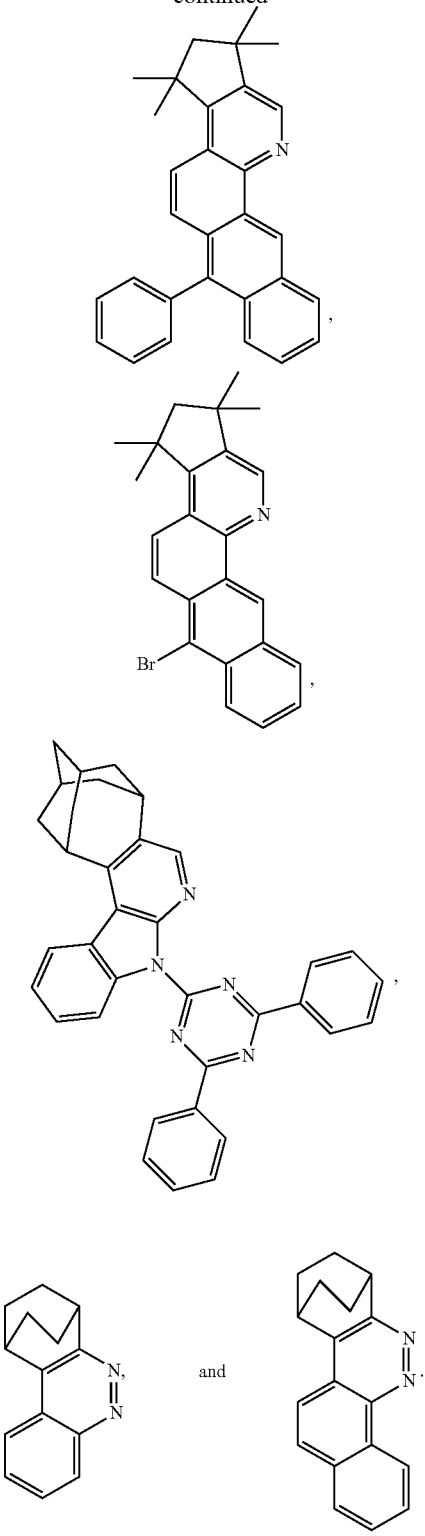
and
* * * * *